US005563168A

United States Patent [19]

Brand et al.

[11] Patent Number: 5,563,168

[45] Date of Patent: Oct. 8, 1996

[54] O-BENZYLOXIME ETHERS AND CROP PROTECTION AGENTS CONTAINING THESE COMPOUNDS

[75] Inventors: Siegbert Brand, Birkenheide; Uwe Kardorff, Mannheim; Reinhard Kirstgen, Neustadt; Bernd Mueller, Frankenthal; Klaus Oberdorf, Eppelheim; Hubert Sauter, Mannheim; Gisela Lorenz, Neustadt; Eberhard Ammermann, Ludwigshafen; Christoph Kuenast, Otterstadt; Albrecht Harreus, Ludwigshafen, all of Germany

[73] Assignee: BASF Aktiengesellschaft, Ludwigshafen, Germany

[21] Appl. No.: 490,895

[22] Filed: Jun. 16, 1995

Related U.S. Application Data

[62] Division of Ser. No. 328,516, Oct. 25, 1994, which is a division of Ser. No. 165,413, Dec. 13, 1993, Pat. No. 5,387,607, which is a division of Ser. No. 962,340, Oct. 15, 1992, Pat. No. 5,292,759, which is a division of Ser. No. 722,209, Jun. 27, 1991, Pat. No. 5,194,662.

[30] Foreign Application Priority Data

| | | | |
|---|---|---|---|
| Jun. 27, 1990 | [DE] | Germany | 40 20 384.0 |
| Jun. 27, 1990 | [DE] | Germany | 40 20 388.3 |

[51] Int. Cl.$^6$ .......................... A01N 43/40; A01N 43/16; C07D 309/06; C07D 213/55

[52] U.S. Cl. .......................... 514/357; 514/183; 514/210; 514/238.2; 514/238.5; 514/255; 514/256; 514/269; 514/274; 514/327; 514/331; 514/351; 514/359; 514/365; 514/367; 514/369; 514/374; 514/376; 514/378; 514/383; 514/384; 514/398; 514/400; 514/424; 514/427; 514/429; 514/432; 514/438; 514/445; 514/459; 514/463; 514/471; 514/475; 544/159; 544/162; 544/163; 544/169; 544/298; 544/310; 544/319; 544/335; 544/384; 544/399; 544/400; 546/221; 546/230; 546/233; 546/235; 546/300; 546/330; 546/335; 546/337; 548/100; 548/170; 548/171; 548/180; 548/204; 548/228; 548/229; 548/243; 548/247; 548/262.2; 548/324.1; 548/336.1; 548/550; 548/556; 548/561; 548/566; 548/567; 548/950; 548/952; 548/965; 548/967; 549/13; 549/28; 549/65; 549/68; 549/69; 549/419; 549/426; 549/449; 549/451; 549/452; 549/475; 549/496; 549/551; 549/552; 549/553

[58] Field of Search .................................... 514/256, 269, 514/274, 351, 357, 459; 544/298, 310, 319, 335; 546/300, 330, 335, 337; 549/419, 426

[56] References Cited

U.S. PATENT DOCUMENTS 5,055,471 10/1991 DeFraine et al. ........................ 514/513

(List continued on next page.)

FOREIGN PATENT DOCUMENTS 0414572 2/1991 European Pat. Off. .

(List continued on next page.)

*Primary Examiner*—Richard L. Raymond
*Attorney, Agent, or Firm*—Oblon, Spivak, McClelland, Maier, & Neustadt, P.C.

[57] ABSTRACT

O-Benzyloxime ethers of the formula I

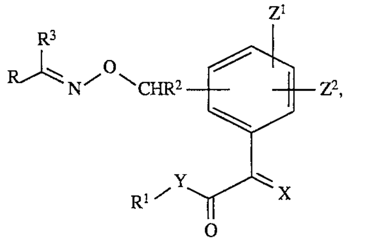

(I)

where

X is substituted or unsubstituted $CH_2$, NOalkyl

Y is

O, S, $NR^5$ $R^1$, $R^2$, $R^5$ are H, alkyl $Z^1$, $Z^2$ are H, halogen, methyl, methoxy, cyano $R^3$, $R^4$ are hydrogen, cyano, substituted or unsubstituted alkyl, alkenyl, cycloalkyl, cycloalkenyl, alkynyl, alkoxy, haloalkoxy, alkylthio, benzylthio, alkylcarbonyl, substituted or unsubstituted phenylcarbonyl, substituted or unsubstituted benzylcarbonyl, alkoxycarbonyl, substituted or unsubstituted phenoxycarbonyl, substituted or unsubstituted benzyloxycarbonyl, $N(R^6)_2$, where $R^6$ is H, alkyl, substituted or unsubstituted phenyl, $-CO-N(R^7)_2$, where $R^7$ is H, substituted or unsubstituted alkyl, substituted or unsubstituted aryl, substituted or unsubstituted aryloxy, substituted or unsubstituted arylthio, substituted or unsubstituted hetaryl, substituted or unsubstituted hetaryloxy, substituted or unsubstituted hetarylthio, substituted or unsubstituted heterocyclyl, substituted or unsubstituted heterocyclyloxy, $R^3$ and $R^4$ together may form a carbocyclic or heterocyclic ring which is substituted or unsubstituted, and $R^3$ or $R^4$ may be halogen, or

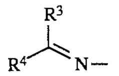

may be

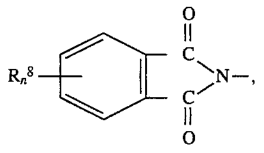

where n is an integer from 1 to 4, and $R^8$ is, or, when n>1, the $R^{8}$'s are identical or different and are each, H, halogen, cyano, nitro or substituted or unsubstituted $C_1$–$C_4$-alkyl, $C_1$–$C_4$-alkoxy, $C_1$–$C_4$-haloalkyl, $C_1$–$C_4$-haloalkoxy, aryl, aryloxy, benzyloxy, hetaryl or hetaryloxy.

and crop protection agents containing these compounds.

15 Claims, No Drawings

U.S. PATENT DOCUMENTS

| | | | |
|---|---|---|---|
| 5,221,691 | 6/1993 | Clough et al. | 514/619 |
| 5,238,956 | 8/1993 | Clough et al. | 514/506 |
| 5,342,837 | 8/1994 | Clough et al. | 514/247 |
| 5,346,902 | 9/1994 | Clough et al. | 514/269 |
| 5,371,084 | 12/1994 | DeFraine et al. | 514/241 |
| 5,432,197 | 7/1995 | DeFraine et al. | 514/539 |

FOREIGN PATENT DOCUMENTS

| | | |
|---|---|---|
| 414153 | 2/1991 | European Pat. Off. . |
| 426460 | 5/1991 | European Pat. Off. . |
| 460575 | 12/1991 | European Pat. Off. . |

O-BENZYLOXIME ETHERS AND CROP PROTECTION AGENTS CONTAINING THESE COMPOUNDS

This is a Division, of application Ser. No. 08/328,516, filed on Oct. 25, 1994, which is a Division of application Ser. No. 08/165,413, filed on Dec. 13, 1993, now U.S. Pat. No. 5,387,607, which is a Division of application Ser. No. 07/962,340, filed on Oct. 15, 1992, now U.S. Pat. No. 5,292,759, which is a Division of application Ser. No. 07/722,209, filed on Jun. 27, 1991, now U.S. Pat. No. 5,194,662.

The present invention relates to novel O-benzyloxime ethers and a method for controlling pests, in particular fungi, insects, nematodes and spider mites with these compounds.

It is known that substituted phenylacetic acid oxime derivatives can be used as fungicides (European Patent 253,213). However, their action is unsatisfactory.

We have found, surprisingly, that O-benzyloxime ethers of the general formula I

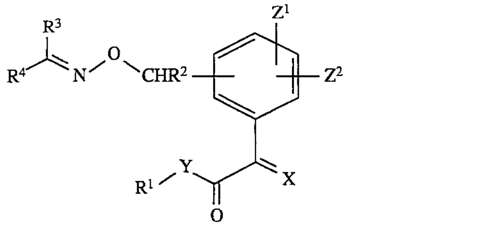

(I)

where

- X is $CH_2$, CH—$C_1$–$C_4$-alkyl, CH—$C_1$–$C_4$-alkoxy, CH—$C_1$–$C_4$-alkylthio or N—$C_1$–$C_4$-alkoxy,
- Y is O, S or $NR^5$,
- $R^1$, $R^2$ and $R^5$ are each H or $C_1$–$C_4$-alkyl,
- $Z^1$ and $Z^2$ are identical or different and are each H, halogen, methyl, methoxy or cyano,
- $R^3$ and $R^4$ are identical or different and are each hydrogen, cyano, straight-chain or branched $C_1$–$C_{10}$-alkyl, $C_1$–$C_4$-haloalkyl, $C_3$–$C_6$-cycloalkyl, $C_3$–$C_6$-halocycloalkyl, $C_3$–$C_6$-cycloalkyl-$C_1$–$C_4$-alkyl, $C_1$–$C_4$-alkoxy-$C_1$–$C_4$-alkyl, $C_1$–$C_4$-alkylthio-$C_1$–$C_4$-alkyl, arylthio-$C_1$–$C_4$-alkyl, $C_2$–$C_6$-alkenyl, $C_2$–$C_5$-haloalkenyl, $C_3$–$C_6$-cycloalkenyl, $C_3$–$C_6$-halocycloalkenyl, $C_2$–$C_6$-alkynyl, $C_1$–$C_6$-alkoxy, $C_1$–$C_6$-haloalkoxy, $C_1$–$C_4$-alkylthio, benzylthio, $C_1$–$C_4$-alkylcarbonyl, unsubstituted or substituted phenylcarbonyl, unsubstituted or substituted benzylcarbonyl, $C_1$–$C_4$-alkoxycarbonyl, unsubstituted or substituted phenoxycarbonyl, unsubstituted or substituted benzyloxycarbonyl, unsubstituted or substituted aryl, unsubstituted or substituted aryloxy, unsubstituted or substituted arylthio, unsubstituted or substituted aryl-$C_1$–$C_4$-alkyl, unsubstituted or substituted aryl-$C_1$–$C_4$-alkenyl, unsubstituted or substituted aryloxy-$C_1$–$C_4$-alkyl, unsubstituted or substituted arylthio-$C_1$–$C_4$-alkyl, unsubstituted or substituted hetaryl, unsubstituted or substituted hetaryloxy, unsubstituted or substituted hetarylthio, unsubstituted or substituted hetaryl-$C_1$–$C_4$-alkyl, unsubstituted or substituted hetaryl-$C_2$–$C_4$-alkenyl, unsubstituted or substituted hetaryl-oxy-$C_1$–$C_4$-alkyl, unsubstituted or substituted heterocyclyl, unsubstituted or substituted heterocyclyloxy, $N(R^6)_2$, where the radicals $R^6$ are identical or different and are each H, $C_1$–$C_6$-alkyl or unsubstituted or substituted phenyl, or
- —CO—$N(R^7)_2$, where the radicals $R^7$ are identical or different and are each H or $C_1$–$C_4$-alkyl, substituents, in addition to hydrogen, being halogen, cyano, nitro, $C_1$–$C_4$-alkyl, $C_1$–$C_4$-alkoxy, $C_1$–$C_4$-haloalkyl, $C_1$–$C_4$-haloalkoxy, $C_1$–$C_{10}$-alkoximino-$C_1$- or $C_2$-alkyl, aryl, aryloxy, benzyloxy, hetaryl, hetaryloxy, $C_3$–$C_6$-cycloalkyl, heterocyclyl or heterocyclyloxy, or
- $R^3$ and $R^4$ together may form a carbocyclic or heterocyclic ring which may be substituted by the abovementioned substituents, and $R^3$ or $R^4$ may be halogen, or

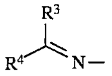

may be

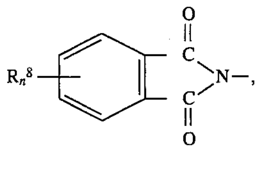

where

- n is an integer from 1 to 4, and
- $R^8$ is, or, when n>1, the $R^8$'s are identical or different and are each, H, halogen, cyano, nitro or substituted or unsubstituted
  $C_1$–$C_4$-alkyl, $C_1$–$C_4$-alkoxy, $C_1$–$C_4$-haloalkyl, $C_1$–$C_4$-haloalkoxy, aryl, aryloxy, benzyloxy, hetaryl or hetaryloxy, have excellent fungicidal, insecticidal, nematicidal and acaricidal activity which is better than that of the known phenylacetic acid derivatives.

The fungicidal action is preferred.

The radicals stated for the general formula I may, for example, have the following meanings: X may be $C_1$–$C_4$-alkylidene (eg. methylidene, ethylidene, n- or isopropylidene, n-, iso-, sec- or tert-butylidene), $C_1$–$C_4$-alkoxymethylidene (eg. methoxy-, ethoxy-, n-propoxy, isopropoxy-, n-butoxy-, isobutoxy-, sec-butoxy- or tert-butoxymethylidene), $C_1$–$C_4$-alkylthiomethylidene (eg. methyl-, ethyl-, n-propyl-, isopropyl-, n-butylthio-, isobutylthio-, sec-butylthio- or tert-butylthiomethylidene) or $C_1$–$C_4$-alkoximino (eg. methoximino, ethoximino, n-propoximino, isopropoximino, n-butoximino, isobutoximino, sec-butoximino or tert-butoximino), Y may be O, S or $NR^5$,

- $R^1$, $R^2$ and $R^5$ may each be H or $C_1$–$C_4$-alkyl (eg. methyl, ethyl, n- or isopropyl, n- or iso-, sec- or tert-butyl), $Z^1$ and $Z^2$ may be H, halogen (eg. fluorine, chlorine, bromine or iodine), methyl, methoxy or cyano, and
- $R^3$ and $R^4$ may be identical or different and are each hydrogen, cyano, straight-chain or branched $C_1$–$C_{10}$-alkyl (eg. methyl, ethyl, n- or isopropyl, n-, iso-, sec- or tert-butyl, n-, iso-, sec-, tert- or neopentyl, n-hexyl or n-decyl), $C_1$–$C_4$-haloalkyl (eg. trifluoromethyl, 2-fluoroethyl, 2,2,2-trifluoroethyl, pentafluoroethyl, fluorodichloromethyl, difluorochloromethyl, chloromethyl, dichloromethyl, trichloromethyl, 2-chloroethyl, 2,2,2-trichloroethyl or pentachloroethyl),
- $C_3$–$C_6$-cycloalkyl (eg. cyclopropyl, cyclobutyl, cyclopentyl or cyclohexyl),
- $C_3$–$C_6$-halocycloalkyl (eg. 2,2-difluorocyclopropyl, 2,2-dichlorocyclopropyl, 2,2-dibromocyclopropyl, 2,2-dichloro-3-methylcyclopropyl or tetrafluorocyclobutyl), $C_3$–$C_6$-cycloalkyl-$C_1$–$C_4$-alkyl (eg. 1-methylcyclopropyl, 2,2-dimethylcyclopropyl or 1-methylcyclohexyl), $C_1$–$C_4$-alkoxy-$C_1$–$C_4$-alkyl (eg. methoxymethyl, ethoxymethyl, n- or isopropoxymethyl, n-, iso-, sec- or tert-butoxymethyl, 2-methoxyprop-2-yl, 2-ethoxyprop-2-yl, 2-n- or isopropoxyprop-2-yl or 2-n-, iso-, sec- or tert-butoxyprop-2-yl), $C_1$–$C_4$-alkylthio-$C_1$–$C_4$-alkyl (eg. methylthiomethyl, ethylthiomethyl, n- or isopropylthiomethyl, n-, iso-, sec- or tert-butylthiomethyl, 2-methylthioprop-2-yl, 2-ethylthioprop-2-yl, 2-n- or isopropylthioprop-2-yl or 2-n-, iso-, sec- or tert-butylthioprop-2-yl), aryl(phenyl)thio-$C_1$–$C_4$-alkyl (eg. phenylthiomethyl or 2-chlorophenylthiomethyl), $C_2$–$C_6$-alkenyl (eg. vinyl, 1-propenyl, 2-propenyl, 2-butenyl, 3-butenyl, 1-methyl-2-propenyl, 3-methyl-2-butenyl or 2-methyl-2-penten-5-yl), $C_2$–$C_5$-haloalkenyl (eg. 2,2-difluorovinyl, 2,2-dichlorovinyl, 3,3,3-trifluoropropenyl, 3,3,3-trichloropropenyl or 3-chloro-2-propenyl), $C_3$–$C_6$-cycloalkenyl (eg. cyclopent-1-enyl, cyclopentadienyl or cyclohex-1-enyl), $C_3$–$C_6$-halocycloalkenyl (eg. pentafluorocyclopentadienyl or pentachlorocyclopentadienyl), $C_2$–$C_4$-alkynyl (eg. ethynyl, 1-propynyl or 1-propargyl), $C_1$–$C_4$-alkoxy (eg. methoxy, ethoxy, n- or isopropoxy or n-, iso-, sec- or tert-butoxy), $C_1$–$C_4$-alkylthio (eg. methylthio, ethylthio, n- or isopropylthio or n-, iso-, sec- or tert-butylthio) or benzylthio, $C_1$–$C_4$-haloalkoxy (eg. trifluoromethoxy, pentafluoroethoxy or 1,1,2,2-tetrafluoroethoxy), $N(R^6)_2$ (eg. amino, methylamino, dimethylamino, ethylamino, diethylamino, di-n-propylamino, diisopropylamino, di-n-butylamino or diisobutylamino), $C_1$–$C_4$-alkylcarbonyl (eg. acetyl, propionyl, butyryl, isobutyryl or pivaloyl), unsubstituted or substituted phenylcarbonyl (eg. benzoyl or 4-chlorobenzoyl), unsubstituted or substituted benzylcarbonyl (eg. benzylcarbonyl), $C_1$–$C_4$-alkoxycarbonyl (eg. methoxycarbonyl, ethoxycarbonyl, n- or isopropoxycarbonyl or n-, iso-, sec- or tert-butoxycarbonyl), unsubstituted or substituted phenoxycarbonyl (eg. phenoxycarbonyl or 4-chlorophenoxycarbonyl), unsubstituted or substituted benzyloxycarbonyl (eg. benzyloxycarbonyl), —CO—$N(R^7)_2$ (eg. aminocarbonyl, dimethylaminocarbonyl, diethylaminocarbonyl, diisopropylaminocarbonyl, phenylaminocarbonyl or N-methyl-N-phenylaminocarbonyl), unsubstituted or substituted aryl (eg. phenyl, naphthyl or anthryl), unsubstituted or substituted aryloxy (eg. phenoxy, naphthyloxy or anthryloxy), unsubstituted or substituted arylthio (eg. phenylthio), unsubstituted or substituted aryl-$C_1$–$C_4$-alkyl ( eg. benzyl, 1-phenethyl, 2-phenethyl, 1-phenylpropyl, 2-phenylpropyl, 3-phenylpropyl, 2-methyl-3-phenylpropyl, 2-methyl-2-phenylpropyl or 4-phenylbutyl), unsubstituted or substituted aryl-$C_1$–$C_4$-alkenyl (eg. phenyl-1-ethenyl, 2-phenyl-1-propenyl, 2,2-diphenylethenyl, 1-phenyl-1-propen-2-yl or 1-phenyl-1-ethenyl), unsubstituted or substituted aryloxy-$C_1$–$C_4$-alkyl (eg. phenoxymethyl), unsubstituted or substituted arylthio-$C_1$–$C_4$-alkyl (eg. phenylthiomethyl), unsubstituted or substituted hetaryl (eg. pyridyl, 2-pyridyl, 3-pyridyl, 4-pyridyl, pyrimidinyl, 2,6-pyrimidinyl, 1,5-pyrimidinyl, thienyl, 2-thienyl, 3-thienyl, furyl, 2-furyl, 3-furyl, 1-pyrrolyl, 1-imidazolyl, 1,2,4-triazolyl, 1,3,4-triazolyl, 4-thiazolyl or 2-benzothiazolyl), unsubstituted or substituted hetaryloxy (eg. 2-pyridyloxy or 2-pyrimidinyloxy), unsubstituted or substituted hetarylthio (eg. 2-pyridylthio, 2-pyrimidinylthio or 2-benzothiazolylthio), unsubstituted or substituted hetaryl-$C_1$–$C_4$-alkyl (eg. 2-pyridylmethyl or 3-pyridylmethyl), unsubstituted or substituted hetaryloxy-$C_1$–$C_4$-alkyl (eg. furfurylmethoxy, thienylmethoxy, 3-isoxasolylmethoxy, 2-oxasolylmethoxy or 2-pyridylmethoxy), unsubstituted or substituted hetaryl-$C_2$–$C_4$-alkenyl (eg. 2'-furyl-2-ethenyl, 2'-thienyl-2-ethenyl or 3'-pyridyl-2-ethenyl), unsubstituted or substituted heterocyclyl (eg. oxiranyl, 1-aziridinyl, 1-azetidinyl, 1-pyrrolidinyl, 2-tetrahydrofuryl, 2-tetrahydropyranyl, 3-tetrahydropyranyl, 1-piperidinyl, 1-morpholinyl, 1-piperazinyl, 1,3-dioxanyl or 3-tetrahydrothiopyranyl) or unsubstituted or substituted heterocyclyloxy (eg. 2-dihydropyranyloxy or 2-tetrahydropyranyloxy).

The radicals referred to above in connection with unsubstituted or substituted are, in addition to hydrogen, for example, fluorine, chlorine, bromine, iodine, cyano, nitro, methyl, ethyl, isopropyl, tert-butyl, methoxy, ethoxy, isopropoxy, tert-butoxy, trifluoromethyl, chloromethyl, dichloromethyl, trichloromethyl, trifluoromethoxy, 1,1,2,2-tetrafluoroethoxy, methoximinomethyl, ethoximinomethyl, n-propoximinomethyl, n-butoximinomethyl, n-pentyloximinomethyl, n-hexyloximinomethyl, allyloximinomethyl, benzyloximinomethyl, isopropoximinomethyl, isobutoximinomethyl, tert-butoximinomethyl, methylimino-1-ethyl, ethoximino-1-ethyl, n-propoximino-1-ethyl, n-butoximino-1-ethyl, n-pentyloximino-1-ethyl, n-hexyloximino-1-ethyl, allyloximino-1-ethyl, benzyloximino-1-ethyl, phenyl, phenoxy, benzyloxy, imidazol-1-yl, piperazin-1-yl, 4-morpholinyl, piperidin-1-yl, pyrid-2-yloxy, cyclopropyl, cyclohexyl, oxiranyl, 1,3-dioxan-2-yl, 1,3-dioxolan-2-yl and tetrahydropyran-2-yloxy.

The group

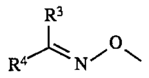

may also be the radical of a carbocyclic or heterocyclic oxime (eg. cyclopentanone oxime, cyclohexanone oxime, cycloheptanone oxime, 2-adamantanone oxime, D-camphor oxime, 1-tetralone oxime, 1-indanone oxime, 9-fluorenone oxime, 1-methyl-4-piperidone oxime, violuric acid or N,N-dimethylviluric acid).

$R^3$ and $R^4$ together then form, for example, a cyclopentyl, cyclohexyl, cycloheptyl, adamantyl, camphenyl, tetralin, indane or fluorene ring.

One of the radicals $R^3$ or $R^4$ may furthermore be halogen (eg. fluorine, chlorine, bromine or iodine).

n may be 1, 2, 3 or 4 and $R^8$ may be for example H, fluorine, chlorine, bromine, iodine, cyano, nitro, methyl, ethyl, isopropyl, tert-butyl, methoxy, ethoxy, isopropoxy, tert-butoxy, trifluoromethyl, chloromethyl, dichloromethyl, trichloromethyl, trifluoromethoxy, 1,1,2,2-tetrafluoromethoxy, phenyl, phenoxy, benzyloxy or pyrid-2-yl, where these radicals in turn may be substituted by fluorine, chlorine, bromine, iodine, cyano, methyl or methoxy.

Among the compounds in which $R^3$ and $R^4$ are hydrogen, the preferred compounds are those in which either only $R^3$ or only $R^4$ is hydrogen, in particular the compounds in which $R^3$ is hydrogen.

Also preferred are compounds of the formula II in which x is $CH_2$, $CHCH_3$, $CHC_2H_5$, $CHOCH_3$, $CHOC_2H_5$, $CHSCH_3$ or $CHSC_2H_5$, Y is 0, $R^1$ is $C_1$–$C_4$-alkyl, $R^2$ is H or methyl, $R^3$ and $R^4$ are identical or different and each is hydrogen, cyano, straight-chain or branched $C_1$–$C_{10}$-alkyl, $C_1$–$C_4$-haloalkyl, $C_3$–$C_6$-cycloalkyl, $C_3$–$C_6$-halocycloalkyl, $C_3$–$C_6$-cycloalkyl-$C_1$–$C_4$-alkyl, $C_1$–$C_4$-alkoxy-$C_1$–$C_4$-alkyl, $C_1$–$C_4$-alkylthio-$C_1$–$C_4$-alkyl, arylthio-$C_1$–$C_4$-alkyl, $C_2$–$C_6$-alkenyl, $C_2$–$C_6$-alkynyl, $C_2$–$C_4$-haloalkenyl, $C_1$–$C_6$-alkoxy, $C_1$–$C_6$-alkylthio, $C_1$–$C_4$-alkylcarbonyl, $C_1$–$C_4$-alkoxycarbonyl, substituted or unsubstituted aryl, substituted or unsubstituted aryloxy, substituted or unsubstituted arylthio, substituted or unsubstituted aryl-$C_1$–$C_4$-alkyl, substituted or unsubstituted aryl-$C_2$–$C_4$-alkenyl, substituted or unsubstituted aryloxy-$C_1$–$C_4$-alkyl, substituted or unsubstituted hetaryl, substituted or unsubstituted hetaryloxy, substituted or unsubstituted hetarylthio or substituted or unsubstituted heterocyclyl, or each is $N(R^6)_2$, $R^6$ being identical or different and denoting M, $C_1$–$C_6$-alkyl, $C_3$–$C_6$-cycloalkyl or substituted or unsubstituted phenyl, or each is —CO—$N(R^7)_2$, $R^7$ being identical or different and denoting H or $C_1$–$C_4$-alkyl, the term "substituted" denoting the radicals listed in claim 1, and $R^3$ and $R^4$ may together denote a carbocyclic or heterocyclic ring which may be substituted by the radicals given under "substituted", and $R^3$ and $R^4$ may be halogen, and $Z^1$ and $Z^2$ are hydrogen, fluorine, chlorine, bromine, iodine, methyl, cyano or methoxy.

Owing to the C═C or C═N double bonds, the novel compounds of the general formula I may be obtained in the preparation as E/Z isomer mixtures. These can be separated into the individual components in a conventional manner, for example by crystallization or chromatography.

Both the individual isomeric compounds and mixtures thereof form subjects of the invention and can be used as pesticides.

The compounds of the general formula I as claimed in claim 1 are prepared, for example, as described in Scheme 1 ($Z^1$ and $Z^2$ are each H).

Scheme 1

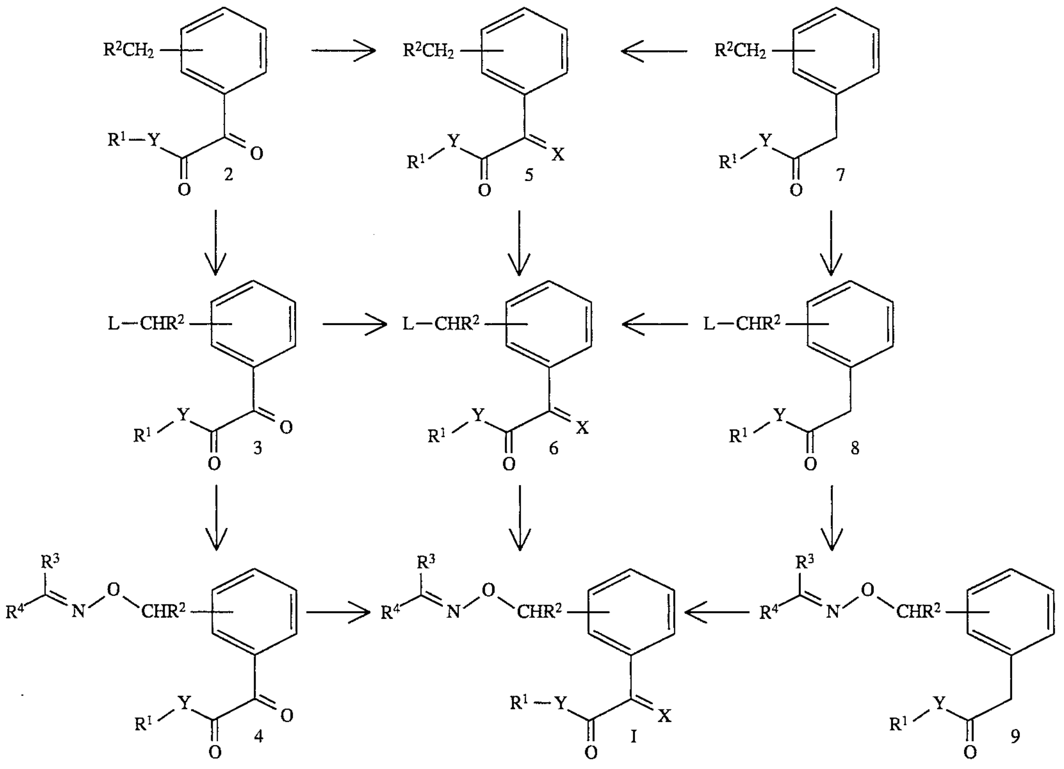

The compounds of the general formula I in which X is $CH_2$, CH-alkyl or CH-alkoxy can be prepared, for example, from the ketoesters 4 by a Wittig or Wittig-Horner reaction (cf. European Patents 348,766 and 178,826 and DE 3 705 389). The similar compounds 5 are likewise obtained from the ketoesters 2.

Alternatively, it is also possible to adopt a procedure in which compounds of the formula 7 or 9 are condensed with suitable reagents, for example with formaldehyde where X is $CH_2$ (cf. DE 3317356), a) with aldehydes (cf. D. M. Brown, J. Chem. Soc. 1948, 2147) or b) first with N,N-dimethylformamide dimethyl acetal, followed by reaction with a Grignard reagent (similarly to C. Jutz, Chem. Ber. 91 (1958), 1867) where X is CH-alkyl, or with a formate followed by alkylation (cf. European Patent 178,826) where X is CH—O-alkyl. Further preparation methods for the compounds of the formula 5 and I where X is CH—O-alkyl are described in European Patent 178,826.

Another possible method for preparing the compounds of the formula I where X is CH-alkyl and $YR_2$ is COOAlk is to react ketene acetals with phenylchlorocarbenes (S. N.

Slougui and G. Rousseau, Synth. Commun. 12 (5) (1982), 401–407).

For compounds of the general formula I where X is CH—S-alkyl, the preparation can be carried out by the methods described in European Patents 244,077 or 310,954.

The intermediates of the formulae 3, 6 and 8 can be prepared from the compounds 2, 5 and 7 by halogenating the latter by a known method, for example with chlorine, bromine or N-bromosuccinimide, in an inert solvent (eg. $CCl_4$ or cyclohexane), with exposure to, for example, a Hg vapor lamp or in the presence of a free radical initiator, eg. dibenzoyl peroxide, or by introducing the radicals L, eg. mesylate, tosylate, acetate or triflate, via suitable intermediates (where L is halogen or OH).

The oxime ethers of the formula I where X is N-Oalkyl can be prepared from 4 a) by reaction with an O-alkylhydroxylamine hydrochloride or b) with hydroxylamine hydrochloride and subsequent alkylation with an alkylating agent (eg. an alkyl iodide, dialkyl sulfate, etc.) (cf. DE 3 623 921).

Furthermore, a phenylacetic ester of the formula 9 can be converted with a base (eg. NaOMe, NaH, K tertbutylate, etc.) in a solvent (eg. diethyl ether, toluene, tert-butanol, etc.) by a method similar to that in European Patent 254,426 into its anion and can be converted into the oxime with a suitable nitrosating agent (such as methyl nitrite, amyl nitrate, tert-butyl nitrite, etc.). The resulting oximate is alkylated with an alkylating agent (eg. an alkyl iodide or dialkyl sulfate).

The same processes can also be applied to the compounds of the formulae 2 and 7, and the resulting oxime ethers 5 can be converted in a known manner (European Patent 254,426) via the intermediates 6 (L is, for example, halogen) into the desired compounds I.

In the preparation processes described above, Y-$R^1$ is usually alkoxy.

The compounds in which $YR^1$ is OH (11) can be prepared by methods known from the literature (Organikum 16th edition, pages 415 and 622), from the compounds of the general formula I where $YR^1$ is COOAlkyl (10) (cf. Scheme 2):

Alternatively, the nitriles 12 can be converted in a known manner (cf. Organikum 16th edition, page 424 et seq. (1985) into the carboxylic acids 11.

The resulting carboxylic acids 11 can be converted in a conventional manner into the acyl chlorides 14 (cf. Organikum 16th edition, page 423 et seq. (1985). The conversion of 14 into the amides 15 is effected by methods similar to that described in Organikum 16th edition, page 412 (1985).

The thioesters 13 are obtained from the acyl chlorides 14 (similarly to Houben-Weyl Vol. 8, page 464 et seq. (1952)).

Alternatively, the thioesters 13 can also be prepared from the acids 11 (similarly to Houben-Weyl Vol. E5, page 855 et seq. (1985)).

The amides 15 in which $R^1$ and $R^5$ are each H can also be prepared from the nitriles 12 by processes known from the literature (cf. Synthesis 1980, 243).

The preparation of the compounds of the general formulae 2 and 7 with ortho-methyl substitution at the aromatic ($R^2$=H) is known.

($YR^1$=OAlkyl; cf. European Patents 178,826 and 260, 832).

The oximes required for the preparation of the compounds of the general formula I are either known or can be prepared by one of the processes shown in Scheme 3.

Scheme 3

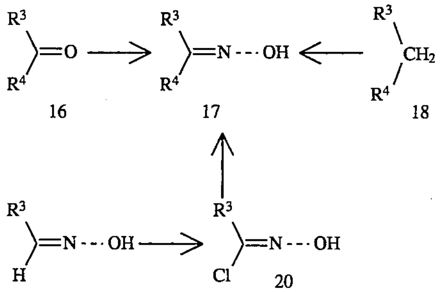

16 17 18 19 20

Methods for the conversion of 16 or 18 into 17 are described in Houben-Weyl, Vol. 10/4 (1968).

Scheme 2

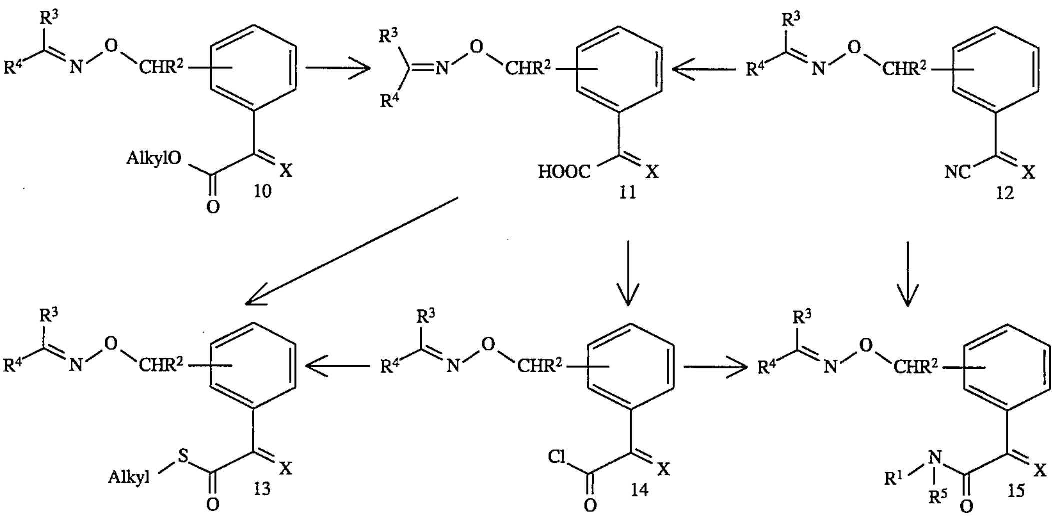

10 11 12 13 14 15

Furthermore, aldoximes 19 can be chlorinated by known methods and can be reacted with, for example, a cyanide to give the derivatives 17 ($R^4$=CN) (cf. M. R. Zimmermann J. f. prakt. Chemie 66 (1902), 359).

The specific derivatives in which $R^3$ is CN and $R^4$ is alkoxyalkyl are prepared according to European Patent 74,047, those in which $R^3$ is CN and $R^4$ is alkylthioalkyl according to European Patent 150,822 and those in which $R^3$ is CN and $R^4$ is alkyl according to DE 2 304 848.

The method employing $Me_3SiO—NH—SiMe_3$ (R. U. Hoffmann and G. A. Buntain, Synthesis 1987, 831) is used for sterically hindered ketones.

Scheme 4

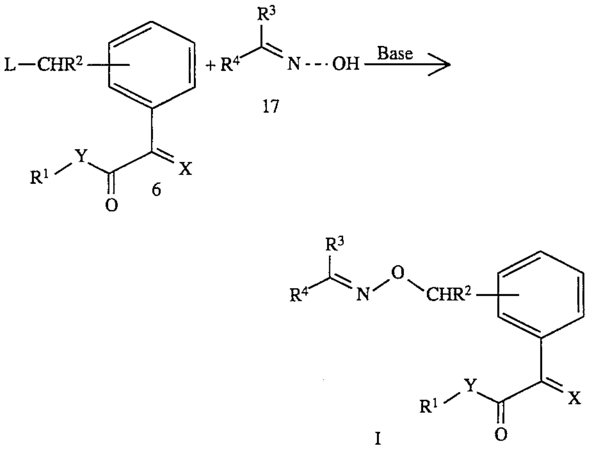

17

6

I

The novel compounds of the general formula I as claimed in claim 1 are prepared, for example, by a method in which an oxime of the formula 17 is reacted with a substituted benzyl compound 6 in which L is a leaving group (eg. chloride, bromide, p-toluenesulfonate, methanesulfonate, triflate or acetate). $R^1$—$R^4$, X and Y have the abovementioned meanings.

The reactions described can be carried out, for example, in an inert solvent (eg. acetone, acetonitrile, dimethyl sulfoxide, dimethylformamide, N-methylpyrrolidone or pyridine) with the use of a base (eg. sodium carbonate, potassium carbonate, sodium hydroxide, potassium hydroxide, sodium hydride of sodium methylate).

The reactions can also be carried out in a two-phase system (eg. dichloromethane or water) with the aid of a suitable phase transfer catalyst (eg. cetyltrimethylammonium chloride or benzyltrimethylammonium chloride).

Another method for the preparation of compounds I ($YR^1$=OAlkyl, X=CH-OAlkyl or N-OAlkyl and L=Cl, Br, tosylate or mesylate) is illustrated by Scheme 5:

Scheme 5:

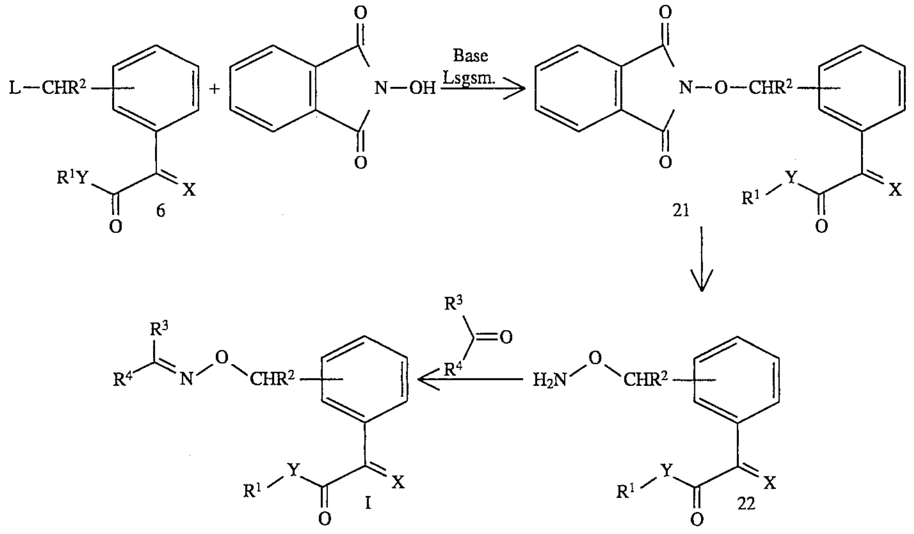

6

21

I

22

This synthesis sequence is carried out, as far as compound 22, similarly to the methods described in European Patent 244,786.

For example, N-hydroxyphthalimide can be converted with a halide or sulfonic ester 6 in the presence of an acid acceptor (eg. triethylamine, potassium carbonate, etc.), in a suitable solvent (eg. N-methylpyrrolidone, dimethylformamide, etc.), into the imidoether 21.

Cleavage to give the O-substituted hydroxylamine 22 can be effected with a mineral acid (eg. HCl; cf. Houben-Weyl Vol. 10/1, page 1181 et seq.) or with a base (for example with hydrazine or ethanolamine).

The conversion of amine 22 to I is carried out in a conventional manner (cf. D. Otzanak, J.C.S. Chem. Commun. 1986, 903).

The Examples and methods which follow are intended to illustrate the preparation of the novel active ingredients and of the novel intermediates.

Method 1: 3,4Dichloroacetophenone oxime 12.0 g (0.17 mol) of hydroxylammonium hydrochloride and 18.9 g (0.1 mol) of 3,4-dichloroacetophenone are added to a mixture of 20 ml of $H_2O$, 100 ml of methanol and 8 g (0.1 mol) of pyridine. Refluxing is carried out for 1 hour, after which the mixture is acidified with 2N HCl and extracted with 3×100 ml of tert-butyl methyl ether. The organic phase is washed with water, dried with $Na_2So_4$ and evaporated down. 19.6 g (96% of theory) of crystals of melting point 92° C., which according to $^1H$-NMR consist of 90% of trans-oxime, are obtained.

Method 2: 2-Oximino-2-tetrahydropyran-2'-ylacetonitrile 265.4 g (2.05 mol) of tetrahydrofuran-2-carbaldehyde oxime in 2 l of diethyl ether are initially taken at from −55° to −60° C. 153.5 g (2.15 mol) of chlorine are then passed in and the temperature is increased to −20° C.; stirring is carried out for 1 hour, the mixture is then evaporated down in a rotary evaporator at 10° C., the residue is taken up in 1.5 l of diethyl ether and the solution is stirred overnight in the absence of light, while cooling with ice. The solution is then filtered and the filtrate is added dropwise, while cooling with ice, to 147.3 g (2.27 mol) of potassium cyanide in 1 l of methanol at 10°–15° C. (exothermic). Stirring is carried out for 5 hours at room temperature (20° C.), after which the precipitate is filtered off under suction and washed twice with diethyl ether. The organic phases are partitioned between tert-butyl methyl ether and water and the residue of the ether phases is crystallized from dichloromethane/n-hexane at 0° C.

After filtration under suction and drying, 208 g (66% of theory) of a spectroscopically pure substance of melting point 105°–106° C. remain.

Method 3: 3-Methoxy-3-methyl-2-oximinobutyronitrile 53.6 g (0.46 mol) of 2-methoxy-2-methylpropionaldehyde oxime in ether (about 1M) are initially taken at from −5° to −10° C. 35.8 g (0.5 mol) of chlorine gas are passed in, after which stirring is carried out for 1 hour at this temperature and the mixture is then evaporated down at 10° C. and the residue is taken up in diethyl ether. 24.7 g (0.5 mol) of sodium cyanide in 375 ml of 20:1 methanol/$H_2O$ are initially taken at 10° C. and the above ethereal solution is rapidly added dropwise. After 4 hours at room temperature, the mixture is filtered under suction and the residue is washed with twice 100 ml of methanol. The combined solutions are evaporated down and the residue is partitioned between methyl tert-butyl ether and water. Drying the organic phase over $Na_2SO_4$, evaporating down and crystallizing from dichloromethane/n-hexane give 41.1 g (63% of theory) of a white powder of melting point 102°–104° C.

Method 4: Methyl 3-methoxy-2-[2'-(phthalimido-oxy)-methyl]-phenylacrylate 10 g (35 mmol) of methyl 3-methoxy-2-(2'-bromomethyl)-phenylacrylate, 5.7 g (35 mmol) of hydroxyphthalimide, 3.9 g (38.6 mmol) of triethylamine and 50 ml of N-methylpyrrolidone are combined and the mixture is stirred for 2 hours at 60° C. It is then poured onto ice water, and the residue is filtered off under suction, washed with water and isopropanol and dried under reduced pressure. 9.0 g (70% of theory) of a crystalline product of melting point 156°–158° C. remain.

$^1$H-NMR ($CDCl_3$): δ=3.60 (s, 3H); 3.75 (s, 3H); 5.12 (s, 2H); 7.13 (dbr, 1H); 7.35 (m, 2H); 7.62 (s, 1H); 7.7–7.9 (m, 5H)

Method 5: Methyl 3-methoxy-2-(2'-aminooxymethyl)-phenylacrylate 10.0 g (27 mmol) of the product from Method 4 are dissolved in 150 ml of methanol and the solution is stirred with 1.4 g (27 mmol) of hydrazine hydrate for 2 hours at room temperature. The precipitate is filtered off under suction, the mother liquor is evaporated down, the residue is stirred with diethyl ether, the precipitate is filtered off under suction again and the mother liquor is evaporated down. 6.0 g (92% of theory) of a yellow oil result (purity according to $^1$H-NMR about 90%). $^1$H-NMR ($CDCl_3$): δ=3.71 (s, 3H); 3.80 (s, 3H); 4.60 (s, 2H); (5.35 (sbr, 2H); 7.0–7.50 (m, 4H); 7.58 (s, 1H).

Method 6: Methyl 2-methoximino-2-(2'-phthalimidooxymethyl)-phenylacetate 2.0 g (7 mmol) of methyl 2-methoximino-2-(2'-bromomethyl)-phenylacetate, 1.1 g (7 mmol) of hydroxyphthalimide and 0.8 g (7.7. mmol) of triethylamine are dissolved in 10 ml of N-methylpyrrolidone and the solution is stirred for 2 hours at 70° C. For working up, ice water is added, and the crystals are filtered off under suction, washed with water and methyl tert-butyl ether and dried.

1.5 g (58% of theory) of crystals of melting point 152°–155° C. remain.

$^1$N-NMR ($CDCl_3$): δ=3.83 (s, 3H); 3.98 (s, 3H); 5.07 (s, 2H); 7.15 (dbr, 1H); 7.45 (mc, 2H); 7.60–7.85 (m, 5H)

Method 7: Methyl 2-methoximino-2-(2'-aminooxymethyl)-phenylacetate 15.0 g (41 mmol) of the product from Method 6 are stirred with 2.1 g (42 mmol) of hydrazine hydrate in 150 ml of methanol for 2 hours at room temperature. The residue is again filtered off under suction, the mother liquor is evaporated down and triturated with diethyl ether, the residue is filtered off under suction and the mother liquor is evaporated down. 7.8 g (80% of theory) of an acid-sensitive oil remain.

$^1$H-NMR ($CDCl_3$): δ=3.90 (s, 3H); 4.03 (s, 3H); 4.59 (s, 2H); 5.35 (sbr, 2H); 7.15 (dbr, 1H); 7.40 (sbr, 3H)

EXAMPLE 1

Methyl 3-methoxy-2-[2'-[1"-(3''', 5'''-dichlorophenyl)-1"-methyl]-iminooxymethyl]-phenylacrylate (No. 582, Table I)

0.6 g (25 mmol) of sodium hydride powder in 100 ml of acetonitrile is initially taken, 5.1 g (25 mmol) of 3,5-dichloroacetophenone oxime are added and the mixture is refluxed for 1 hour. Thereafter, 9.3 g (33 mmol) of methyl 2-(2'-bromomethyl)-phenyl-3-methoxyacrylate in 50 ml of acetonitrile are added dropwise and refluxing is continued for a further 4 hours. The mixture is evaporated down under reduced pressure and then partitioned between methyl tert-butyl ether and saturated ammonium chloride solution, the organic phase is washed with water and the residue obtained by evaporation is crystallized from methyl butyl ether/n-hexane. 4.6 g (45% of theory) of a substance of melting point 87°–88° C. are obtained.

$^1$H-NMR ($CDCl_3$): δ=2.19 (s, 3H); 3.70 (s, 3H); 3.81 (s, 3H); 5.15 (s, 2H); 7.08 (m, 1H); 7.17 (m, 3H); 7.50 (m, 3H); 7.58 (s, 1H)

EXAMPLE 2

Methyl 3-methoxy-2-[2'-(1'-cyano-(-1"-methoxy-1"-methylethyl)-iminooxymethyl]-phenylacrylate (No. 36, Table I)

3.3 g (23 mmol) of 3-methoxy-3-methyl-2-oximinobutyronitrile, 6.6 g (23 mmol) of methyl 2-(2'-bromomethylphenyl)-3-methoxyacrylate and 3.2 g (23 mmol) of potassium carbonate in 60 ml of N,N-dimethylformamide are stirred for 15 hours at room temperature. The mixture is then evaporated down, the residue is taken up in ethyl acetate, the solution is washed with 3×50 ml of water and the organic phase is dried over sodium sulfate, evaporated down and chromatographed over silica gel using 40:1 toluene/ethyl acetate.

Yield: 7.0 g (88% of theory) of an oil.

IR (film): 1,285, 1,258, 1,189, 1,180, 1,131, 1,111, 1,069, 1,008 $cm^{-1}$.

EXAMPLE 3

Methyl 2-methoximino-2-[2'-(1"-(3"', 5"'-dichlorophenyl)-1"-methyl)-iminooxymethyl]-phenylacetate (No. 582, Table II)

0.6 g (25 mmol) of NaH in 50 ml of acetonitrile is initially taken, and 5.1 g (25 mmol) of 3,5-dichloroacetophenone oxime are added at room temperature. Refluxing is carried out for 1 hour, after which 9.4 g (33 mmol) of methyl 2-methoximino-2-(2'-bromomethyl)phenylacetate in 50 ml of acetonitrile are added dropwise and refluxing is continued for a further 4 hours. After evaporating down, partitioning the residue between water/methyl tert-butyl ether, washing the organic phase with water, drying the organic phase with sodium sulfate and evaporating down, the residue is subjected to column chromatography over silica gel using methyl tert-butyl ether/hexane. 5.4 g (53% of theory) of crystals of melting point 95°–97° C. result.

$^1$H-NMR ($CDCl_3$): δ=2.17 (s, 3H); 3.82 (s, 3H); 4.02 (s, 3H); 5.15 (s, 2H); 7.20 (dbr, 1H); 7.25–7.55 (m, 6H)

EXAMPLE 4

Methyl 3-methoxy-2-[2'-(1"-(4"'-bromophenyl)-1"-methyl)-iminooxymethyl]-phenylacrylate (No. 593, Table I)

2.37 g (10 mmol) of methyl 3-methoxy-2-(2'-aminooxymethyl)-phenylacrylate, 1.99 g (10 mmol) of 4-bromoacetophenone, 2 ml of water, 0.8 g of pyridine and 10 ml of methanol are combined and the mixture is stirred for 24 hours at room temperature. The mixture is evaporated down, the residue is partitioned between water/methyl tert-butyl ether and the organic phase is washed with 2N HCl and washed neutral with $NaHCO_3$ and evaporated down, and the residue is chromatographed over $SiO_2$ using methyl tert-butyl ether/hexane. 2.1 g (51% of theory) of crystals of melting point 105°–107° C. result. $^1$H-NMR ($CDCl_3$): δ=2.22 (s, 3H); 3.70 (s, 3H); 3.80 (s, 3H); 5.15 (s, 2H); 7.16 (dbr, 1H); 7.33 (m, 2H); 7.45 (m, 5H); 7.58 (s, 1H)

EXAMPLE 5

Methyl 2-methoximino-2-[2'-(1"-(4"'-nitrophenyl)-1"-methyl)-iminooxymethyl]-phenylacetate (No. 614, Table II)

2.38 g (10 mmol) of methyl 2-methoximino-2-(2'-aminooxymethyl)-phenylacetate, 1.65 g (10 mmol) of 4-nitroacetophenone, 2 ml of water, 0.8 g of pyridine and 10 ml of methanol are reacted as in Example 4. 2.1 g (55% of theory) of crystals of melting point 87°–89° C. are obtained.

$^1$H-NMR ($CDCl_3$): δ=2.22 (s, 3H); 3.81 (s, 3H); 4.02 (s, 3H); 5.18 (s, 2H); 7.20 (dd, 1H); 7.4 (m, 3H); 7.75 (dd, 2H); 8.18 (dd, 2H).

EXAMPLE 6

Methyl 3-methoxy-2-[2'-(1"-(4"'-chlorophenyl)-iminooxymethyl]-phenylacrylate (No. 95 Table 5)

a) 5.5 g (15 mmol) of methyl 3-methoxy-2-[2'-(phthalimidooxy)-methyl]-phenylacrylate (from Method 4 ) in 100 ml of methanol are initially taken, and 0.75 g (15 mmol) of hydrazine hydrate is added at room temperature. After 15 minutes at this temperature, the mixture is evaporated down, the residue is triturated with methyl tert-butyl ether and the cleavage product is filtered off under suction. The mother liquor is evaporated down, the residue is taken up with 50 ml of methanol and 2.1 g (15 mmol) of 4-chlorobenzaldehyde in 50 ml of methanol plus 1 drop of pyridine are added dropwise.

Stirring was carried out overnight at 23° C., after which the product was filtered off under suction, washed with methanol and dried.

2.9 g (54% of theory) of crystals of melting point 87°–89° C. were obtained.

$^1$H-NMR ($CDCl_3$): δ=3.66 (s, 3H); 3.80 (s, 3H); 5.13 (s, 2H); 7.17 (m, 1H); 7.35 (m, 4H); 7.50 (me, 3H); 7.60 (s, 1H); 8.06 (s, 1H).

b) 50 ml of methanol are slowly added to 1.3 g (55 mmol) of NaH powder under a nitrogen atmosphere (evolution of hydrogen). 7.8 g (50 mmol) of 4-chlorobenzaldehyde oxime in 50 ml of methanol are then added at room temperature. Stirring is carried out for half an hour, after which 14.3 g (50 mmol) of methyl 3-methoxy-2-(2'-bromomethyl)-phenylacrylate in 50 ml of methanol are added dropwise and stirring is carried out at room temperature for a further 48 hours. The white residue is filtered off under suction, washed with methanol and dried. 1.9 g (11% of theory) of a product of melting point 82°–84° C. are obtained.

EXAMPLE 7

Methyl 2-methoximino-2-(2'-phthalimidooxymethyl)-phenylacetate (No. 1, Table 8)

2.0 g (7 mmol) of methyl 2-methoxyimino-2-(2'-bromomethyl)-phenylacetate, 1.1 g (7 mmol) of hydroxyphthalimide and 0.8 g (7.7 mmol) of triethylamine are dissolved in 10 ml of N-methylpyrrolidone and the mixture is stirred for 2 hours at 70 ° C. Ice water is added and the crystals are filtered off under suction, washed with water and methyl tert-butyl ether and dried. There remain 1.5 g (58% of theory) of crystals of melting point 152°–155° C. $^1$H-NMR ($CDCl_3$): δ=3.83 (s, 3H); 3.98 (s, 3H); 5.07 (s, 2H); 7.15 (dbr, 1H); 7.45 (mc, 2H); 7.60–7.85 (m, 5H).

The compounds listed in Tables I–IX can be prepared in a similar manner.

TABLE I

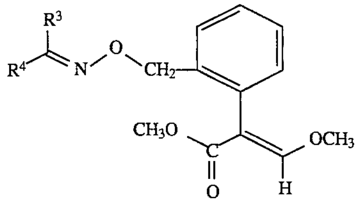

| No. | $R^3$ | $R^4$ | Data |
|---|---|---|---|
| 1 | Cl | Phenyl | |
| 2 | Cl | Cyano | |
| 3 | Cl | Ethoxycarbonyl | |
| 4 | Cl | Cyclopropyl | |

TABLE I-continued

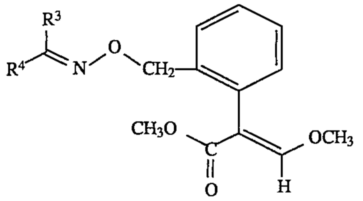

| No. | $R^3$ | $R^4$ | Data |
|---|---|---|---|
| 5 | $CF_3$ | $CF_3$ | |
| 6 | $CF_3$ | Phenyl | |
| 7 | $CCl_3$ | $CCl_3$ | |
| 8 | $CCl_3$ | Phenyl | |
| 9 | $CH_2Cl$ | Phenyl | |
| 10 | $CF_2CF_3$ | Phenyl | |
| 11 | $CF_2Cl$ | Phenyl | |
| 12 | $CHCl_2$ | Phenyl | |
| 13 | Cyclopropyl | Cyclopropyl | |
| 14 | Cyclopropyl | Phenyl | oil; IR (film): 1190, 1129, 1056, 1032, 768 |
| 15 | Cyclopropyl | 4-Fluorophenyl | oil; IR (film): 1508, 1225, 1129, 998, 839 |
| 16 | Cyclopropyl | 4-Chlorophenyl | oil; IR (film): 1490, 1129, 1091, 1014, 1800 |
| 17 | Cyclopropyl | 4-Methoxyphenyl | oil; IR (film): 1251, 1177, 1129, 1033 |
| 18 | Cyclopropyl | 4-Ethoxyphenyl | |
| 19 | Cyclopropyl | 4-Phenoxyphenyl | |
| 20 | Cyclopropyl | Pentachlorophenyl | |
| 21 | Cyclopropyl | Pentafluorophenyl | |
| 22 | Cyclopentyl | Phenyl | |
| 23 | Cyclohexyl | Phenyl | |
| 24 | Phenyl | 2,2-Dichloro-1-methylcyclopropyl | |
| 25 | Phenyl | 2,2-Difluorocyclopropyl | |
| 26 | Phenyl | 2,2-Dichlorocyclopropyl | |
| 27 | Phenyl | 2,2-Dibromocyclopropyl | |
| 28 | Phenyl | 2,2,3,3-Tetrafluorocyclobutyl | |
| 29 | Phenyl | 2,2-Dimethylcyclopropyl | |
| 30 | Phenyl | 1-Methylcyclohexyl | |
| 31 | CN | Methoxymethyl | |
| 32 | CN | Ethoxymethyl | |
| 33 | CN | n-Propoxymethyl | |
| 34 | CN | iso-Propoxymethyl | |
| 35 | CN | tert.-Butoxymethyl | |
| 36 | CN | 2-Methoxyprop-2-yl | oil; IR (film): 1436, 1191, 1131, 1057, 1003 |
| 37 | CN | 2-Ethoxyprop-2-yl | oil; IR (film): 1191, 1177, 1131, 1095, 1010 |
| 38 | CN | 2-n-Propoxyprop-2-yl | oil; IR (film): 1191, 1175, 1131, 1060, 1005 |
| 39 | CN | 2-iso-Propoxyprop-2-yl | oil; IR (film): 1370, 1191, 1172, 1131, 998 |
| 40 | CN | 2-tert.-Butoxyprop-2-yl | |
| 41 | CN | Methylthiomethyl | |
| 42 | CN | tert.-Butylthiomethyl | |
| 43 | CN | 2-Methylthioprop-2-yl | oil; IR (film): 1436, 1191, 1131, 1114, 1016, 998 |
| 44 | CN | 2-iso-Propylthioprop-2-yl | |
| 45 | CN | 2-tert.-Butylthioprop-2-yl | oil; IR (film): 1366, 1191, 1132, 1113, 1012, 1000 |
| 46 | CN | Methyl | |
| 47 | CN | Ethyl | |
| 48 | CN | n-Propyl | |
| 49 | CN | iso-Propyl | oil; IR (film): 1285, 1258, 1189, 1131, 1111, 1069, 1008 |
| 50 | CN | n-Butyl | |
| 51 | CN | iso-Butyl | |
| 52 | CN | sec.-Butyl | |
| 53 | CN | tert.-Butyl | |
| 54 | CN | n-Hexyl | |
| 55 | CN | n-Decyl | |
| 56 | CN | Cyclopropyl | oil; IR (film): 1207, 1190, 1130, 1057, 1003 |
| 57 | CN | Cyclohexyl | |
| 58 | CN | Phenylthiomethyl | |
| 59 | CN | 2-Phenylthiomethyl | |
| 60 | CN | 2-(2'-Chlorophenylthio)prop-2-yl | |
| 61 | CN | Ethynyl | |
| 62 | CN | 1-Propynyl | |
| 63 | CN | Methoxy | |
| 64 | CN | Ethoxy | |
| 65 | CN | n-Propoxy | |
| 66 | CN | iso-Propoxy | |
| 67 | CN | n-Butoxy | |
| 68 | CN | iso-Butoxy | |
| 69 | CN | sec.-Butoxy | |
| 70 | CN | tert.-Butoxy | |
| 71 | CN | Methylthio | |

TABLE I-continued

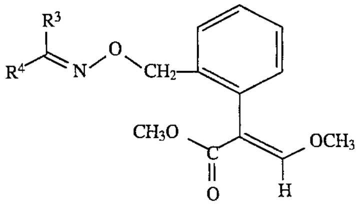

| No. | $R^3$ | $R^4$ | Data |
|---|---|---|---|
| 72 | CN | Ethylthio | |
| 73 | CN | n-Propylthio | |
| 74 | CN | iso-Propylthio | |
| 75 | CN | n-Butylthio | |
| 76 | CN | iso-Butylthio | |
| 77 | CN | sec.-Butylthio | |
| 78 | CN | tert.-Butylthio | |
| 79 | CN | Benzylthio | |
| 80 | CN | Trifluoromethoxy | |
| 81 | CN | Cyano | |
| 82 | CN | Amino | |
| 83 | CN | Methylamino | |
| 84 | CN | Dimethylamino | |
| 85 | CN | Ethylamino | |
| 86 | CN | Diethylamino | |
| 87 | CN | Di-n-Propylamino | |
| 88 | CN | Di-iso-Propylamino | |
| 89 | CN | Di-n-Butylamino | |
| 90 | CN | Di-iso-Butylamino | |
| 91 | CN | Acetyl | |
| 92 | CN | Propion-1-yl | |
| 93 | CN | Butyr-1-yl | |
| 94 | CN | iso-Butyr-1-yl | |
| 95 | CN | Pivaloyl | |
| 96 | CN | Benzoyl | |
| 97 | CN | 4-Chlorobenzoyl | |
| 98 | CN | Benzylcarbonyl | |
| 99 | CN | Methoxycarbonyl | |
| 100 | CN | Ethoxycarbonyl | |
| 101 | CN | n-Propoxycarbonyl | |
| 102 | CN | iso-Propoxycarbonyl | |
| 103 | CN | n-Butoxycarbonyl | |
| 104 | CN | iso-Butoxycarbonyl | |
| 105 | CN | sec.-Butoxycarbonyl | |
| 106 | CN | tert.-Butoxycarbonyl | |
| 107 | CN | n-Hexoxycarbonyl | |
| 108 | CN | Phenoxycarbonyl | |
| 109 | CN | 4-Chlorophenoxycarbonyl | |
| 110 | CN | Benzyloxycarbonyl | |
| 111 | CN | Aminocarbonyl | |
| 112 | CN | Dimethylaminocarbonyl | |
| 113 | CN | Diethylaminocarbonyl | |
| 114 | CN | Di-iso-Propylaminocarbonyl | |
| 115 | CN | Phenylaminocarbonyl | |
| 116 | CN | N-Methyl-N-Phenylaminocarbonyl | |
| 117 | CN | Phenyl | oil; IR (film): 1245, 1127, 1024, 1015, 767, 750 |
| 118 | CN | 2-Fluorophenyl | |
| 119 | CN | 3-Fluorophenyl | |
| 120 | CN | 4-Fluorophenyl | |
| 121 | CN | Pentafluorophenyl | |
| 122 | CN | 2-Chlorophenyl | |
| 123 | CN | 3-Chlorophenyl | |
| 124 | CN | 4-Chlorophenyl | |
| 125 | CN | Pentachlorophenyl | |
| 126 | CN | 2,3-Dichlorophenyl | |
| 127 | CN | 2,4-Dichlorophenyl | |
| 128 | CN | 2,5-Dichlorophenyl | |
| 129 | CN | 2,6-Dichlorophenyl | |
| 130 | CN | 3,4-Dichlorophenyl | |
| 131 | CN | 3,5-Dichlorophenyl | |
| 132 | CN | 2,3,4-Trichlorophenyl | |
| 133 | CN | 2,3,5-Trichlorophenyl | |
| 134 | CN | 2,3,6-Trichlorophenyl | |
| 135 | CN | 2,4,5-Trichlorophenyl | |
| 136 | CN | 2,4,6-Trichlorophenyl | |
| 137 | CN | 3,4,5-Trichlorophenyl | |
| 138 | CN | 2,3,4,6-Tetrachlorophenyl | |

TABLE I-continued

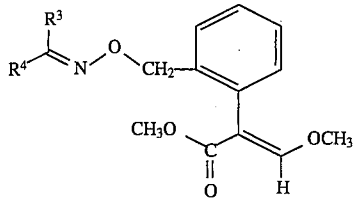

| No. | $R^3$ | $R^4$ | Data |
|---|---|---|---|
| 139 | CN | 2,3,5-6-Tetrachlorophenyl | |
| 140 | CN | 2-Bromophenyl | |
| 141 | CN | 3-Bromophenyl | |
| 142 | CN | 4-Bromophenyl | |
| 143 | CN | 2,4-Dibromophenyl | |
| 144 | CN | 3-Bromo-4-fluorophenyl | |
| 145 | CN | 3-Bromo-4-methoxyphenyl | |
| 146 | CN | 2-Iodophenyl | |
| 147 | CN | 3-Iodophenyl | |
| 148 | CN | 4-Iodophenyl | |
| 149 | CN | 2-Chloro-4-fluorophenyl | |
| 150 | CN | 2-Chloro-5-fluorophenyl | |
| 151 | CN | 2-Chloro-6-fluorophenyl | |
| 152 | CN | 2-Chloro-4-bromophenyl | |
| 153 | CN | 2-Bromo-4-chlorophenyl | |
| 154 | CN | 2-Bromo-4-fluorophenyl | |
| 155 | CN | 3-Bromo-4-chlorophenyl | |
| 156 | CN | 3-Chloro-4-fluorophenyl | |
| 157 | CN | 3-Fluoro-4-chlorophenyl | |
| 158 | CN | 2-Cyanophenyl | |
| 159 | CN | 3-Cyanophenyl | |
| 160 | CN | 4-Cyanophenyl | |
| 161 | CN | 2-Nitrophenyl | |
| 162 | CN | 3-Nitrophenyl | |
| 163 | CN | 4-Nitrophenyl | |
| 164 | CN | 2-Methylphenyl | |
| 165 | CN | 3-Methylphenyl | |
| 166 | CN | 4-Methylphenyl | |
| 167 | CN | 2,4-Dimethylphenyl | |
| 168 | CN | 2,6-Dimethylphenyl | |
| 169 | CN | 3,4-Dimethylphenyl | |
| 170 | CN | 3,5-Dimethylphenyl | |
| 171 | CN | 2,3,4-Trimethylphenyl | |
| 172 | CN | 2,3,5-Trimethylphenyl | |
| 173 | CN | 2,3,6-Trimethylphenyl | |
| 174 | CN | 2,4,5-Trimethylphenyl | |
| 175 | CN | 2,4,6-Trimethylphenyl | |
| 176 | CN | 3,4,5-Trimethylphenyl | |
| 177 | CN | Pentamethylphenyl | |
| 178 | CN | 2-Ethylphenyl | |
| 179 | CN | 3-Ethylphenyl | |
| 180 | CN | 4-Ethylphenyl | |
| 181 | CN | 3,5-Diethylphenyl | |
| 182 | CN | 2-n-Propylphenyl | |
| 183 | CN | 3-n-Propylphenyl | |
| 184 | CN | 4-n-Propylphenyl | |
| 185 | CN | 2-iso-Propylphenyl | |
| 186 | CN | 3-iso-Propylphenyl | |
| 187 | CN | 4-iso-Propylphenyl | |
| 188 | CN | 2,4-Di-iso-Propylphenyl | |
| 189 | CN | 3,5-Di-iso-Propylphenyl | |
| 190 | CN | 4-n-Butylphenyl | |
| 191 | CN | 4-sec.-Butylphenyl | |
| 192 | CN | 4-iso-Butylphenyl | |
| 193 | CN | 4-tert.-Butylphenyl | |
| 194 | CN | 3-tert.-Butylphenyl | |
| 195 | CN | 2-tert.-Butylphenyl | |
| 196 | CN | 2,4-Di-tert.-Butylphenyl | |
| 197 | CN | 3,5-Di-tert.-Butylphenyl | |
| 198 | CN | 4-n-Hexylphenyl | |
| 199 | CN | 4-n-Dodecylphenyl | |
| 200 | CN | 2-Methyl-4-tert.-Butylphenyl | |
| 201 | CN | 2-Methyl-6-tert.-Butylphenyl | |
| 202 | CN | 2-Methyl-4-iso-Propylphenyl | |
| 203 | CN | 2-Methyl-4-Cyclohexylphenyl | |
| 204 | CN | 2-Methyl-4-Phenylphenyl | |
| 205 | CN | 2-Methyl-4-Benzylphenyl | |

TABLE I-continued

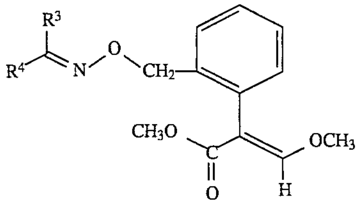

| No. | R³ | R⁴ | Data |
|---|---|---|---|
| 206 | CN | 2-Methyl-4-Phenoxyphenyl | |
| 207 | CN | 2-Methyl-4-Benzyloxyphenyl | |
| 208 | CN | 2-Methyl-3-Chlorophenyl | |
| 209 | CN | 2-Methyl-4-Chlorophenyl | |
| 210 | CN | 2-Methyl-5-Chlorophenyl | |
| 211 | CN | 2-Methyl-6-Chlorophenyl | |
| 212 | CN | 2-Methyl-4-Fluorophenyl | |
| 213 | CN | 2-Methyl-3-Bromophenyl | |
| 214 | CN | 2-Methyl-4-Bromophenyl | |
| 215 | CN | 2-Methyl-3-Methoxyphenyl | |
| 216 | CN | 2-Methyl-4-Methoxyphenyl | |
| 217 | CN | 2-Methyl-5-methoxyphenyl | |
| 218 | CN | 2-Methyl-6-methoxyphenyl | |
| 219 | CN | 2-Methyl-4-iso-Propoxyphenyl | |
| 220 | CN | 2-Methyl-2,5-dimethoxyphenyl | |
| 221 | CN | 2-Methoxyphenyl | |
| 222 | CN | 3-Methoxyphenyl | |
| 223 | CN | 4-Methoxyphenyl | |
| 224 | CN | 2,3-Dimethoxyphenyl | |
| 225 | CN | 2,4-Dimethoxyphenyl | |
| 226 | CN | 2,5-Dimethoxyphenyl | |
| 227 | CN | 2,6-Dimethoxyphenyl | |
| 228 | CN | 3,4-Dimethoxyphenyl | |
| 229 | CN | 3,5-Dimethoxyphenyl | |
| 230 | CN | 3,6-Dimethoxyphenyl | |
| 231 | CN | 2,3,4-Trimethoxyphenyl | |
| 232 | CN | 2,3,5-Trimethoxyphenyl | |
| 233 | CN | 2,3,6-Trimethoxyphenyl | |
| 234 | CN | 2,4,5-Trimethoxyphenyl | |
| 235 | CN | 2,4,6-Trimethoxyphenyl | |
| 236 | CN | 3,4,5-Trimethoxyphenyl | |
| 237 | CN | 2-Ethoxyphenyl | |
| 238 | CN | 3-Ethoxyphenyl | |
| 239 | CN | 4-Ethoxyphenyl | |
| 240 | CN | 2-iso-Propoxyphenyl | |
| 241 | CN | 3-iso-Propoxyphenyl | |
| 242 | CN | 4-iso-Propoxyphenyl | |
| 243 | CN | 3-tert.-Butoxyphenyl | |
| 244 | CN | 4-tert.-Butoxyphenyl | |
| 245 | CN | 2-Trifluoromethoxyphenyl | |
| 246 | CN | 3-Trifluoromethoxyphenyl | |
| 247 | CN | 4-Trifluoromethoxyphenyl | |
| 248 | CN | 3-(1',1',2',2'-Tetrafluoro)ethoxyphenyl | |
| 249 | CN | 4-(1',1',2',2'-Tetrafluoro)ethoxyphenyl | |
| 250 | CN | 2-Chloromethylphenyl | |
| 251 | CN | 3-Chloromethylphenyl | |
| 252 | CN | 4-Chloromethylphenyl | |
| 253 | CN | 2-Trifluoromethylphenyl | |
| 254 | CN | 3-Trifluoromethylphenyl | |
| 255 | CN | 4-Trifluoromethylphenyl | |
| 256 | CN | 2-(Methoxyiminomethyl)phenyl | |
| 257 | CN | 3-(Methoxyiminomethyl)phenyl | |
| 258 | CN | 4-(Methoxyiminomethyl)phenyl | |
| 259 | CN | 2-(Ethoxyiminomethyl)phenyl | |
| 260 | CN | 3-(Ethoxyiminomethyi)phenyl | |
| 261 | CN | 4-(Ethoxyiminomethyl)phenyl | |
| 262 | CN | 2-(n-Propoxyiminomethyl)phenyl | |
| 263 | CN | 3-(n-Propoxyiminomethyl)phenyl | |
| 264 | CN | 4-(n-Propoxyiminomethyl)phenyl | |
| 265 | CN | 2-(iso-Propoxyiminomethyl)phenyl | |
| 266 | CN | 3-(iso-Propoxyiminomethyl)phenyl | |
| 267 | CN | 4-(iso-Propoxylminomethyl)phenyl | |
| 268 | CN | 2-(n-Butoxyiminomethyl)phenyl | |
| 269 | CN | 3-(n-Butoxylminomethyl)phenyl | |
| 270 | CN | 4-(n-Butoxyiminomethyl)phenyl | |
| 271 | CN | 2-(iso-Butoxyiminomethyl)phenyl | |
| 272 | CN | 3-(iso-Butoxylminomethyl)phenyl | |

TABLE I-continued

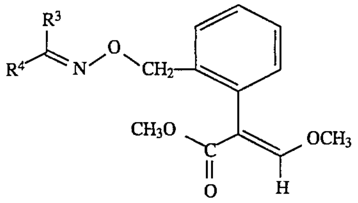

| No. | $R^3$ | $R^4$ | Data |
|---|---|---|---|
| 273 | CN | 4-(iso-Butoxyiminomethyl)phenyl | |
| 274 | CN | 2-(tert.-Butoxyiminomethyl)phenyl | |
| 275 | CN | 3-(tert.-Butoxylminomethyl)phenyl | |
| 276 | CN | 4-(tert.-Butoxylminomethyl)phenyl | |
| 277 | CN | 2-(n-Pentoxyiminomethyl)phenyl | |
| 279 | CN | 4-(n-Pentoxyiminomethyl)phenyl | |
| 280 | CN | 2-(n-Hexoxyiminomethyl)phenyl | |
| 281 | CN | 3-(n-Hexoxyiminomethyl)phenyl | |
| 282 | CN | 4-(n-Hexoxyiminomethyl)phenyl | |
| 283 | CN | 2-(Allyloxyiminomethyl)phenyl | |
| 284 | CN | 3-(Allyloxyiminomethyl)phenyl | |
| 285 | CN | 4-(Allyloxyiminomethyl)phenyl | |
| 286 | CN | 2-(Benzyloxyiminomethyl)phenyl | |
| 287 | CN | 3-(Benzyloxyiminomethyl)phenyl | |
| 288 | CN | 4-(Benzyloxyiminomethyl)phenyl | |
| 289 | CN | 2-(Methoxyimino-1'-ethyl)phenyl | |
| 290 | CN | 3-(Methoxyimino-1'-ethyl)phenyl | |
| 291 | CN | 4-(Methoxyimino-1'-ethyl)phenyl | |
| 292 | CN | 2-(Ethoxyimino-1'-ethyl)phenyl | |
| 293 | CN | 3-(Ethoxyimino-1'-ethyl)phenyl | |
| 294 | CN | 4-(Ethoxyimino-1'-ethyl)phenyl | |
| 295 | CN | 2-(n-Propoxyimino-1'-ethyl)phenyl | |
| 296 | CN | 3-(n-Propoxyimino-1'-ethyl)phenyl | |
| 297 | CN | 4-(n-Propoxyimino-1'-ethyl)phenyl | |
| 298 | CN | 2-(n-Butoxyamino-1'-ethyl)phenyl | |
| 299 | CN | 3-(n-Butoxyamino-1'-ethyl)phenyl | |
| 300 | CN | 4-(n-Butoxyamino-1'-ethyl)phenyl | |
| 301 | CN | 2-(n-Pentoxyimino-1'-ethyl)phenyl | |
| 302 | CN | 3-(n-Pentoxyimino-1'-ethyl)phenyl | |
| 303 | CN | 4-(n-Pentoxyimino-1'-ethyl)phenyl | |
| 304 | CN | 2-(n-Hexoxyimino-1'-ethyl)phenyl | |
| 305 | CN | 3-(n-Hexoxyimino-1'-ethyl)phenyl | |
| 306 | CN | 4-(n-Hexoxyimino-1'-ethyl)phenyl | |
| 307 | CN | 2-(Allyloxyimino-1'-ethyl)phenyl | |
| 308 | CN | 3-(Allyloxyimino-1'-ethyl)phenyl | |
| 309 | CN | 4-(Allyloxyimino-1'-ethyl)phenyl | |
| 310 | CN | 2-(Benzyloxyimino-1'-ethyl)phenyl | |
| 311 | CN | 3-(Benzyloxyimino-1'-ethyl)phenyl | |
| 312 | CN | 4-(Benzyloxyimino-1'-ethyl)phenyl | |
| 313 | CN | 2-Phenylphenyl | |
| 314 | CN | 3-Phenylphenyl | |
| 315 | CN | 4-Phenylphenyl | |
| 316 | CN | 2-Phenoxyphenyl | |
| 317 | CN | 3-Phenoxyphenyl | |
| 318 | CN | 4-Phenoxyphenyl | |
| 319 | CN | 2-Benzyloxyphenyl | |
| 320 | CN | 3-Benzyloxyphenyl | |
| 321 | CN | 4-Benzyloxyphenyl | |
| 322 | CN | 4-(Imidazol-1'-yl)phenyl | |
| 323 | CN | 4-(Piperazin-1'-yl)phenyl | |
| 324 | CN | 4-(Morpholin-1'-yl)phenyl | |
| 325 | CN | 4-(Piperidin-1'-yl)phenyl | |
| 326 | CN | 4-(Pyridyl-2'-oxy)phenyl | |
| 327 | CN | 2-Cyclopropylphenyl | |
| 328 | CN | 3-Cyclopropylphenyl | |
| 329 | CN | 4-Cyclopropylphenyl | |
| 330 | CN | 3-Cyclohexylphenyl | |
| 331 | CN | 4-Cyclohexylphenyl | |
| 332 | CN | 4-Oxiranylphenyl | |
| 333 | CN | 4-(1',3'-Dioxan-2'-yl)phenyl | |
| 334 | CN | 4-(Tetrahydropyran-2-yloxy)phenyl | |
| 335 | CN | 1-Naphthyl | |
| 336 | CN | 2-Naphthyl | |
| 337 | CN | 9-Anthryl | |
| 338 | CN | 1-Naphtoxy | |
| 339 | CN | 2-Naphtoxy | |
| 340 | CN | 9-Anthroxy | |

TABLE I-continued

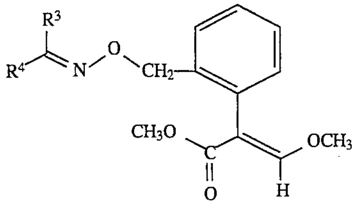

| No. | $R^3$ | $R^4$ | Data |
|---|---|---|---|
| 341 | CN | Phenoxy | |
| 342 | CN | 2-Chlorophenoxy | |
| 343 | CN | 3-Chlorophenoxy | |
| 344 | CN | 4-Chlorophenoxy | |
| 345 | CN | 4-Methylphenoxy | |
| 346 | CN | 4-tert.-Butylphenoxy | |
| 347 | CN | 4-Methoxyphenoxy | |
| 348 | CN | 4-Ethoxyphenoxy | |
| 349 | CN | 4-tert.-Butoxyphenoxy | |
| 350 | CN | Phenylthio | |
| 351 | CN | 2-Chlorophenylthio | |
| 352 | CN | 4-Chlorophenylthio | |
| 353 | CN | Benzyl | |
| 354 | CN | 2-Methylbenzyl | |
| 355 | CN | 3-Methylbenzyl | |
| 356 | CN | 4-Methylbenzyl | |
| 357 | CN | 4-tert.-Butylbenzyl | |
| 358 | CN | 2-Chlorobenzyl | |
| 359 | CN | 3-Chlorobenzyl | |
| 360 | CN | 4-Chlorobenzyl | |
| 361 | CN | 2,4-Dichlorobenzyl | |
| 362 | CN | 2,6-Dichiorobenzyl | |
| 363 | CN | 2,4,6-Trichlorobenzyl | |
| 364 | CN | 2-Trifluoromethylbenzyl | |
| 365 | CN | 3-Trifluoromethylbenzyl | |
| 366 | CN | 4-Trifluoromethylbenzyl | |
| 367 | CN | 2-Methoxybenzyl | |
| 368 | CN | 4-Methoxybenzyl | |
| 369 | CN | 4-tert.-Butoxybenzyl | |
| 370 | CN | 4-Phenoxybenzyl | |
| 371 | CN | 1-Phenethyl | |
| 372 | CN | 2-Phenethyl | |
| 373 | CN | 1-Phenylpropyl | |
| 374 | CN | 2-Phenylpropyl | |
| 375 | CN | 3-Phenylpropyl | |
| 376 | CN | 2-Methyl-2-phenylpropyl | |
| 377 | CN | 2-methyl-3-phenylpropyl | |
| 378 | CN | 4-Phenylbutyl | |
| 379 | CN | 2-Phenyl-1-ethenyl | |
| 380 | CN | 1-Phenyl-1-ethenyl | |
| 381 | CN | 1-Phenyl-1-propenyl | |
| 382 | CN | 1-Phenyl-1-propen-2-yl | |
| 383 | CN | 2,2-Diphenylethenyl | |
| 384 | CN | Phenoxymethyl | |
| 385 | CN | 2-Pyridyl | |
| 386 | CN | 3-Pyridyl | |
| 387 | CN | 4-Pyridyl | |
| 388 | CN | 2,6-Pyrimidinyl | |
| 389 | CN | 1,5-Pyrimidinyl | |
| 390 | CN | 2-Thienyl | |
| 391 | CN | 3-Thienyl | |
| 392 | CN | 2-Furyl | |
| 393 | CN | 3-Furyl | |
| 394 | CN | 1-Pyrrolyl | |
| 395 | CN | 1-Imidazolyl | |
| 396 | CN | 1,2,4-Triazolyl | |
| 397 | CN | 1,3,4-Triazolyl | |
| 398 | CN | 4-Thiazolyl | |
| 399 | CN | 2-Benzothiazolyl | |
| 400 | CN | 2-Pyridyloxy | |
| 401 | CN | 2-Pyrimidinyloxy | |
| 402 | CN | 2-Pyridylthio | |
| 403 | CN | 2-Pyrimidinylthio | |
| 404 | CN | 2-Benzothiazolylthio | |
| 405 | CN | Phenylthiomethyl | |
| 406 | CN | 2-Pyridylmethyl | |
| 407 | CN | 3-Pyridylmethyl | |

TABLE I-continued

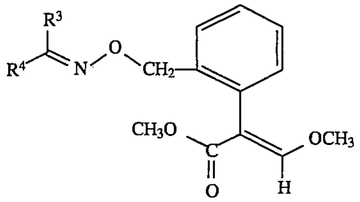

| No. | $R^3$ | $R^4$ | Data |
|---|---|---|---|
| 408 | CN | Furfuryloxy | |
| 409 | CN | Thienylmethoxy | |
| 410 | CN | 3-Isoxazolylmethoxy | |
| 411 | CN | 2-Oxazolylmethoxy | |
| 412 | CN | 2-Pyridylmethoxy | |
| 413 | CN | 2'-Furyl-2-ethenyl | |
| 414 | CN | 2'-Thienyl-2-ethenyl | |
| 415 | CN | 3'-Pyridyl-2-ethenyl | |
| 416 | CN | Oxiranyl | |
| 417 | CN | 1-Aziridinyl | |
| 418 | CN | 1-Azetidinyl | |
| 419 | CN | 1-Pyrrolidinyl | |
| 420 | CN | 2-Tetrahydrofuryl | |
| 421 | CN | 2-Tetrahydropyranyl | |
| 422 | CN | 3-Tetrahydropyranyl | |
| 423 | CN | 1-Piperidinyl | |
| 424 | CN | 1-Morpholinyl | |
| 425 | CN | 1-Piperazinyl | |
| 426 | CN | 1,3-Dioxan-2-yl | |
| 427 | CN | 3-Tetrahydrothiopyranyl | |
| 428 | CN | 2-Dihydropyranytoxy | |
| 429 | CN | 2-Tetrahydropyranytoxy | oil; IR (film): 12051131, 1087, 1047, 1004 |
| 430 | CN | $(CH_2)_4$ | |
| 431 | CN | $(CH_2)_5$ | |
| 432 | CN | $(CH_2)_6$ | |
| 433 | CN | | |
| 434 | CN | | |
| 435 | CN | 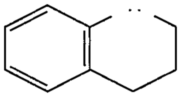 | |
| 436 | CN | 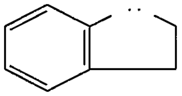 | |
| 437 | CN | 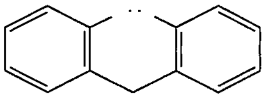 | |
| 438 | CN | 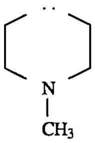 | |
| 439 | CN | 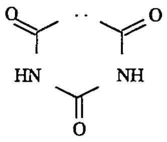 | |
| 440 | CN | 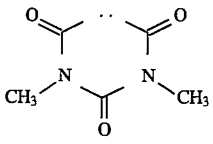 | |
| 441 | CN | $CF_3$ | |

TABLE I-continued

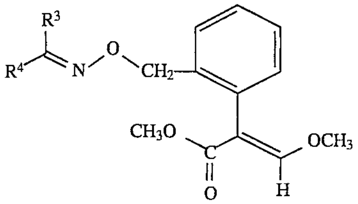

| No. | $R^3$ | $R^4$ | Data |
|---|---|---|---|
| 442 | CN | 2-Fluoroethyl | |
| 443 | CN | 2,2,2-Trifluoroethyl | |
| 444 | CN | Pentafluoroethyl | |
| 445 | CN | Chloromethyl | |
| 446 | CN | Dichloromethyl | |
| 447 | CN | Trichloromethyl | |
| 448 | CN | 2-Chloroethyl | |
| 449 | CN | 2,2,2-Trichloroethyl | |
| 450 | CN | Pentachloroethyl | |
| 451 | CN | Cyclopropyl | |
| 452 | CN | Cyclobutyl | |
| 453 | CN | Cyclopentyl | |
| 454 | CN | Cyclohexyl | |
| 455 | CN | 1-Methylcyclopropyl | |
| 456 | CN | 2,2-Dimethylcyclopropyl | |
| 457 | CN | 1-Methylcyclohexyl | |
| 458 | CN | 2,2-Difluorocyclopropyl | |
| 459 | CN | 2,2-Dichlorocyclopropyl | |
| 460 | CN | 2,2-Dibromocyclopropyl | |
| 461 | CN | 2,2-Dichloro-3-methylcyclopropyl | |
| 462 | CN | 2,2,3,3-Tetrafluorocyclobutyl | |
| 463 | CN | Ethenyl | |
| 464 | CN | 1-Propenyl | |
| 465 | CN | 2-Methyl-1-propenyl | |
| 466 | CN | 4-Methylpent-3-en-1-yl | |
| 467 | CN | 2-Propenyl | |
| 468 | CN | 2-Butenyl | |
| 469 | CN | 1-Methyl-2-propenyl | |
| 470 | CN | 3-Methyl-2-butenyl | |
| 471 | CN | 2,2-Difluoroethenyl | |
| 472 | CN | 2,2-Dichloroethenyl | |
| 473 | CN | 3,3,3-Trifluoropropenyl | |
| 474 | CN | 3,3,3-Trichloropropenyl | |
| 475 | CN | 3-Chloro-2-propenyl | |
| 476 | CN | Cyclopent-1-enyl | |
| 477 | CN | Cyclopentadienyl | |
| 478 | CN | Cyclohex-1-enyl | |
| 479 | CN | Pentafluorocyclopentadienyl | |
| 480 | CN | Pentachlorocyclopentadienyl | |
| 481 | CN | Styryl | |
| 482 | $CH_3$ | Methoxymethyl | |
| 483 | $CH_3$ | Ethoxymethyl | |
| 484 | $CH_3$ | n-Propoxymethyl | |
| 485 | $CH_3$ | iso-Propoxymethyl | |
| 486 | $CH_3$ | tert.-Butoxymethyl | |
| 487 | $CH_3$ | 2-Methoxyprop-2-yl | |
| 488 | $CH_3$ | 2-Ethoxyprop-2-yl | |
| 489 | $CH_3$ | 2-n-Propoxyprop-2-yl | |
| 490 | $CH_3$ | 2-iso-Propoxyprop-2-yl | |
| 491 | $CH_3$ | 2-tert.-Butoxyprop-2-yl | |
| 492 | $CH_3$ | Methylthiomethyl | |
| 493 | $CH_3$ | tert.-Butylthiomethyl | |
| 494 | $CH_3$ | 2-Methylthioprop-2-yl | |
| 495 | $CH_3$ | 2-iso-Propylthioprop-2-yl | |
| 496 | $CH_3$ | 2-tert.-Butylthioprop-2-yl | |
| 497 | $CH_3$ | Methyl | |
| 498 | $CH_3$ | Ethyl | |
| 499 | $CH_3$ | n-Propyl | |
| 500 | $CH_3$ | iso-Propyl | |
| 501 | $CH_3$ | n-Butyl | |
| 502 | $CH_3$ | iso-Butyl | |
| 503 | $CH_3$ | sec.-Butyl | |
| 504 | $CH_3$ | tert.-Butyl | |
| 505 | $CH_3$ | n-Hexyl | |
| 506 | $CH_3$ | n-Decyl | |
| 507 | $CH_3$ | Cyclopropyl | |
| 508 | $CH_3$ | Cyclohexyl | |

TABLE I-continued

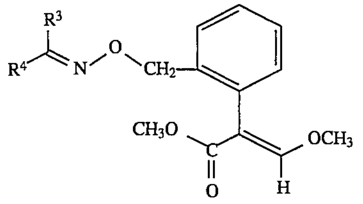

| No. | $R^3$ | $R^4$ | Data |
|---|---|---|---|
| 509 | $CH_3$ | Phenylthiomethyl | |
| 510 | $CH_3$ | 2-Phenylthiomethyl | |
| 511 | $CH_3$ | 2-(2'-Chlorophenylthio)prop-2-yl | |
| 512 | $CH_3$ | Ethynyl | |
| 513 | $CH_3$ | 1-Propynyl | |
| 514 | $CH_3$ | Methoxy | |
| 515 | $CH_3$ | Ethoxy | |
| 516 | $CH_3$ | n-Propoxy | |
| 517 | $CH_3$ | iso-Propoxy | |
| 518 | $CH_3$ | n-Butoxy | |
| 519 | $CH_3$ | iso-Butoxy | |
| 520 | $CH_3$ | sec.-Butoxy | |
| 521 | $CH_3$ | tert.-Butoxy | |
| 522 | $CH_3$ | methylthio | |
| 523 | $CH_3$ | Ethylthio | |
| 524 | $CH_3$ | n-Propylthio | |
| 525 | $CH_3$ | iso-Propylthio | |
| 526 | $CH_3$ | n-Butylthio | |
| 527 | $CH_3$ | iso-Butylthio | |
| 528 | $CH_3$ | sec.-Butylthio | |
| 529 | $CH_3$ | tert.-Butylthio | |
| 530 | $CH_3$ | Benzylthio | |
| 531 | $CH_3$ | Trifluoromethoxy | |
| 532 | $CH_3$ | Cyano | |
| 533 | $CH_3$ | Amino | |
| 534 | $CH_3$ | Methylamino | |
| 535 | $CH_3$ | Dimethylamino | |
| 536 | $CH_3$ | Ethylamino | |
| 537 | $CH_3$ | Diethylamino | |
| 538 | $CH_3$ | Di-n-Propylamino | |
| 539 | $CH_3$ | Di-iso-Propylamino | |
| 540 | $CH_3$ | Di-n-Butylamino | |
| 541 | $CH_3$ | Di-iso-Butylamino | |
| 542 | $CH_3$ | Acetyl | |
| 543 | $CH_3$ | Propion-1-yl | |
| 544 | $CH_3$ | Butyr-1-yl | |
| 545 | $CH_3$ | iso-Butyr-1-yl | |
| 546 | $CH_3$ | Pivaloyl | |
| 547 | $CH_3$ | Benzoyl | |
| 548 | $CH_3$ | 4-Chlorobenzoyl | |
| 549 | $CH_3$ | Benzylcarbonyl | |
| 550 | $CH_3$ | Methoxycarbonyl | |
| 551 | $CH_3$ | Ethoxycarbonyl | |
| 552 | $CH_3$ | n-Propoxycarbonyl | |
| 553 | $CH_3$ | iso-Propoxycarbonyl | |
| 554 | $CH_3$ | n-Butoxycarbonyl | |
| 555 | $CH_3$ | iso-Butoxycarbonyl | |
| 556 | $CH_3$ | sec.-Butoxycarbonyl | |
| 557 | $CH_3$ | tert.-Butoxycarbonyl | |
| 558 | $CH_3$ | n-Hexoxycarbonyl | |
| 559 | $CH_3$ | Phenoxycarbonyl | |
| 560 | $CH_3$ | 4-Chlorophenoxycarbonyl | |
| 561 | $CH_3$ | Benzyloxycarbonyl | |
| 562 | $CH_3$ | Aminocarbonyl | |
| 563 | $CH_3$ | Dimethylaminocarbonyl | |
| 564 | $CH_3$ | Diethylaminocarbonyl | |
| 565 | $CH_3$ | Di-iso-Propylaminocarbonyl | |
| 566 | $CH_3$ | Phenylaminocarbonyl | |
| 567 | $CH_3$ | N-Methyl-N-Phenylaminocarbonyl | |
| 568 | $CH_3$ | Phenyl | |
| 569 | $CH_3$ | 2-Fluorophenyl | oil; IR (film): 1708, 1634, 1257, 1129, 761 |
| 570 | $CH_3$ | 3-Fluorophenyl | |
| 571 | $CH_3$ | 4-Fluorophenyl | m.p.: 67–68° C.; |
| 572 | $CH_3$ | Pentafluorophenyl | |
| 573 | $CH_3$ | 2-Chlorophenyl | oil.: — |
| 574 | $CH_3$ | 3-Chlorophenyl | |
| 575 | $CH_3$ | 4-Chlorophenyl | |

TABLE I-continued

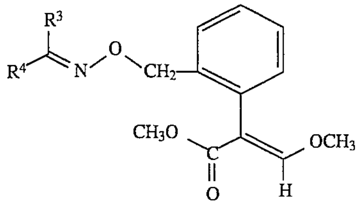

| No. | $R^3$ | $R^4$ | Data |
|---|---|---|---|
| 576 | $CH_3$ | Pentachlorophenyl | |
| 577 | $CH_3$ | 2,3-Dichlorophenyl | |
| 578 | $CH_3$ | 2,4-Dichlorophenyl | oil; IR (film): 1708, 1634, 1256, 1129 |
| 579 | $CH_3$ | 2,5-Dichlorophenyl | m.p.: 80–2° C.;<br>IR; (KBr): 1704, 1634, 1250, 1132, 934, 766 |
| 580 | $CH_3$ | 2,6-Dichlorophenyl | |
| 581 | $CH_3$ | 3,4-Dichlorophenyl | |
| 582 | $CH_3$ | 3,5-Dichlorophenyl | m.p.: 87–88° C.;<br>IR (KBr): 1699, 1303, 1071, 1015, 932, 835 |
| 583 | $CH_3$ | 2,3,4-Trichlorophenyl | oil; IR (film): 1709, 1627, 1257, 1131, 1109 |
| 584 | $CH_3$ | 2,3,5-Trichlorophenyl | |
| 585 | $CH_3$ | 2,3,6-Trichlorophenyl | |
| 586 | $CH_3$ | 2,4,5-Trichlorophenyl | |
| 587 | $CH_3$ | 2,4,6-Trichlorophenyl | |
| 588 | $CH_3$ | 3,4,5-Trichlorophenyl | |
| 589 | $CH_3$ | 2,3,4,6-Tetrachlorophenyl | |
| 590 | $CH_3$ | 2,3,5,6-Tetrachlorophenyl | |
| 591 | $CH_3$ | 2-Bromophenyl | |
| 592 | $CH_3$ | 3-Bromophenyl | m.p.: 60–2° C.;<br>IR (KBr): 1708, 1635, 1253, 1129, 1113, 933, 773 |
| 593 | $CH_3$ | 4-Bromophenyl | m.p.: 104–6° C.;<br>IR (KBr): 1694, 1620, 1296, 1264, 1035, 938 |
| 594 | $CH_3$ | 2,4-Dibromophenyl | |
| 595 | $CH_3$ | 3-Bromo-4-Fluorophenyl | |
| 596 | $CH_3$ | 3-Bromo-4-Methoxyphenyl | |
| 597 | $CH_3$ | 2-iodophenyl | |
| 598 | $CH_3$ | 3-iodophenyl | |
| 599 | $CH_3$ | 4-iodophenyl | |
| 600 | $CH_3$ | 2-Chloro-4-fluorophenyl | |
| 601 | $CH_3$ | 2-Chloro-5-fluorophenyl | |
| 602 | $CH_3$ | 2-Chloro-6-fluorophenyl | |
| 603 | $CH_3$ | 2-Chloro-4-bromophenyl | |
| 604 | $CH_3$ | 2-Bromo-4-chlorophenyl | |
| 605 | $CH_3$ | 2-Bromo-4-fluorophenyl | |
| 606 | $CH_3$ | 3-Bromo-4-chlorophenyl | |
| 607 | $CH_3$ | 3-Chloro-4-fluorophenyl | |
| 608 | $CH_3$ | 3-Fluoro-4-chlorophenyl | |
| 609 | $CH_3$ | 2-Cyanophenyl | |
| 610 | $CH_3$ | 3-Cyanophenyl | |
| 611 | $CH_3$ | 4-Cyanophenyl | |
| 612 | $CH_3$ | 2-Nitrophenyl | |
| 613 | $CH_3$ | 3-Nitrophenyl | |
| 614 | $CH_3$ | 4-Nitrophenyl | |
| 615 | $CH_3$ | 2-Methylphenyl | |
| 616 | $CH_3$ | 3-Methylphenyl | oil; IR (film): 1709, 1634, 1256, 1129 |
| 617 | $CH_3$ | 4-Methylphenyl | m.p.: 73–75° C.;<br>IR (KBr): 1696, 1625, 1262, 1127, 1037, 930 |
| 618 | $CH_3$ | 2,4-Dimethylphenyl | |
| 619 | $CH_3$ | 2,6-Dimethylphenyl | |
| 620 | $CH_3$ | 3,4-Dimethylphenyl | |
| 621 | $CH_3$ | 3,5-Dimethylphenyl | |
| 622 | $CH_3$ | 2,3,4-Trimethylphenyl | |
| 623 | $CH_3$ | 2,3,5-Trimethylphenyl | |
| 624 | $CH_3$ | 2,3,6-Trimethylphenyl | |
| 625 | $CH_3$ | 2,4,5-Trimethylphenyl | |
| 626 | $CH_3$ | 2,4,6-Trimethylphenyl | |
| 627 | $CH_3$ | 3,4,5-Trimethylphenyl | |
| 628 | $CH_3$ | Pentamethylphenyl | |
| 629 | $CH_3$ | 2-Ethylphenyl | |
| 630 | $CH_3$ | 3-Ethylphenyl | |
| 631 | $CH_3$ | 4-Ethylphenyl | |
| 632 | $CH_3$ | 3,5-Diethylphenyl | |
| 633 | $CH_3$ | 2-n-Propylphenyl | |
| 634 | $CH_3$ | 3-n-Propylphenyl | |
| 635 | $CH_3$ | 4-n-Propylphenyl | |
| 636 | $CH_3$ | 2-iso-Propylphenyl | |
| 637 | $CH_3$ | 3-iso-Propylphenyl | |

TABLE I-continued

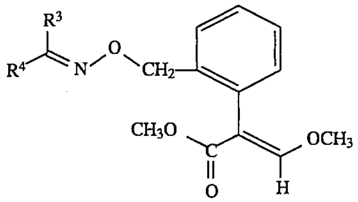

| No. | $R^3$ | $R^4$ | Data |
|---|---|---|---|
| 638 | $CH_3$ | 4-iso-Propylphenyl | |
| 639 | $CH_3$ | 2,4-Di-iso-Propylphenyl | |
| 640 | $CH_3$ | 3,5-Di-iso-Propylphenyl | |
| 641 | $CH_3$ | 4-n-Butylphenyl | |
| 642 | $CH_3$ | 4-sec.-Butylphenyl | |
| 643 | $CH_3$ | 4-iso-Butylphenyl | |
| 644 | $CH_3$ | 4-tert.-Butylphenyl | |
| 645 | $CH_3$ | 3-tert.-Butylphenyl | |
| 646 | $CH_3$ | 2-tert.-Butylphenyl | |
| 647 | $CH_3$ | 2,4-Di-tert.-Butylphenyl | |
| 648 | $CH_3$ | 3,5-Di-tert.-Butylphenyl | |
| 649 | $CH_3$ | 4-n-Hexylphenyl | |
| 650 | $CH_3$ | 4-n-Dodecylphenyl | |
| 651 | $CH_3$ | 2-Methyl-4-tert.-Butylphenyl | |
| 652 | $CH_3$ | 2-Methyl-6-tert.-Butylphenyl | |
| 653 | $CH_3$ | 2-Methyl-4-iso-Propylphenyl | |
| 654 | $CH_3$ | 2-Methyl-4-Cyclohexylphenyl | |
| 655 | $CH_3$ | 2-Methyl-4-Phenylphenyl | |
| 656 | $CH_3$ | 2-Methyl-4-Benzylphenyl | |
| 657 | $CH_3$ | 2-Methyl-4-Phenoxyphenyl | |
| 658 | $CH_3$ | 2-Methyl-4-Benzyloxyphenyl | |
| 659 | $CH_3$ | 2-Methyl-3-Chlorophenyl | |
| 660 | $CH_3$ | 2-Methyl-4-Chlorophenyl | |
| 661 | $CH_3$ | 2-Methyl-5-Chlorophenyl | |
| 662 | $CH_3$ | 2-Methyl-6-Chlorophenyl | |
| 663 | $CH_3$ | 2-Methyl-4-Fluorophenyl | |
| 664 | $CH_3$ | 2-Methyl-3-Bromophenyl | |
| 665 | $CH_3$ | 2-Methyl-4-Bromophenyl | |
| 666 | $CH_3$ | 2-Methyl-3-Methoxyphenyl | |
| 667 | $CH_3$ | 2-Methyl-4-Methoxyphenyl | |
| 668 | $CH_3$ | 2-Methyl-5-Methoxyphenyl | |
| 669 | $CH_3$ | 2-Methyl-6-Methoxyphenyl | |
| 670 | $CH_3$ | 2-Methyl-4-iso-Propoxyphenyl | |
| 671 | $CH_3$ | 2-Methyl-2,5-Dimethoxyphenyl | |
| 672 | $CH_3$ | 2-Methoxyphenyl | |
| 673 | $CH_3$ | 3-Methoxyphenyl | oil; IR (film): 1708, 1634, 1285, 1256, 1129, 1111 |
| 674 | $CH_3$ | 4-Methoxyphenyl | oil; IR (film): 1708, 1253, 1129 |
| 675 | $CH_3$ | 2,3-Dimethoxyphenyl | |
| 676 | $CH_3$ | 2,4-Dimethoxyphenyl | |
| 677 | $CH_3$ | 2,5-Dimethoxyphenyl | |
| 678 | $CH_3$ | 2,6-Dimethoxyphenyl | |
| 679 | $CH_3$ | 3,4-Dimethoxyphenyl | |
| 680 | $CH_3$ | 3,5-Dimethoxyphenyl | |
| 681 | $CH_3$ | 3,6-Dimethoxyphenyl | |
| 682 | $CH_3$ | 2,3,4-Trimethoxyphenyl | |
| 683 | $CH_3$ | 2,3,5-Trimethoxyphenyl | |
| 684 | $CH_3$ | 2,3,6-Trimethoxyphenyl | |
| 685 | $CH_3$ | 2,4,5-Trimethoxyphenyl | |
| 686 | $CH_3$ | 2,4,6-Trimethoxyphenyl | |
| 687 | $CH_3$ | 3,4,5-Trimethoxyphenyl | |
| 688 | $CH_3$ | 2-Ethoxyphenyl | |
| 689 | $CH_3$ | 3-Ethoxyphenyl | |
| 690 | $CH_3$ | 4-Ethoxyphenyl | |
| 691 | $CH_3$ | 2-iso-Propoxyphenyl | |
| 692 | $CH_3$ | 3-iso-Propoxyphenyl | |
| 693 | $CH_3$ | 4-iso-Propoxyphenyl | |
| 694 | $CH_3$ | 3-tert.-Butoxyphenyl | |
| 695 | $CH_3$ | 4-tert.-Butoxyphenyl | |
| 696 | $CH_3$ | 2-Trifluoromethoxyphenyl | |
| 697 | $CH_3$ | 3-Trifluoromethoxyphenyl | |
| 698 | $CH_3$ | 4-Trifluoromethoxyphenyl | |
| 699 | $CH_3$ | 3-(1',1',2',2'-Tetrafluoro)ethoxyphenyl | |
| 700 | $CH_3$ | 4-(1',1',2',2'-Tetrafluoro)ethoxyphenyl | |
| 701 | $CH_3$ | 2-Chloromethylphenyl | |
| 702 | $CH_3$ | 3-Chloromethylphenyl | |
| 703 | $CH_3$ | 4-Chloromethylphenyl | |
| 704 | $CH_3$ | 2-Trifluoromethylphenyl | oil; IR (film): 1705, 1634, 1313, 1130, 1107, 767 |

TABLE I-continued

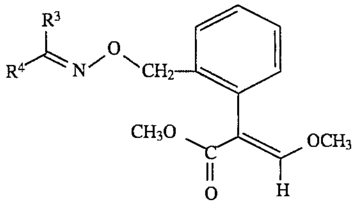

| No. | $R^3$ | $R^4$ | Data |
|---|---|---|---|
| 705 | $CH_3$ | 3-Trifluoromethylphenyl | oil; IR (film): 1710, 1635, 1276, 1128 |
| 706 | $CH_3$ | 4-Trifluoromethylphenyl | m.p.: 104–5° C.; IR (KBr): 1697, 1628, 1323, 1123 |
| 707 | $CH_3$ | 2-(Methoxyiminomethyl)phenyl | |
| 708 | $CH_3$ | 3-(Methoxyiminomethyl)phenyl | |
| 709 | $CH_3$ | 4-(Methoxyiminomethyl)phenyl | |
| 710 | $CH_3$ | 2-(Ethoxyiminomethyl)phenyl | |
| 711 | $CH_3$ | 3-(Ethoxyiminomethyl)phenyl | |
| 712 | $CH_3$ | 4-(Ethoxyiminomethyl)phenyl | |
| 713 | $CH_3$ | 2-(n-Propoxyiminomethyl)phenyl | |
| 714 | $CH_3$ | 3-(n-Propoxyiminomethyl)phenyl | |
| 715 | $CH_3$ | 4-(n-Propoxyiminomethyl)phenyl | |
| 716 | $CH_3$ | 2-(iso-Propoxyiminomethyl)phenyl | |
| 717 | $CH_3$ | 3-(iso-Propoxyiminomethyl)phenyl | |
| 718 | $CH_3$ | 4-(iso-Propoxyiminomethyl)phenyl | |
| 719 | $CH_3$ | 2-(n-Butoxyiminomethyl)phenyl | |
| 720 | $CH_3$ | 3-(n-Butoxyiminomethyl)phenyl | |
| 721 | $CH_3$ | 4-(n-Butoxyiminomethyl)phenyl | |
| 722 | $CH_3$ | 2-(iso-Butoxyiminomethyl)phenyl | |
| 723 | $CH_3$ | 3-(iso-Butoxyiminomethyl)phenyl | |
| 724 | $CH_3$ | 4-(iso-Butoxyiminomethyl)phenyl | |
| 725 | $CH_3$ | 2-(tert.-Butoxyiminomethyl)phenyl | |
| 726 | $CH_3$ | 3-(tert.-Butoxyiminomethyl)phenyl | |
| 727 | $CH_3$ | 4-(tert.-Butoxyiminomethyl)phenyl | |
| 728 | $CH_3$ | 2-(n-Pentoxyiminomethyl)phenyl | |
| 729 | $CH_3$ | 3-(n-Pentoxyiminomethyl)phenyl | |
| 730 | $CH_3$ | 4-(n-Pentoxyiminomethyl)phenyl | |
| 731 | $CH_3$ | 2-(n-Hexoxyiminomethyl)phenyl | |
| 732 | $CH_3$ | 3-(n-Hexoxyiminomethyl)phenyl | |
| 733 | $CH_3$ | 4-(n-Hexoxyiminomethyl)phenyl | |
| 734 | $CH_3$ | 2-(Allyloxyiminomethyl)phenyl | |
| 735 | $CH_3$ | 3-(Allyloxyiminomethyl)phenyl | |
| 736 | $CH_3$ | 4-(Allyloxyiminomethyl)phenyl | |
| 737 | $CH_3$ | 2-(Benzyloxyiminomethyl)phenyl | |
| 738 | $CH_3$ | 3-(Benzyloxyiminomethyl)phenyl | |
| 739 | $CH_3$ | 4-(Benzyloxyiminomethyl)phenyl | |
| 740 | $CH_3$ | 2-(Methoxyimino-1'-ethyl)phenyl | |
| 741 | $CH_3$ | 3-(Methoxyimino-1'-ethyl)phenyl | |
| 742 | $CH_3$ | 4-(Methoxyimino-1'-ethyl)phenyl | |
| 743 | $CH_3$ | 2-(Ethoxyimino-1'-ethyl)phenyl | |
| 744 | $CH_3$ | 3-(Ethoxyimino-1'-ethyl)phenyl | |
| 745 | $CH_3$ | 4-(Ethoxyimino-1'-ethyl)phenyl | |
| 746 | $CH_3$ | 2-(n-Propoxyimino-1'-ethyl)phenyl | |
| 747 | $CH_3$ | 3-(n-Propoxyimino-1'-ethyl)phenyl | |
| 748 | $CH_3$ | 4-(n-Propoxyimino-1'-ethyl)phenyl | |
| 749 | $CH_3$ | 2-(n-Butoxyamino-1'-ethyl)phenyl | |
| 750 | $CH_3$ | 3-(n-Butoxyamino-1'-ethyl)phenyl | |
| 751 | $CH_3$ | 4-(n-Butoxyamino-1'-ethyl)phenyl | |
| 752 | $CH_3$ | 2-(n-Pentoxyimino-1'-ethyl)phenyl | |
| 753 | $CH_3$ | 3-(n-Pentoxyimino-1'-ethyl)phenyl | |
| 754 | $CH_3$ | 4-(n-Pentoxyimino-1'-ethyl)phenyl | |
| 755 | $CH_3$ | 2-(n-Hexoxyimino-1'-ethyl)phenyl | |
| 756 | $CH_3$ | 3-(n-Hexoxyimino-1'-ethyl)phenyl | |
| 757 | $CH_3$ | 4-(n-Hexoxyimino-1'-ethyl)phenyl | |
| 758 | $CH_3$ | 2-(Allyloxyimino-1'-ethyl)phenyl | |
| 759 | $CH_3$ | 3-(Allyloxyimino-1'-ethyl)phenyl | |
| 760 | $CH_3$ | 4-(Allyloxyimino-1'-ethyl)phenyl | |
| 761 | $CH_3$ | 2-(Benzyloxyimino-1'-ethyl)phenyl | |
| 762 | $CH_3$ | 3-(Benzyloxyimino-1'-ethyl)phenyl | |
| 763 | $CH_3$ | 4-(Benzyloxyimino-1'-ethyl)phenyl | |
| 764 | $CH_3$ | 2-Phenylphenyl | |
| 765 | $CH_3$ | 3-Phenylphenyl | |
| 766 | $CH_3$ | 4-Phenylphenyl | |
| 767 | $CH_3$ | 2-Phenoxyphenyl | |
| 768 | $CH_3$ | 3-Phenoxyphenyl | |
| 769 | $CH_3$ | 4-Phenoxyphenyl | oil; IR (film): 1708, 1489, 1240, 1129 |
| 770 | $CH_3$ | 2-Benzyloxyphenyl | |

TABLE I-continued

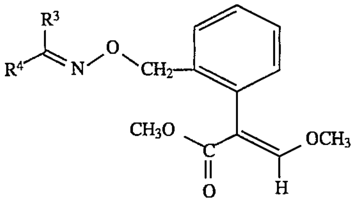

| No. | $R^3$ | $R^4$ | Data |
|---|---|---|---|
| 771 | $CH_3$ | 3-Benzyloxyphenyl | |
| 772 | $CH_3$ | 4-Benzyloxyphenyl | |
| 773 | $CH_3$ | 4-(Imidazol-1'-yl)phenyl | |
| 774 | $CH_3$ | 4-(Piperazin-1'-yl)phenyl | |
| 775 | $CH_3$ | 4-(Morpholin-1'-yl)phenyl | |
| 776 | $CH_3$ | 4-(Piperidin-1'-yl)phenyl | |
| 777 | $CH_3$ | 4-(Pyridyl-2'-oxy)phenyl | |
| 778 | $CH_3$ | 2-Cyclopropylphenyl | |
| 779 | $CH_3$ | 3-Cyclopropylphenyl | |
| 780 | $CH_3$ | 4-Cyclopropylphenyl | |
| 781 | $CH_3$ | 3-Cyclohexylphenyl | |
| 782 | $CH_3$ | 4-Cyclohexylphenyl | |
| 783 | $CH_3$ | 4-Oxiranylphenyl | |
| 784 | $CH_3$ | 4-(1',3'-Dioxan-2'-yl)phenyl | |
| 785 | $CH_3$ | 4-(Tetrahydropyran-2-yloxy)phenyl | |
| 786 | $CH_3$ | 1-Naphthyl | |
| 787 | $CH_3$ | 2-Naphthyl | |
| 788 | $CH_3$ | 9-Anthryl | |
| 789 | $CH_3$ | 1-Naphthoxy | |
| 790 | $CH_3$ | 2-Naphthoxy | |
| 791 | $CH_3$ | 9-Anthroxy | |
| 792 | $CH_3$ | Phenoxy | |
| 793 | $CH_3$ | 2-Chlorophenoxy | |
| 794 | $CH_3$ | 3-Chlorophenoxy | |
| 795 | $CH_3$ | 4-Chlorophenoxy | |
| 796 | $CH_3$ | 4-Methylphenoxy | |
| 797 | $CH_3$ | 4-tert.-Butylphenoxy | |
| 798 | $CH_3$ | 4-Methoxyphenoxy | |
| 799 | $CH_3$ | 4-Ethoxyphenoxy | |
| 800 | $CH_3$ | 4-tert.-Butoxyphenoxy | |
| 801 | $CH_3$ | Phenylthio | |
| 862 | $CH_3$ | 2-Chlorophenylthio | |
| 803 | $CH_3$ | 4-Chlorophenylthio | |
| 804 | $CH_3$ | Benzyl | |
| 805 | $CH_3$ | 2-Methylbenzyl | |
| 806 | $CH_3$ | 3-Methylbenzyl | |
| 807 | $CH_3$ | 4-Methylbenyzl | |
| 808 | $CH_3$ | 4-tert.-Butylbenzyl | |
| 809 | $CH_3$ | 2-Chlorobenzyl | |
| 810 | $CH_3$ | 3-Chlorobenzyl | |
| 811 | $CH_3$ | 4-Chlorobenzyl | |
| 812 | $CH_3$ | 2,4-Dichlorobenzyl | |
| 813 | $CH_3$ | 2,6-Dichlorobenzyl | |
| 814 | $CH_3$ | 2,4,6-Trichlorobenzyl | |
| 815 | $CH_3$ | 2-Trifluoromethylbenzyl | |
| 816 | $CH_3$ | 3-Trifluoromethylbenzyl | |
| 817 | $CH_3$ | 4-Trifluoromethylbenzyl | |
| 818 | $CH_3$ | 2-Methoxybenzyl | |
| 819 | $CH_3$ | 4-Methoxybenzyl | |
| 820 | $CH_3$ | 4-tert.-Butoxybenzyl | |
| 821 | $CH_3$ | 4-Phenoxybenzyl | |
| 822 | $CH_3$ | 1-Phenethyl | |
| 823 | $CH_3$ | 2-Phenethyl | |
| 824 | $CH_3$ | 1-Phenylpropyl | |
| 825 | $CH_3$ | 2-Phenylpropyl | |
| 826 | $CH_3$ | 3-Phenylpropyl | |
| 827 | $CH_3$ | 2-Methyl-2-phenylpropyl | |
| 828 | $CH_3$ | 2-Methyl-3-phenylpropyl | |
| 829 | $CH_3$ | 4-Phenylbutyl | |
| 830 | $CH_3$ | 2-Phenyl-1-ethenyl | |
| 831 | $CH_3$ | 1-Phenyl-1-ethenyl | |
| 832 | $CH_3$ | 1-Phenyl-1-propenyl | |
| 833 | $CH_3$ | 1-Phenyl-1-propen-2-yl | |
| 834 | $CH_3$ | 2,2-Diphenylethenyl | |
| 835 | $CH_3$ | Phenoxymethyl | |
| 836 | $CH_3$ | 2-Pyridyl | |
| 837 | $CH_3$ | 3-Pyridyl | |

TABLE I-continued

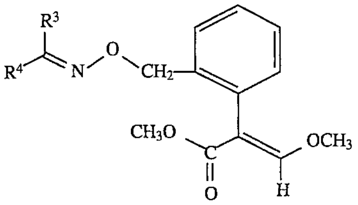

| No. | $R^3$ | $R^4$ | Data |
|---|---|---|---|
| 838 | $CH_3$ | 4-Pyridyl | |
| 839 | $CH_3$ | 2,6-Pyrimidinyl | |
| 840 | $CH_3$ | 1,5-Pyrimidinyl | |
| 841 | $CH_3$ | 2-Thienyl | |
| 842 | $CH_3$ | 3-Thienyl | |
| 843 | $CH_3$ | 2-Furyl | |
| 844 | $CH_3$ | 3-Furyl | |
| 845 | $CH_3$ | 1-Pyrrolyl | |
| 846 | $CH_3$ | 1-Imidazolyl | |
| 847 | $CH_3$ | 1,2,4-Triazolyl | |
| 848 | $CH_3$ | 1,3,4-Triazolyl | |
| 849 | $CH_3$ | 4-Thiazolyl | |
| 850 | $CH_3$ | 2-Benzothiazolyl | |
| 851 | $CH_3$ | 2-Pyridyloxy | |
| 852 | $CH_3$ | 2-Pyrimidinyloxy | |
| 853 | $CH_3$ | 2-Pyridylthio | |
| 854 | $CH_3$ | 2-Pyrimidinylthio | |
| 855 | $CH_3$ | 2-Benzothiazolylthio | |
| 856 | $CH_3$ | Phenylthiomethyl | |
| 857 | $CH_3$ | 2-Pyridylmethyl | |
| 858 | $CH_3$ | 3-Pyridylmethyl | |
| 859 | $CH_3$ | Furfuryloxy | |
| 860 | $CH_3$ | Thienylmethoxy | |
| 861 | $CH_3$ | 3-Isoxazolylmethoxy | |
| 862 | $CH_3$ | 2-Oxazolylmethoxy | |
| 863 | $CH_3$ | 2-Pyridylmethoxy | |
| 864 | $CH_3$ | 2'-Furyl-2-ethenyl | |
| 865 | $CH_3$ | 2'-Thienyl-2-ethenyl | |
| 866 | $CH_3$ | 3'-Pyridyl-2-ethenyl | |
| 867 | $CH_3$ | Oxiranyl | |
| 868 | $CH_3$ | 1-Aziridinyl | |
| 869 | $CH_3$ | 1-Azetidinyl | |
| 870 | $CH_3$ | 1-Pyrrolidinyl | |
| 871 | $CH_3$ | 2-Tetrahydrofuryl | |
| 872 | $CH_3$ | 2-Tetrahydropyranyl | |
| 873 | $CH_3$ | 3-Tetrahydropyranyl | |
| 874 | $CH_3$ | 1-Piperidinyl | |
| 875 | $CH_3$ | 1-Morpholinyl | |
| 076 | $CH_3$ | 1-Piperazinyl | |
| 877 | $CH_3$ | 1,3-Dioxan-2-yl | |
| 878 | $CH_3$ | 3-Tetrahydrothiopyranyl | |
| 879 | $CH_3$ | 2-Dihydropyranyloxy | |
| 880 | $CH_3$ | 2-Tetrahydropyranyloxy | |
| 881 | $CH_3$ | $CF_3$ | |
| 882 | $CH_3$ | 2-Fluoroethyl | |
| 883 | $CH_3$ | 2,2,2-Trifluoroethyl | |
| 884 | $CH_3$ | Pentafluoroethyl | |
| 885 | $CH_3$ | Chloromethyl | |
| 886 | $CH_3$ | Dichloromethyl | |
| 887 | $CH_3$ | Trichloromethyl | |
| 888 | $CH_3$ | 2-Chloroethyl | |
| 889 | $CH_3$ | 2,2,2-Trichloroethyl | |
| 890 | $CH_3$ | Pentachloroethyl | |
| 891 | $CH_3$ | Cyclopropyl | |
| 892 | $CH_3$ | Cyclobutyl | |
| 893 | $CH_3$ | Cyclopentyl | |
| 894 | $CH_3$ | Cyclohexyl | |
| 895 | $CH_3$ | 1-Methylcyclopropyl | |
| 896 | $CH_3$ | 2,2-Dimethylcyclopropyl | |
| 897 | $CH_3$ | 1-Methylcyclohexyl | |
| 898 | $CH_3$ | 2,2-Difluorocyclopropyl | |
| 899 | $CH_3$ | 2,2-Dichlorocyclopropyl | |
| 900 | $CH_3$ | 2,2-Dibromocyclopropyl | |
| 901 | $CH_3$ | 2,2-Dichloro-3-methylcyclopropyl | |
| 902 | $CH_3$ | 2,2,3,3-Tetrafluorocyclobutyl | |
| 903 | $CH_3$ | Ethenyl | |
| 904 | $CH_3$ | 1-Propenyl | |

TABLE I-continued

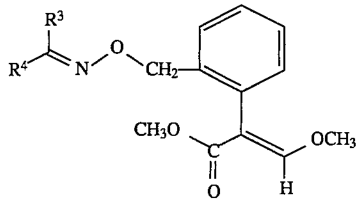

| No. | $R^3$ | $R^4$ | Data |
|---|---|---|---|
| 905 | $CH_3$ | 2-Methyl-1-propenyl | |
| 906 | $CH_3$ | 4-Methylpent-3-en-1-yl | |
| 907 | $CH_3$ | 2-Propenyl | |
| 908 | $CH_3$ | 2-Butenyl | |
| 909 | $CH_3$ | 1-Methyl-2-propenyl | |
| 910 | $CH_3$ | 3-Methyl-2-butenyl | |
| 911 | $CH_3$ | 2,2-Difluoroethenyl | |
| 912 | $CH_3$ | 2,2-Dichloroethenyl | |
| 913 | $CH_3$ | 3,3,3-Trifluoropropenyl | |
| 914 | $CH_3$ | 3,3,3-Trichloropropenyl | |
| 915 | $CH_3$ | 3-Chloro-2-propenyl | |
| 916 | $CH_3$ | Cyclopent-1-enyl | |
| 917 | $CH_3$ | Cyclopentadienyl | |
| 918 | $CH_3$ | Cyclohex-1-enyl | |
| 919 | $CH_3$ | Pentafluorocyclopentadienyl | |
| 920 | $CH_3$ | Pentachlorocyclopentadienyl | |
| 921 | Phenyl | Phenyl | |
| 922 | Phenyl | 2-Fluorophenyl | |
| 923 | Phenyl | 4-Fluorophenyl | |
| 924 | Phenyl | 2-Chlorophenyl | |
| 925 | Phenyl | 3-Chlorophenyl | |
| 926 | Phenyl | 4-Chlorophenyl | |
| 927 | Phenyl | 3,4-Dichlorophenyl | |
| 928 | Phenyl | 4-Nitrophenyl | |
| 929 | Phenyl | 2-$CF_3$-Phenyl | |
| 930 | Phenyl | 3-$CF_3$-Phenyl | |
| 931 | Phenyl | 4-$CF_3$-Phenyl | |
| 932 | Phenyl | 2-Methylphenyl | |
| 933 | Phenyl | 3-Methylphenyl | |
| 934 | Phenyl | 4-Methylphenyl | |
| 935 | Phenyl | 2,4-Dimethylphenyl | |
| 936 | Phenyl | 4-tert.-Butylphenyl | |
| 937 | Phenyl | 4-Methoxyphenyl | |
| 938 | 4-Fluorophenyl | 4-Fluorophenyl | |
| 939 | 2-Fluorophenyl | 4-Fluorophenyl | |
| 940 | 2-Chlorophenyl | 4-Fluorophenyl | |
| 941 | 2-Chlorophenyl | 2-Chlorophenyl | |
| 942 | 3-Chlorophenyl | 3-Chlorophenyl | |
| 943 | 4-Chlorophenyl | 4-Chlorophenyl | |
| 944 | 2-Chlorophenyl | 4-Chlorophenyl | |
| 945 | 4-Methoxyphenyl | 4-Methoxyphenyl | |
| 946 | 4-Dimethylaminophenyl | 4-Dimethylaminophenyl | |
| 947 | Phenyl | Naphthyl | |
| 948 | Ethyl | Ethyl | |
| 949 | Ethyl | n-Propyl | |
| 950 | Ethyl | iso-Propyl | |
| 951 | Ethyl | n-Butyl | |
| 952 | Ethyl | iso-Butyl | |
| 953 | Ethyl | 2-Methyl-butyl | |
| 954 | Ethyl | Benzyl | |
| 955 | n-Propyl | n-Propyl | |
| 956 | iso-Propyl | iso-Propyl | |
| 957 | n-Butyl | n-Butyl | |
| 958 | iso-Butyl | iso-Butyl | |
| 959 | tert.-Butyl | tert.-Butyl | |
| 960 | Benzyl | Benzyl | |
| 961 | Pentachloroethyl | Pentachloroethyl | |
| 962 | n-Hexyl | n-Hexyl | |
| 963 | Ethoxycarbonyl | Ethoxycarbonyl | |
| 964 | Phenyl | Benzoyl | |
| 965 | Ethyl | Phenyl | |
| 966 | n-Butyl | Phenyl | |
| 967 | Styryl | Styryl | |
| 968 | 2-Pyridyl | 2-Pyridyl | |
| 969 | 3-Pyridyl | 3-Pyridyl | |
| 970 | $CH_3$ | 3,5-Dibenzyloxyphenyl | IR (film): 1707, 1581, 1256, 1157, 1129 |

TABLE II

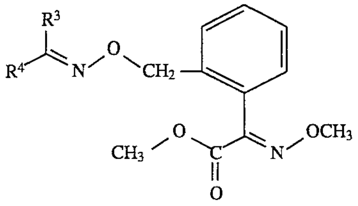

| No. | $R^3$ | $R^4$ | Data |
|---|---|---|---|
| 1 | Cl | Phenyl | |
| 2 | Cl | Cyano | |
| 3 | Cl | Ethoxycarbonyl | |
| 4 | Cl | Cyclopropyl | |
| 5 | $CF_3$ | $CF_3$ | |
| 6 | $CF_3$ | Phenyl | |
| 7 | $CCl_3$ | $CCl_3$ | |
| 8 | $CCl_3$ | Phenyl | |
| 9 | $CH_2Cl$ | Phenyl | |
| 10 | $CF_2CF_3$ | Phenyl | |
| 11 | $CF_2Cl$ | Phenyl | |
| 12 | $CHCl_2$ | Phenyl | |
| 13 | Cyclo-propyl | Cyclopropyl | |
| 14 | Cyclo-propyl | Phenyl | oil; IR (film): 1437 1321, 1219, 1045, 983, 766 |
| 15 | Cyclo-propyl | 4-Fluorophenyl | oil; IR (film): 1508, 1321, 1222, 1046, 985, 839 |
| 16 | Cyclo-propyl | 4-Chlorophenyl | oil; IR (film): 1489, 1321, 1218, 1090, 1046, 829 |
| 17 | Cyclo-propyl | 4-Methoxyphenyl | oil; IR (film): 1300, 1250, 1218, 983, 833 |
| 18 | Cyclo-propyl | 4-Ethoxyphenyl | |
| 19 | Cyclo-propyl | 4-Phenoxyphenyl | |
| 20 | Cyclo-propyl | Pentachlorophenyl | |
| 21 | Cyclo-propyl | Pentafluorophenyl | |
| 22 | Cyclo-pentyl | Phenyl | |
| 23 | Cyclo-hexyl | Phenyl | |
| 24 | Phenyl | 2,2-Dichloro-1-methyl-cyclopropyl | |
| 25 | Phenyl | 2,2-Difluorocyclo-propyl | |
| 26 | Phenyl | 2,2-Dichlorocyclo-propyl | |
| 27 | Phenyl | 2,2-Dibromocyclo-propyl | |
| 28 | Phenyl | 2,2,3,3-Tetrafluoro-cyclobutyl | |
| 29 | Phenyl | 2,2-Dimethylcyclo-propyl | |
| 30 | Phenyl | 1-Methylcyclohexyl | |
| 31 | CN | Methoxymethyl | |
| 32 | CN | Ethoxymethyl | |
| 33 | CN | n-Propoxymethyl | |
| 34 | CN | iso-Propoxymethyl | |
| 35 | CN | tert.-Butoxymethyl | |
| 36 | CN | 2-Methoxyprop-2-yl | m.p.: 83° C.; IR (KBr): 1437, 1223, 1206, 1069, 1006 |
| 37 | CN | 2-Ethoxyprop-2-yl | oil; IR (film): 1439, 3122, 1221, 1202, 1048 |
| 38 | CN | 2-n-Propoxyprop-2-yl | oil; IR (film): 1438, 1322, 1221, 1203, 1048 |
| 39 | CN | 2-iso-Propoxyprop-2-yl | m.p.: 74–5° C. |

TABLE II-continued

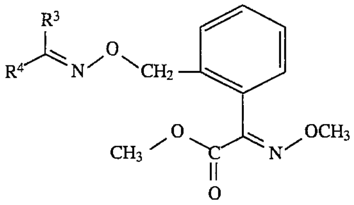

| No. | $R^3$ | $R^4$ | Data |
|---|---|---|---|
| | | | IR (KBr): 1302, 1231, 1169, 1108, 1079, 997, 757 |
| 40 | CN | 2-tert.-Butoxyprop-2-yl | |
| 41 | CN | Methylthiomethyl | |
| 42 | CN | tert.-Butylthiomethyl | |
| 43 | CN | 2-Methylthioprop-2-yl | m.p.: 107° C.; IR (KBr): 1434, 1297, 1126, 1066, 1010, 769 |
| 44 | CN | 2-iso-Propylthioprop-2-yl | oil; IR (film): 1438, 1366, 1321, 1221, 1202 |
| 45 | CN | 2-tert.-Butylthioprop-2-yl | |
| 46 | CN | Methyl | |
| 47 | CN | Ethyl | |
| 48 | CN | n-Propyl | |
| 49 | CN | iso-Propyl | oil; IR (film): 1439, 1321, 1222, 1012, 767 |
| 50 | CN | n-Butyl | |
| 51 | CN | iso-Butyl | |
| 52 | CN | sec.-Butyl | |
| 53 | CN | tert.-Butyl | |
| 54 | CN | n-Hexyl | |
| 55 | CN | n-Decyl | |
| 56 | CN | Cyclopropyl | m.p.: 74–75° C.; IR (KBr): 1433, 1223, 1043, 763 |
| 57 | CN | Cyclohexyl | |
| 58 | CN | Phenylthiomethyl | |
| 59 | CN | 2-Phenylthiomethyl | |
| 60 | CN | 2-(2'-Chlorophenyl-thio)prop-2-yl | |
| 61 | CN | Ethynyl | |
| 62 | CN | 1-Propynyl | |
| 63 | CN | Methoxy | |
| 64 | CN | Ethoxy | |
| 65 | CN | n-Propoxy | |
| 66 | CN | Iso-Propoxy | |
| 67 | CN | n-Butoxy | |
| 68 | CN | iso-Butoxy | |
| 69 | CN | sec.-Butoxy | |
| 70 | CN | tert.-Butoxy | |
| 71 | CN | Methylthio | |
| 72 | CN | Ethylthio | |
| 73 | CN | n-Propylthio | |
| 74 | CN | iso-Propylthio | |
| 75 | CN | n-Butylthio | |
| 76 | CN | iso-Butylthio | |
| 77 | CN | sec.-Butylthio | |
| 78 | CN | tert.-Butylthio | |
| 79 | CN | Benzylthio | |
| 80 | CN | Trifluoromethoxy | |
| 81 | CN | Cyano | |
| 82 | CN | Amino | |
| 83 | CN | Methylamino | |
| 84 | CN | Dimethylamino | |
| 85 | CN | Ethylamino | |
| 86 | CN | Diethylamino | |
| 87 | CN | Di-n-Propylamino | |
| 88 | CN | Di-iso-Propylamino | |
| 89 | CN | Di-n-Butylamino | |
| 90 | CN | Di-iso-Butylamino | |
| 91 | CN | Acetyl | |

TABLE II-continued

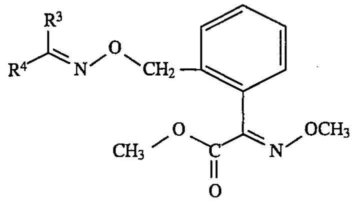

| No. | $R^3$ | $R^4$ | Data |
|---|---|---|---|
| 92 | CN | Propion-1-yl | |
| 93 | CN | Butyr-1-yl | |
| 94 | CN | iso-Butyr-1-yl | |
| 95 | CN | Pivaloyl | |
| 96 | CN | Benzoyl | |
| 97 | CN | 4-Chlorobenzoyl | |
| 98 | CN | Benzylcarbonyl | |
| 99 | CN | Methoxycarbonyl | |
| 100 | CN | Ethoxycarbonyl | |
| 101 | CN | n-Propoxycarbonyl | |
| 102 | CN | iso-Propoxycarbonyl | |
| 103 | CN | n-Butoxycarbonyl | |
| 104 | CN | iso-Butoxycarbonyl | |
| 105 | CN | sec.-Butoxycarbonyl | |
| 106 | CN | tert.-Butoxycarbonyl | |
| 107 | CN | n-Hexoxycarbonyl | |
| 108 | CN | Phenoxycarbonyl | |
| 109 | CN | 4-Chlorophenoxy-carbonyl | |
| 110 | CN | Benzyloxycarbonyl | |
| 111 | CN | Aminocarbonyl | |
| 112 | CN | Dimethylamino-carbonyl | |
| 113 | CN | Diethylaminocarbonyl | |
| 114 | CN | Di-iso-Propylamino-carbonyl | |
| 115 | CN | Phenylaminocarbonyl | |
| 116 | CN | N-Methyl-N-Phenyl-aminocarbonyl | |
| 117 | CN | Phenyl | m.p.: 99–100° C.; IR (KBr): 1436, 1215, 1208, 1097, 1026, 944, 766, 690 |
| 118 | CN | 2-Fluorophenyl | |
| 119 | CN | 3-Fluorophenyl | |
| 120 | CN | 4-Fluorophenyl | |
| 121 | CN | Pentafluorophenyl | |
| 122 | CN | 2-Chlorophenyl | |
| 123 | CN | 3-Chlorophenyl | |
| 124 | CN | 4-Chlorophenyl | |
| 125 | CN | Pentachlorophenyl | |
| 126 | CN | 2,3-Dichlorophenyl | |
| 127 | CN | 2,4-Dichlorophenyl | |
| 128 | CN | 2,5-Dichlorophenyl | |
| 129 | CN | 2,6-Dichlorophenyl | |
| 130 | CN | 3,4-Dichlorophenyl | |
| 131 | CN | 3,5-Dichlorophenyl | |
| 132 | CN | 2,3,4-Trichlorophenyl | |
| 133 | CN | 2,3,5-Trichlorophenyl | |
| 134 | CN | 2,3,6-Trichlorophenyl | |
| 135 | CN | 2,4,5-Trichlorophenyl | |
| 136 | CN | 2,4,6-Trichlorophenyl | |
| 137 | CN | 3,4,5-Trichlorophenyl | |
| 138 | CN | 2,3,4,6-Tetrachloro-phenyl | |
| 139 | CN | 2,3,5-6-Tetrachloro-phenyl | |
| 140 | CN | 2-Bromophenyl | |
| 141 | CN | 3-Bromophenyl | |
| 142 | CN | 4-Bromophenyl | |
| 143 | CN | 2,4-Dibromophenyl | |
| 144 | CN | 3-Bromo-4-fluoro-phenyl | |
| 145 | CN | 3-Bromo-4-methoxy-phenyl | |
| 146 | CN | 2-Iodophenyl | |

TABLE II-continued

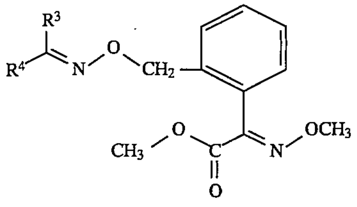

| No. | $R^3$ | $R^4$ | Data |
|---|---|---|---|
| 147 | CN | 3-Iodophenyl | |
| 148 | CN | 4-Iodophenyl | |
| 149 | CN | 2-Chloro-4-fluorophenyl | |
| 150 | CN | 2-Chloro-5-fluorophenyl | |
| 151 | CN | 2-Chloro-6-fluorophenyl | |
| 152 | CN | 2-Chloro-4-bromophenyl | |
| 153 | CN | 2-Bromo-4-chlorophenyl | |
| 154 | CN | 2-Bromo-4-fluorophenyl | |
| 155 | CN | 3-Bromo-4-chlorophenyl | |
| 156 | CN | 3-Chloro-4-fluorophenyl | |
| 157 | CN | 3-Fluoro-4-chlorophenyl | |
| 158 | CN | 2-Cyanophenyl | |
| 159 | CN | 3-Cyanophenyl | |
| 160 | CN | 4-Cyanophenyl | |
| 161 | CN | 2-Nitrophenyl | |
| 162 | CN | 3-Nitrophenyl | |
| 163 | CN | 4-Nitrophenyl | |
| 164 | CN | 2-Methylphenyl | |
| 165 | CN | 3-Methylphenyl | |
| 166 | CN | 4-Methylphenyl | |
| 167 | CN | 2,4-Dimethylphenyl | |
| 168 | CN | 2,6-Dimethylphenyl | |
| 169 | CN | 3,4-Dimethylphenyl | |
| 170 | CN | 3,5-Dimethylphenyl | |
| 171 | CN | 2,3,4-Trimethylphenyl | |
| 172 | CN | 2,3,5-Trimethylphenyl | |
| 173 | CN | 2,3,6-Trimethylphenyl | |
| 174 | CN | 2,4,5-Trimethylphenyl | |
| 175 | CN | 2,4,6-Trimethylphenyl | |
| 176 | CN | 3,4,5-Trimethylphenyl | |
| 177 | CN | Pentamethylphenyl | |
| 178 | CN | 2-Ethylphenyl | |
| 179 | CN | 3-Ethylphenyl | |
| 180 | CN | 4-Ethylphenyl | |
| 181 | CN | 3,5-Diethylphenyl | |
| 182 | CN | 2-n-Propylphenyl | |
| 183 | CN | 3-n-Propylphenyl | |
| 184 | CN | 4-n-Propylphenyl | |
| 185 | CN | 2-iso-Propylphenyl | |
| 186 | CN | 3-iso-Propylphenyl | |
| 187 | CN | 4-iso-Propylphenyl | |
| 188 | CN | 2,4-Di-Iso-Propyl-phenyl | |
| 189 | CN | 3,5-Di-iso-Propyl-phenyl | |
| 190 | CN | 4-n-Butylphenyl | |
| 191 | CN | 4-sec.-Butylphenyl | |
| 192 | CN | 4-iso-Butylphenyl | |
| 193 | CN | 4-tert.-Butylphenyl | |
| 194 | CN | 3-tert.-Butylphenyl | |
| 195 | CN | 2-tert.-Butylphenyl | |
| 196 | CN | 2,4-Di-tert.-Butylphenyl | |
| 197 | CN | 3,5-Di-tert.-Butylphenyl | |
| 198 | CN | 4-n-Hexylphenyl | |
| 199 | CN | 4-n-Dodecylphenyl | |
| 200 | CN | 2-Methyl-4-tert.-Butyl-phenyl | |
| 201 | CN | 2-Methyl-6-tert.-Butyl-phenyl | |
| 202 | CN | 2-Methyl-4-iso-Propyl-phenyl | |
| 203 | CN | 2-Methyl-4-Cyclo-hexylphenyl | |
| 204 | CN | 2-Methyl-4-Phenyl-phenyl | |
| 205 | CN | 2-methyl-4-Benzyl-phenyl | |

TABLE II-continued

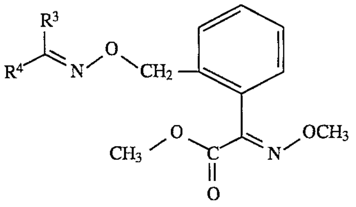

| No. | $R^3$ | $R^4$ | Data |
|---|---|---|---|
| 206 | CN | 2-Methyl-4-Phenoxy-phenyl | |
| 207 | CN | 2-Methyl-4-Benzyloxy-phenyl | |
| 208 | CN | 2-Methyl-3-Chloro-phenyl | |
| 209 | CN | 2-Methyl-4-Chloro-phenyl | |
| 210 | CN | 2-Methyl-5-Chloro-phenyl | |
| 211 | CN | 2-Methyl-6-Chloro-phenyl | |
| 212 | CN | 2-Methyl-4-Fluoro-phenyl | |
| 213 | CN | 2-methyl-3-Bromo-phenyl | |
| 214 | CN | 2-Methyl-4-Bromo-phenyl | |
| 215 | CN | 2-methyl-3-Methoxy-phenyl | |
| 216 | CN | 2-Methyl-4-Methoxy-phenyl | |
| 217 | CN | 2-Methyl-5-Methoxy-phenyl | |
| 218 | CN | 2-Methyl-6-Methoxy-phenyl | |
| 219 | CN | 2-Methyl-4-iso-Propoxyphenyl | |
| 220 | CN | 2-Methyl-2,5-Dimethoxyphenyl | |
| 221 | CN | 2-Methoxyphenyl | |
| 222 | CN | 3-Methoxyphenyl | |
| 223 | CN | 4-Methoxyphenyl | |
| 224 | CN | 2,3-Dimethoxyphenyl | |
| 225 | CN | 2,4-Dimethoxyphenyl | |
| 226 | CN | 2,5-Dimethoxyphenyl | |
| 227 | CN | 2,6-Dimethoxyphenyl | |
| 228 | CN | 3,4-Dimethoxyphenyl | |
| 229 | CN | 3,5-Dimethoxyphenyl | |
| 230 | CN | 3,6-Dimethoxyphenyl | |
| 231 | CN | 2,3,4-Trimethoxyphenyl | |
| 232 | CN | 2,3,5-Trimethoxyphenyl | |
| 233 | CN | 2,3,6-Trimethoxyphenyl | |
| 234 | CN | 2,4,5-Trimethoxyphenyl | |
| 235 | CN | 2,4,6-Trimethoxyphenyl | |
| 236 | CN | 3,4,5-Trimethoxyphenyl | |
| 237 | CN | 2-Ethoxyphenyl | |
| 238 | CN | 3-Ethoxyphenyl | |
| 239 | CN | 4-Ethoxyphenyl | |
| 240 | CN | 2-iso-Propoxyphenyl | |
| 241 | CN | 3-iso-Propoxyphenyl | |
| 242 | CN | 4-iso-Propoxyphenyl | |
| 243 | CN | 3-tert.-Butoxyphenyl | |
| 244 | CN | 4-tert.-Butoxyphenyl | |
| 245 | CN | 2-Trifluoromethoxy-phenyl | |
| 246 | CN | 3-Trifluoromethoxy-phenyl | |
| 247 | CN | 4-Trifluoromethoxy-phenyl | |
| 248 | CN | 3-(1',1',2',2'-Tetra-fluoro)ethoxyphenyl | |
| 249 | CN | 4-(1',1',2',2'-Tetra-fluoro)ethoxyphenyl | |
| 250 | CN | 2-Chloromethylphenyl | |
| 251 | CN | 3-Chloromethylphenyl | |
| 252 | CN | 4-Chloromethylphenyl | |

TABLE II-continued

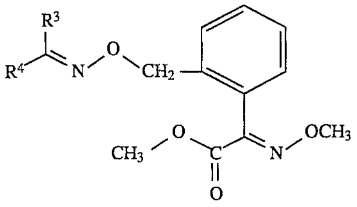

| No. | $R^3$ | $R^4$ | Data |
|---|---|---|---|
| 253 | CN | 2-Trifluoromethylphenyl | |
| 254 | CN | 3-Trifluoromethylphenyl | |
| 255 | CN | 4-Trifluoromethylphenyl | |
| 256 | CN | 2-(Methoxyimino-methyl)phenyl | |
| 257 | CN | 3-(Methoxyimino-methyl)phenyl | |
| 258 | CN | 4-(Methoxyimino-methyl)phenyl | |
| 259 | CN | 2-(Ethoxyimino-methyl)phenyl | |
| 260 | CN | 3-(Ethoxyimino-methyl)phenyl | |
| 261 | CN | 4-(Ethoxyimino-methyl)phenyl | |
| 262 | CN | 2-(n-Propoxyimino-methyl)phenyl | |
| 263 | CN | 3-(n-Propoxyimino methyl)phenyl | |
| 264 | CN | 4-(n-Propoxyimino-methyl)phenyl | |
| 265 | CN | 2-(iso-Propoxyimino-methyl)phenyl | |
| 266 | CN | 3-(iso-Propoxyimino-methyl)phenyl | |
| 267 | CN | 4-(iso-Propoxyimino-methyl)phenyl | |
| 268 | CN | 2-(n-Butoxyimino-methyl)phenyl | |
| 269 | CN | 3-(n-Butoxyimino-methyl)phenyl | |
| 270 | CN | 4-(n-Butoxyimino-methyl)phenyl | |
| 271 | CN | 2-(iso-Butoxyimino-methyl)phenyl | |
| 272 | CN | 3-(iso-Butoxyimino-methyl)phenyl | |
| 273 | CN | 4-(iso-Butoxyimino-methyl)phenyl | |
| 274 | CN | 2-(tert.-Butoxyimino-methyl)phenyl | |
| 275 | CN | 3-(tert.-Butoxyimino-methyl)phenyl | |
| 276 | CN | 4-(tert.-Butoxyimino-methyl)phenyl | |
| 277 | CN | 2-(n-Pentoxyimino-methyl)phenyl | |
| 278 | CN | 3-(n-Pentoxyimino-methyl)phenyl | |
| 279 | CN | 4-(n-Pentoxyimino-methyl)phenyl | |
| 280 | CN | 2-(n-Hexoxyimino-methyl)phenyl | |
| 281 | CN | 3-(n-Hexoxyimino-methyl)phenyl | |
| 282 | CN | 4-(n-Hexoxyimino-methyl)phenyl | |
| 283 | CH | 2-(Allyloxyimino-methyl)phenyl | |
| 284 | CN | 3-(Allyloxyimino-methyl)phenyl | |
| 285 | CN | 4-(Allyloxyimino-methyl)phenyl | |
| 286 | CH | 2-(Benzyloxyimino-methyl)phenyl | |
| 287 | CN | 3-(Benzyloxyimino-methyl)phenyl | |

TABLE II-continued

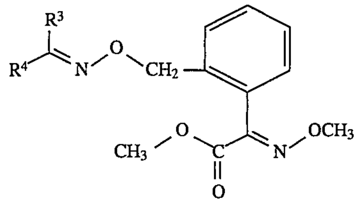

| No. | $R^3$ | $R^4$ | Data |
|---|---|---|---|
| 288 | CN | 4-(Benzyloxyimino-methyl)phenyl | |
| 289 | CN | 2-(Methoxyimino-1'-ethyl)phenyl | |
| 290 | CN | 3-(Methoxyimino-1'-ethyl)phenyl | |
| 291 | CN | 4-(Methoxyimino-1'-ethyl)phenyl | |
| 292 | CN | 2-(Ethoxyimino-1'-ethyl)phenyl | |
| 293 | CN | 3-(Ethoxyimino-1'-ethyl)phenyl | |
| 294 | CN | 4-(Ethoxyimino-1'-ethyl)phenyl | |
| 295 | CN | 2-(n-Propoxyimino-1'-ethyl)phenyl | |
| 296 | CN | 3-(n-Propoxyimino-1'-ethyl)phenyl | |
| 297 | CN | 4-(n-Propoxyimino-1'-ethyl)phenyl | |
| 298 | CN | 2-(n-Butoxyamino-1'-ethyl)phenyl | |
| 299 | CN | 3-(n-Butoxyamino-1'-ethyl)phenyl | |
| 300 | CN | 4-(n-Butoxyamino-1'-ethyl)phenyl | |
| 301 | CN | 2-(n-Pentoxyimino-1'-ethyl)phenyl | |
| 302 | CN | 3-(n-Pentoxyimino-1'-ethyl)phenyl | |
| 303 | CN | 4-(n-Pentoxyimino-1'-ethyl)phenyl | |
| 304 | CN | 2-(n-Hexoxyimino-1'-ethyl)phenyl | |
| 305 | CN | 3-(n-Hexoxyimino-1'-ethyl)phenyl | |
| 306 | CN | 4-(n-Hexoxyimino-1'-ethyl)phenyl | |
| 307 | CN | 2-(Allyloxyimino-1'-ethyl)phenyl | |
| 308 | CN | 3-(Allyloxyimino-1'-ethyl)phenyl | |
| 309 | CN | 4-(Allyloxyimino-1'-ethyl)phenyl | |
| 310 | CN | 2-(Benzyloxyimino-1'-ethyl)phenyl | |
| 311 | CN | 3-(Benzyloxyimino-1'-ethyl)phenyl | |
| 312 | CN | 4-(Benzyloxyimino-1'-ethyl)phenyl | |
| 313 | CN | 2-Phenylphenyl | |
| 314 | CN | 3-Phenylphenyl | |
| 315 | CN | 4-Phenylphenyl | |
| 316 | CN | 2-Phenoxyphenyl | |
| 317 | CN | 3-Phenoxyphenyl | |
| 318 | CN | 4-Phenoxyphenyl | |
| 319 | CN | 2-Benzyloxyphenyl | |
| 320 | CN | 3-Benzyloxyphenyl | |
| 321 | CN | 4-Benzyloxyphenyl | |
| 322 | CN | 4-(imidazol-1'-yl)phenyl | |
| 323 | CN | 4-(Piperazin-1'-yl)phenyl | |
| 324 | CN | 4-(Morpholin-1'-yl)phenyl | |
| 325 | CN | 4-(Piperidin-1'-yl)phenyl | |

TABLE II-continued

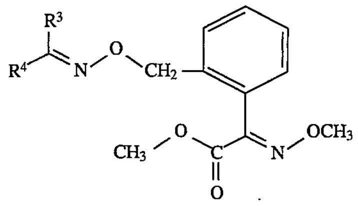

| No. | $R^3$ | $R^4$ | Data |
|---|---|---|---|
| 326 | CN | 4-(Pyridyl-2'-oxy)phenyl | |
| 327 | CN | 2-Cyclopropylphenyl | |
| 328 | CN | 3-Cyclopropylphenyl | |
| 329 | CN | 4-Cyclopropylphenyl | |
| 330 | CN | 3-Cyclohexylphenyl | |
| 331 | CN | 4-Cyclohexylphenyl | |
| 332 | CN | 4-Oxiranylphenyl | |
| 333 | CN | 4-(1',3'-Dioxan-2'-yl)phenyl | |
| 334 | CN | 4-(Tetrahydropyran-2-yloxy)phenyl | |
| 335 | CN | 1-Naphthyl | |
| 336 | CN | 2-Naphthyl | |
| 337 | CN | 9-Anthryl | |
| 338 | CN | 1-Naphthoxy | |
| 339 | CN | 2-Naphthoxy | |
| 340 | CN | 9-Anthroxy | |
| 341 | CN | Phenoxy | |
| 342 | CN | 2-Chlorophenoxy | |
| 343 | CN | 3-Chlorophenoxy | |
| 344 | CN | 4-Chlorophenoxy | |
| 345 | CN | 4-Methylphenoxy | |
| 346 | CN | 4-tert.-Butylphenoxy | |
| 347 | CN | 4-Methoxyphenoxy | |
| 348 | CN | 4-Ethoxyphenoxy | |
| 349 | CN | 4-tert.-Butoxyphenoxy | |
| 350 | CN | Phenylthio | |
| 351 | CN | 2-Chlorophenylthio | |
| 352 | CN | 4-Chlorophenylthio | |
| 353 | CN | Benzyl | |
| 354 | CN | 2-Methylbenzyl | |
| 355 | CN | 3-Methylbenzyl | |
| 356 | CN | 4-Methylbenzyl | |
| 357 | CN | 4-tert.-Butylbenzyl | |
| 358 | CN | 2-Chlorobenzyl | |
| 359 | CN | 3-Chlorobenzyl | |
| 360 | CN | 4-Chlorobenzyl | |
| 361 | CN | 2,4-Dichlorobenzyl | |
| 362 | CN | 2,6-Dichlorobenzyl | |
| 363 | CN | 2,4,6-Trichlorobenzyl | |
| 364 | CN | 2-Trifluoromethyl-benzyl | |
| 365 | CN | 3-Trifluoromethyl-benzyl | |
| 366 | CN | 4-Trifluoromethyl-benzyl | |
| 367 | CN | 2-Methoxybenzyl | |
| 368 | CN | 4-Methoxybenzyl | |
| 369 | CN | 4-tert.-Butoxybenzyl | |
| 370 | CN | 4-Phenoxybenzyl | |
| 371 | CN | 1-Phenethyl | |
| 372 | CN | 2-Phenethyl | |
| 373 | CN | 1-Phenylpropyl | |
| 374 | CN | 2-Phenylpropyl | |
| 375 | CN | 3-Phenylpropyl | |
| 376 | CN | 2-Methyl-2-phenyl-propyl | |
| 377 | CN | 2-Methyl-3-phenyl-propyl | |
| 378 | CN | 4-Phenylbutyl | |
| 379 | CN | 2-Phenyl-1-ethenyl | |
| 380 | CN | 1-Phenyl-1-ethenyl | |
| 381 | CN | 1-Phenyl-1-propenyl | |
| 382 | CN | 1-Phenyl-1-propen-2-yl | |
| 383 | CN | 2,2-Diphenylethenyl | |
| 384 | CN | Phenoxymethyl | |

TABLE II-continued

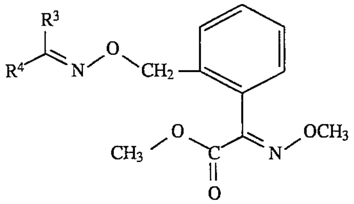

| No. | $R^3$ | $R^4$ | Data |
|---|---|---|---|
| 385 | CN | 2-Pyridyl | |
| 386 | CN | 3-Pyridyl | |
| 387 | CN | 4-Pyridyl | |
| 388 | CN | 2,6-Pyrimidinyl | |
| 389 | CN | 1,5-Pyrimidinyl | |
| 390 | CN | 2-Thienyl | |
| 391 | CN | 3-Thienyl | |
| 392 | CN | 2-Furyl | |
| 393 | CN | 3-Furyl | |
| 394 | CN | 1-Pyrrolyl | |
| 395 | CN | 1-imidazolyl | |
| 396 | CN | 1,2,4-Triazolyl | |
| 397 | CN | 1,3,4-Triazolyl | |
| 398 | CN | 4-Thiazolyl | |
| 399 | CN | 2-Benzothiazolyl | |
| 400 | CN | 2-Pyridyloxy | |
| 401 | CN | 2-Pyrimidinyloxy | |
| 402 | CN | 2-Pyridylthio | |
| 403 | CN | 2-Pyrimidinylthio | |
| 404 | CN | 2-Benzothiazolylthio | |
| 405 | CN | Phenylthiomethyl | |
| 406 | CN | 2-Pyridylmethyl | |
| 407 | CN | 3-Pyridylmethyl | |
| 408 | CN | Furfurytoxy | |
| 409 | CN | Thienylmethoxy | |
| 410 | CN | 3-Isoxazolylmethoxy | |
| 411 | CN | 2-Oxazolylmethoxy | |
| 412 | CN | 2-Pyridylmethoxy | |
| 413 | CN | 2'-Furyl-2-ethenyl | |
| 414 | CN | 2'-Thienyl-2-ethenyl | |
| 415 | CN | 3'-Pyridyl-2-ethenyl | |
| 416 | CN | Oxiranyl | |
| 417 | CN | 1-Aziridinyl | |
| 418 | CN | 1-Azetidinyl | |
| 419 | CN | 1-Pyrrolidinyl | |
| 420 | CN | 2-Tetrahydrofuryl | |
| 421 | CN | 2-Tetrahydropyranyl | |
| 422 | CN | 3-Tetrahydropyranyl | |
| 423 | CN | 1-Piperidinyl | |
| 424 | CN | 1-Morpholinyl | |
| 425 | CN | 1-Piperazinyl | |
| 426 | CN | 1,3-Dioxan-2-yl | |
| 427 | CN | 3-Tetrahydrothiopyranyl | |
| 428 | CN | 2-Dihydropyranyloxy | |
| 429 | CN | 2-Tetrahydropyranyloxy | oil; IR (film): 1439, 1228, 1209, 1050, 1025 767 |
| 430 | CN | $(CH_2)_4$ | |
| 431 | CN | $(CH_2)_5$ | |
| 432 | CN | $(CH_2)_6$ | |
| 433 | CN | | |
| 434 | CN | | |
| 435 | CN | 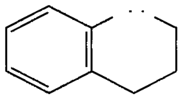 | |
| 436 | CN | 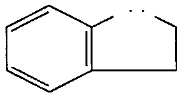 | |

TABLE II-continued

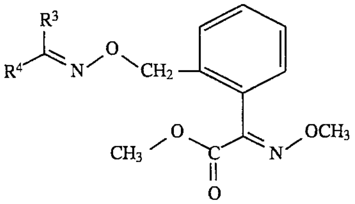

| No. | $R^3$ | $R^4$ | Data |
|---|---|---|---|
| 437 | CN | 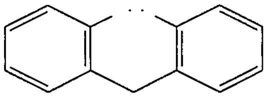 | |
| 438 | CN | 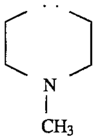 | |
| 439 | CN | 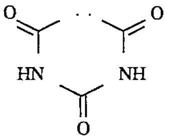 | |
| 440 | CN | 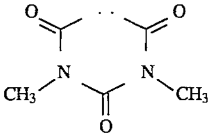 | |
| 441 | CN | $CF_3$ | |
| 442 | CN | 2-Fluoroethyl | |
| 443 | CN | 2,2,2-Trifluoroethyl | |
| 444 | CN | Pentafluoroethyl | |
| 445 | CN | Chloromethyl | |
| 446 | CN | Dichloromethyl | |
| 447 | CN | Trichloromethyl | |
| 448 | CN | 2-Chloroethyl | |
| 449 | CN | 2,2,2-Trichloroethyl | |
| 450 | CN | Pentachloroethyl | |
| 451 | CN | Cyclopropyl | |
| 452 | CN | Cyclobutyl | |
| 453 | CN | Cyclopentyl | |
| 454 | CN | Cyclohexyl | |
| 455 | CN | 1-Methylcyclopropyl | |
| 456 | CN | 2,2-Dimethylcyclo-propyl | |
| 457 | CN | 1-Methylcyclohexyl | |
| 458 | CN | 2,2-Difluorocyclopropyl | |
| 459 | CN | 2,2-Dichlorocyclopropyl | |
| 460 | CN | 2,2-Dibromocyclopropyl | |
| 461 | CN | 2,2-Dichloro-3-Methylcyclopropyl | |
| 462 | CN | 2,2,3,3-Tetrafluoro-cyclobutyl | |
| 463 | CN | Ethenyl | |
| 464 | CN | 1-Propenyl | |
| 465 | CN | 2-Methyl-1-propenyl | |
| 466 | CN | 4-Methylpent-3-en-1-yl | |
| 467 | CN | 2-Propenyl | |
| 468 | CN | 2-Butenyl | |
| 469 | CN | 1-Methyl-2-propenyl | |
| 470 | CN | 3-Methyl-2-butenyl | |
| 471 | CN | 2,2-Difluoroethenyl | |
| 472 | CN | 2,2-Dichloroethenyl | |
| 473 | CN | 3,3,3-Trifluoro-propenyl | |
| 474 | CN | 3,3,3-Trichloro-propenyl | |
| 475 | CN | 3-Chloro-2-propenyl | |

TABLE II-continued

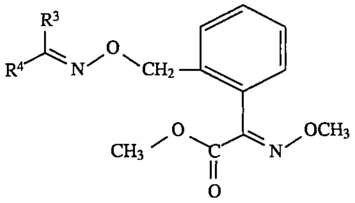

| No. | $R^3$ | $R^4$ | Data |
|---|---|---|---|
| 476 | CN | Cyclopent-1-enyl | |
| 477 | CN | Cyclopentadienyl | |
| 478 | CN | Cyclohex-1-enyl | |
| 479 | CN | Pentafluorocyclo-pentadienyl | |
| 480 | CN | Pentachlorocyclo-pentadienyl | |
| 481 | CN | Styryl | |
| 482 | $CH_3$ | Methoxymethyl | |
| 483 | $CH_3$ | Ethoxymethyl | |
| 484 | $CH_3$ | n-Propoxymethyl | |
| 485 | $CH_3$ | iso-Propoxymethyl | |
| 486 | $CH_3$ | tert.-Butoxymethyl | |
| 487 | $CH_3$ | 2-Methoxyprop-2-yl | |
| 488 | $CH_3$ | 2-Ethoxyprop-2-yl | |
| 489 | $CH_3$ | 2-n-Propoxyprop-2-yl | |
| 490 | $CH_3$ | 2-iso-Propoxyprop-2-yl | |
| 491 | $CH_3$ | 2-tert.-Butoxyprop-2-yl | |
| 492 | $CH_3$ | Methylthiomethyl | |
| 493 | $CH_3$ | tert.-Butylthiomethyl | |
| 494 | $CH_3$ | 2-Methylthioprop-2-yl | |
| 495 | $CH_3$ | 2-iso-Propylthioprop-2-yl | |
| 496 | $CH_3$ | 2-tert.-Butylthioprop-2-yl | |
| 497 | $CH_3$ | Methyl | m.p. 68–71° C.; IR (KBr): 1137, 1298, 1067, 1023, 1007, 771 |
| 498 | $CH_3$ | Ethyl | |
| 499 | $CH_3$ | n-Propyl | |
| 500 | $CH_3$ | iso-Propyl | |
| 501 | $CH_3$ | n-Butyl | |
| 502 | $CH_3$ | iso-Butyl | |
| 503 | $CH_3$ | sec.-Butyl | |
| 504 | $CH_3$ | tert.-Butyl | |
| 505 | $CH_3$ | n-Hexyl | |
| 506 | $CH_3$ | n-Decyl | |
| 507 | $CH_3$ | Cyclopropyl | |
| 508 | $CH_3$ | Cyclohexyl | |
| 509 | $CH_3$ | Phenylthiomethyl | |
| 510 | $CH_3$ | 2-Phenylthiomethyl | |
| 511 | $CH_3$ | 2-(2'-Chlorophenyl-thio)prop-2-yl | |
| 512 | $CH_3$ | Ethynyl | |
| 513 | $CH_3$ | 1-Propynyl | |
| 514 | $CH_3$ | Methoxy | |
| 515 | $CH_3$ | Ethoxy | |
| 516 | $CH_3$ | n-Propoxy | |
| 517 | $CH_3$ | iso-Propoxy | |
| 518 | $CH_3$ | n-Butoxy | |
| 519 | $CH_3$ | iso-Butoxy | |
| 520 | $CH_3$ | sec.-Butoxy | |
| 521 | $CH_3$ | tert.-Butoxy | |
| 522 | $CH_3$ | Methylthio | |
| 523 | $CH_3$ | Ethylthio | |
| 524 | $CH_3$ | n-Propylthio | |
| 525 | $CH_3$ | iso-Propylthio | |
| 526 | $CH_3$ | n-Butylthio | |
| 527 | $CH_3$ | iso-Butylthio | |
| 528 | $CH_3$ | sec.-Butylthio | |
| 529 | $CH_3$ | tert.-Butylthio | |
| 530 | $CH_3$ | Benzylthio | |
| 531 | $CH_3$ | Trifluoromethoxy | |
| 532 | $CH_3$ | Cyano | |
| 533 | $CH_3$ | Amino | |
| 534 | $CH_3$ | Methylamino | |

TABLE II-continued

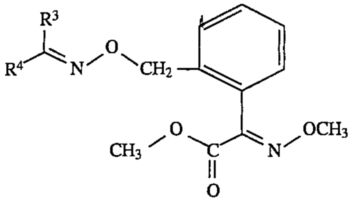

| No. | $R^3$ | $R^4$ | Data |
|---|---|---|---|
| 535 | $CH_3$ | Dimethylamino | |
| 536 | $CH_3$ | Ethylamino | |
| 537 | $CH_3$ | Diethylamino | |
| 538 | $CH_3$ | Di-n-Propylamino | |
| 539 | $CH_3$ | Di-iso-Propylamino | |
| 540 | $CH_3$ | Di-n-Butylamino | |
| 541 | $CH_3$ | Di-iso-Butylamino | |
| 542 | $CH_3$ | Acetyl | |
| 543 | $CH_3$ | Propion-1-yl | |
| 544 | $CH_3$ | Butyr-1-yl | |
| 545 | $CH_3$ | iso-Butyr-1-yl | |
| 546 | $CH_3$ | Pivaloyl | |
| 547 | $CH_3$ | Benzoyl | |
| 548 | $CH_3$ | 4-Chlorobenzoyl | |
| 549 | $CH_3$ | Benzylcarbonyl | |
| 550 | $CH_3$ | Methoxycarbonyl | |
| 551 | $CH_3$ | Ethoxycarbonyl | |
| 552 | $CH_3$ | n-Propoxycarbonyl | |
| 553 | $CH_3$ | iso-Propoxycarbonyl | |
| 554 | $CH_3$ | n-Butoxycarbonyl | |
| 555 | $CH_3$ | iso-Butoxycarbonyl | |
| 556 | $CH_3$ | sec.-Butoxycarbonyl | |
| 557 | $CH_3$ | tert.-Butoxycarbonyl | |
| 558 | $CH_3$ | n-Hexoxycarbonyl | |
| 559 | $CH_3$ | Phenoxycarbonyl | |
| 560 | $CH_3$ | 4-Chlorophenoxy-carbonyl | |
| 561 | $CH_3$ | Benzyloxycarbonyl | |
| 562 | $CH_3$ | Aminocarbonyl | |
| 563 | $CH_3$ | Dimethylamino-carbonyl | |
| 564 | $CH_3$ | Diethylamino-carbonyl | |
| 565 | $CH_3$ | Di-iso-Propylamino-carbonyl | |
| 566 | $CH_3$ | Phenylaminocarbonyl | |
| 567 | $CH_3$ | N-Methyl-N-Phenyl-aminocarbonyl | |
| 568 | $CH_3$ | Phenyl | |
| 569 | $CH_3$ | 2-Fluorophenyl | m.p.: 89–91° C.; IR (KBr): 1732, 1071, 1012, 998, 768 |
| 570 | $CH_3$ | 3-Fluorophenyl | m.p.: 83–85° C.; IR (KBr): 1724, 1204, 1067, 1031, 1015, 955 |
| 571 | $CH_3$ | 4-Fluorophenyl | m.p.: 76–8° C.; IR (KBr): 1737, 1510, 1302, 1224, 1072, 1031, 1015, 933 |
| 572 | $CH_3$ | Pentafluorophenyl | |
| 573 | $CH_3$ | 2-Chlorophenyl | |
| 574 | $CH_3$ | 3-Chlorophenyl | m.p.: 61–63° C.; IR (KBr): 1735, 1070, 1015, 1002, 785 |
| 575 | $CH_3$ | 4-Chlorophenyl | oil; IR (film): 1708, 1634, 1256, 1129 |
| 576 | $CH_3$ | Pentachlorophenyl | |
| 577 | $CH_3$ | 2,3-Dichlorophenyl | |
| 578 | $CH_3$ | 2,4-Dichlorophenyl | |
| 579 | $CH_3$ | 2,5-Dichlorophenyl | |
| 580 | $CH_3$ | 2,6-Dichlorophenyl | |
| 581 | $CH_3$ | 3,4-Dichlorophenyl | |

TABLE II-continued

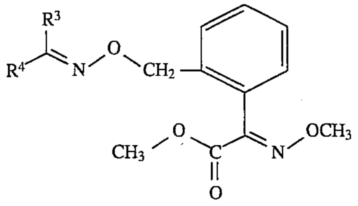

| No. | $R^3$ | $R^4$ | Data |
|---|---|---|---|
| 582 | $CH_3$ | 3,5-Dichlorophenyl | m.p.: 95–7° C.; IR (KBr): 1723, 1556, 1224, 1067, 1030, 1014, 957 |
| 583 | $CH_3$ | 2,3,4-Trichlorophenyl | m.p.: 118–20° C. |
| 584 | $CH_3$ | 2,3,5-Trichlorophenyl | |
| 585 | $CH_3$ | 2,3,6-Trichlorophenyl | |
| 586 | $CH_3$ | 2,4,5-Trichlorophenyl | |
| 587 | $CH_3$ | 2,4,6-Trichlorophenyl | |
| 588 | $CH_3$ | 3,4,5-Trichlorophenyl | |
| 589 | $CH_3$ | 2,3,4,6-Tetrachloro-phenyl | |
| 590 | $CH_3$ | 2,3,5,6-Tetrachloro-phenyl | |
| 591 | $CH_3$ | 2-Bromophenyl | |
| 592 | $CH_3$ | 3-Bromophenyl | m.p.: 80–4° C.; IR (KBr): 1723, 1556, 1224, 1067, 1030, 1014, 957 |
| 593 | $CH_3$ | 4-Bromophenyl | m.p.: 73–75° C.; IR (KBr): 1736, 1071, 1029, 1015, 932 |
| 594 | $CH_3$ | 2,4-Dibromophenyl | |
| 595 | $CH_3$ | 3-Bromo-4-fluorophenyl | |
| 596 | $CH_3$ | 3-Bromo-4-methoxy-phenyl | |
| 597 | $CH_3$ | 2-Iodophenyl | |
| 598 | $CH_3$ | 3-Iodophenyl | |
| 599 | $CH_3$ | 4-Iodophenyl | |
| 600 | $CH_3$ | 2-Chloro-4-fluorophenyl | |
| 601 | $CH_3$ | 2-Chloro-5-fluorophenyl | |
| 602 | $CH_3$ | 2-Chloro-6-fluorophenyl | |
| 603 | $CH_3$ | 2-Chloro-4-bromophenyl | |
| 604 | $CH_3$ | 2-Bromo-4-chlorophenyl | |
| 605 | $CH_3$ | 2-Bromo-4-fluorophenyl | |
| 606 | $CH_3$ | 3-Bromo-4-chlorophenyl | |
| 607 | $CH_3$ | 3-Chloro-4-fluorophenyl | |
| 608 | $CH_3$ | 3-Fluoro-4-chlorophenyl | |
| 609 | $CH_3$ | 2-Cyanophenyl | |
| 610 | $CH_3$ | 3-Cyanophenyl | |
| 611 | $CH_3$ | 4-Cyanophenyl | |
| 612 | $CH_3$ | 2-Nitrophenyl | |
| 613 | $CH_3$ | 3-Nitrophenyl | |
| 614 | $CH_3$ | 4-Nitrophenyl | m.p.: 88–90° C.; IR (KBr): 1725, 1512, 1342, 1219, 1068, 1009, 854 |
| 615 | $CH_3$ | 2-Methylphenyl | |
| 616 | $CH_3$ | 3-Methylphenyl | m.p.: 93–96° C. |
| 617 | $CH_3$ | 4-Methylphenyl | m.p.: 82–84° C.; IR (KBr): 1722, 1068, 1038, 1015, 920 |
| 618 | $CH_3$ | 2,4-Dimethylphenyl | |
| 619 | $CH_3$ | 2,6-Dimethylphenyl | |
| 620 | $CH_3$ | 3,4-Dimethylphenyl | |
| 621 | $CH_3$ | 3,5-Dimethylphenyl | |
| 622 | $CH_3$ | 2,3,4-Trimethylphenyl | |
| 623 | $CH_3$ | 2,3,5-Trimethylphenyl | |
| 624 | $CH_3$ | 2,3,6-Trimethylphenyl | |
| 625 | $CH_3$ | 2,4,5-Trimethylphenyl | |
| 626 | $CH_3$ | 2,4,6-Trimethylphenyl | |
| 627 | $CH_3$ | 3,4,5-Trimethylphenyl | |
| 628 | $CH_3$ | Pentamethylphenyl | |
| 629 | $CH_3$ | 2-Ethylphenyl | |
| 630 | $CH_3$ | 3-Ethylphenyl | |

TABLE II-continued

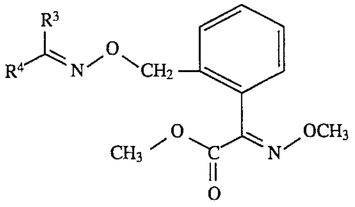

| No. | $R^3$ | $R^4$ | Data |
|---|---|---|---|
| 631 | $CH_3$ | 4-Ethylphenyl | |
| 632 | $CH_3$ | 3,5-Diethylphenyl | |
| 633 | $CH_3$ | 2-n-Propylphenyl | |
| 634 | $CH_3$ | 3-n-Propylphenyl | |
| 635 | $CH_3$ | 4-n-Propylphenyl | |
| 636 | $CH_3$ | 2-iso-Propylphenyl | |
| 637 | $CH_3$ | 3-iso-Propylphenyl | |
| 638 | $CH_3$ | 4-iso-Propylphenyl | |
| 639 | $CH_3$ | 2,4-Di-iso-Propyl-phenyl | |
| 640 | $CH_3$ | 3,5-Di-iso-Propyl-phenyl | |
| 641 | $CH_3$ | 4-n-Butylphenyl | |
| 642 | $CH_3$ | 4-sec.-Butylphenyl | |
| 643 | $CH_3$ | 4-iso-Butylphenyl | |
| 644 | $CH_3$ | 4-tert.-Butylphenyl | m.p.: 45–50° C. |
| 645 | $CH_3$ | 3-tert.-Butylphenyl | |
| 646 | $CH_3$ | 2-tert.-Butylphenyl | |
| 647 | $CH_3$ | 2,4-Di-tert.-Butyl-phenyl | |
| 648 | $CH_3$ | 3,5-Di-tert.-Butyl-phenyl | |
| 649 | $CH_3$ | 4-n-Hexylphenyl | |
| 650 | $CH_3$ | 4-n-Dodecylphenyl | |
| 651 | $CH_3$ | 2-Methyl-4-tert.-Butyl-phenyl | |
| 652 | $CH_3$ | 2-Methyl-6-tert.-Butyl-phenyl | |
| 653 | $CH_3$ | 2-Methyl-4-iso-Propyl-phenyl | |
| 654 | $CH_3$ | 2-Methyl-4-Cyclohexyl-phenyl | |
| 655 | $CH_3$ | 2-Methyl-4-Phenyl-phenyl | |
| 656 | $CH_3$ | 2-Methyl-4-Benzyl-phenyl | |
| 657 | $CH_3$ | 2-Methyl-4-Phenoxy-phenyl | |
| 658 | $CH_3$ | 2-Methyl-4-Benzyloxy-phenyl | |
| 659 | $CH_3$ | 2-Methyl-3-Chloro-phenyl | |
| 660 | $CH_3$ | 2-Methyl-4-Chloro-phenyl | |
| 661 | $CH_3$ | 2-Methyl-5-Chloro-phenyl | |
| 662 | $CH_3$ | 2-Methyl-6-chloro-phenyl | |
| 663 | $CH_3$ | 2-Methyl-4-fluoro-phenyl | |
| 664 | $CH_3$ | 2-Methyl-3-bromo-phenyl | |
| 665 | $CH_3$ | 2-Methyl-4-bromo-phenyl | |
| 666 | $CH_3$ | 2-Methyl-3-methoxy-phenyl | |
| 667 | $CH_3$ | 2-Methyl-4-methoxy-phenyl | |
| 668 | $CH_3$ | 2-Methyl-5-methoxy-phenyl | |
| 669 | $CH_3$ | 2-Methyl-6-methoxy-phenyl | |
| 670 | $CH_3$ | 2-Methyl-4-iso-Propoxyphenyl | |
| 671 | $CH_3$ | 2-Methyl-2,5-dimethoxyphenyl | |
| 672 | $CH_3$ | 2-Methoxyphenyl | m.p.: 74–6° C.; |

TABLE II-continued

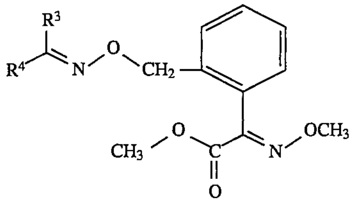

| No. | $R^3$ | $R^4$ | Data |
|---|---|---|---|
| | | | IR (KBr): 1741, 1433, 1295, 1249, 1224, 1067, 1022, 878 |
| 673 | $CH_3$ | 3-Methoxyphenyl | |
| 674 | $CH_3$ | 4-Methoxyphenyl | m.p.: 89–91° C. |
| 675 | $CH_3$ | 2,3-Dimethoxyphenyl | |
| 676 | $CH_3$ | 2,4-Dimethoxyphenyl | |
| 677 | $CH_3$ | 2,5-Dimethoxyphenyl | |
| 678 | $CH_3$ | 2,6-Dimethoxyphenyl | |
| 679 | $CH_3$ | 3,4-Dimethoxyphenyl | |
| 680 | $CH_3$ | 3,5-Dimethoxyphenyl | |
| 681 | $CH_3$ | 3,6-Dimethoxyphenyl | |
| 682 | $CH_3$ | 2,3,4-Trimethoxy-phenyl | |
| 683 | $CH_3$ | 2,3,5-Trimethoxy-phenyl | |
| 684 | $CH_3$ | 2,3,6-Trimethoxy-phenyl | |
| 685 | $CH_3$ | 2,4,5-Trimethoxy-phenyl | |
| 686 | $CH_3$ | 2,4,6-Trimethoxy-phenyl | |
| 687 | $CH_3$ | 3,4,5-Trimethoxy-phenyl | |
| 688 | $CH_3$ | 2-Ethoxyphenyl | |
| 689 | $CH_3$ | 3-Ethoxyphenyl | |
| 690 | $CH_3$ | 4-Ethoxyphenyl | |
| 691 | $CH_3$ | 2-iso-Propoxyphenyl | |
| 692 | $CH_3$ | 3-iso-Propoxyphenyl | |
| 693 | $CH_3$ | 4-iso-Propoxyphenyl | |
| 694 | $CH_3$ | 3-tert.-Butoxyphenyl | |
| 695 | $CH_3$ | 4-tert.-Butoxyphenyl | |
| 696 | $CH_3$ | 2-Trifluoromethoxy-phenyl | |
| 697 | $CH_3$ | 3-Trifluoromethoxy-phenyl | |
| 698 | $CH_3$ | 4-Trifluoromethoxy-phenyl | |
| 699 | $CH_3$ | 3-(1',1',2',2'-Tetra-fluoro)ethoxyphenyl | |
| 700 | $CH_3$ | 4-(1',1',2',2'-Tetra-fluoro)ethoxyphenyl | |
| 701 | $CH_3$ | 2-Chloromethylphenyl | |
| 702 | $CH_3$ | 3-Chloromethylphenyl | |
| 703 | $CH_3$ | 4-Chloromethylphenyl | |
| 704 | $CH_3$ | 2-Trifluoromethyl-phenyl | m.p.: 78–80° C.; IR (KBr): 1741, 1315, 1116, 1068, 1010 |
| 705 | $CH_3$ | 3-Trifluoromethyl-phenyl | m.p.: 70–72° C.; IR (KBr): 1740, 1291, 1281, 1164, 1124, 1073, 1010 |
| 706 | $CH_3$ | 4-Trifluoromethyl-phenyl | m.p.: 57–58° C.; (IR (KBr): 1728, 1333, 1318, 1106, 1069, 986 |
| 707 | $CH_3$ | 2-(Methoxyimino-methyl)phenyl | |
| 708 | $CH_3$ | 3-(Methoxyimino-methyl)phenyl | |
| 709 | $CH_3$ | 4-(Methoxyimino-methyl)phenyl | |
| 710 | $CH_3$ | 2-(Ethoxyimino-methyl)phenyl | |
| 711 | $CH_3$ | 3-(Ethoxyimino-methyl)phenyl | |

TABLE II-continued

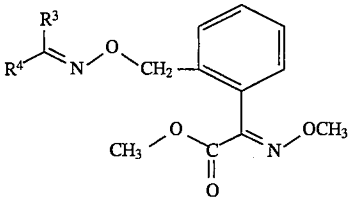

| No. | $R^3$ | $R^4$ | Data |
|---|---|---|---|
| 712 | $CH_3$ | 4-(Ethoxyimino-methyl)phenyl | |
| 713 | $CH_3$ | 2-(n-Propoxyimino-methyl)phenyl | |
| 714 | $CH_3$ | 3-(n-Propoxyimino-methyl)phenyl | |
| 715 | $CH_3$ | 4-(n-Propoxyimino-methyl)phenyl | |
| 716 | $CH_3$ | 2-(iso-Propoxyimino-methyl)phenyl | |
| 717 | $CH_3$ | 3-(iso-Propoxyimino-methyl)phenyl | |
| 718 | $CH_3$ | 4-(iso-Propoxyimino-methyl)phenyl | |
| 719 | $CH_3$ | 2-(n-Butoxyimino-methyl)phenyl | |
| 720 | $CH_3$ | 3-(n-Butoxyimino-methyl)phenyl | |
| 721 | $CH_3$ | 4-(n-Butoxyimino-methyl)phenyl | |
| 722 | $CH_3$ | 2-(iso-Butoxyimino-methyl)phenyl | |
| 723 | $CH_3$ | 3-(iso-Butoxyimino-methyl)phenyl | |
| 724 | $CH_3$ | 4-(iso-Butoxyimino-methyl)phenyl | |
| 725 | $CH_3$ | 2-(tert.-Butoxyimino-methyl)phenyl | |
| 726 | $CH_3$ | 3-(tert.-Butoxyimino-methyl)phenyl | |
| 727 | $CH_3$ | 4-(tert.-Butoxyimino-methyl)phenyl | |
| 728 | $CH_3$ | 2-(n-Pentoxyimino-methyl)phenyl | |
| 729 | $CH_3$ | 3-(n-Pentoxyimino-methyl)phenyl | |
| 730 | $CH_3$ | 4-(n-Pentoxyimino-methyl)phenyl | |
| 731 | $CH_3$ | 2-(n-Hexoxyimino-methyl)phenyl | |
| 732 | $CH_3$ | 3-(n-Hexoxyimino-methyl)phenyl | |
| 733 | $CH_3$ | 4-(n-Hexoxyimino-methyl)phenyl | |
| 734 | $CH_3$ | 2-(Allyloxyimino-methyl)phenyl | |
| 735 | $CH_3$ | 3-(Allyloxyimino-methyl)phenyl | |
| 736 | $CH_3$ | 4-(Allyloxyimino-methyl)phenyl | |
| 737 | $CH_3$ | 2-(Benzyloxyimino-methyl)phenyl | |
| 738 | $CH_3$ | 3-(Benzyloxyimino-methyl)phenyl | |
| 739 | $CH_3$ | 4-(Benzyloxyimino-methyl)phenyl | |
| 740 | $CH_3$ | 2-(Methoxyimino-1'-ethyl)phenyl | |
| 741 | $CH_3$ | 3-(Methoxyimino-1'-ethyl)phenyl | |
| 742 | $CH_3$ | 4-(Methoxyimino-1'-ethyl)phenyl | |
| 743 | $CH_3$ | 2-(Ethoxyimino-1'-ethyl)phenyl | |
| 744 | $CH_3$ | 3-(Ethoxyimino-1'-ethyl)phenyl | |

TABLE II-continued

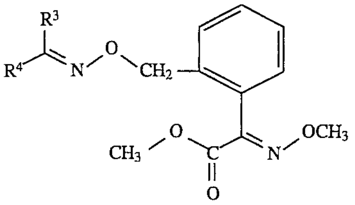

| No. | $R^3$ | $R^4$ | Data |
|---|---|---|---|
| 745 | $CH_3$ | 4-(Ethoxyimino-1'-ethyl)phenyl | |
| 746 | $CH_3$ | 2-(n-Propoxyimino-1'-ethyl)phenyl | |
| 747 | $CH_3$ | 3-(n-Propoxyimino-1'-ethyl)phenyl | |
| 748 | $CH_3$ | 4-(n-Propoxyimino-1'-ethyl)phenyl | |
| 749 | $CH_3$ | 2-(n-Butoxyamino-1'-ethyl)phenyl | |
| 750 | $CH_3$ | 3-(n-Butoxyamino-1'-ethyl)phenyl | |
| 751 | $CH_3$ | 4-(n-Butoxyamino-1'-ethyl)phenyl | |
| 752 | $CH_3$ | 2-(n-Pentoxyimino-1'-ethyl)phenyl | |
| 753 | $CH_3$ | 3-(n-Pentoxyimino-1'-ethyl)phenyl | |
| 754 | $CH_3$ | 4-(n-Pentoxyimino-1'-ethyl)phenyl | |
| 755 | $CH_3$ | 2-(n-Hexoxyimino-1'-ethyl)phenyl | |
| 756 | $CH_3$ | 3-(n-Hexoxyimino-1'-ethyl)phenyl | |
| 757 | $CH_3$ | 4-(n-Hexoxyimino-1'-ethyl)phenyl | |
| 758 | $CH_3$ | 2-(Allyloxyimino-1'-ethyl)phenyl | |
| 759 | $CH_3$ | 3-(Allyloxyimino-1'-ethyl)phenyl | |
| 760 | $CH_3$ | 4-(Allyloxyimino-1'-ethyl)phenyl | |
| 761 | $CH_3$ | 2-(Benzyloxyimino-1'-ethyl)phenyl | |
| 762 | $CH_3$ | 3-(Benzyloxyimino-1'-ethyl)phenyl | |
| 763 | $CH_3$ | 4-(Benzyloxyimino-1'-ethyl)phenyl | |
| 764 | $CH_3$ | 2-Phenylphenyl | |
| 765 | $CH_3$ | 3-Phenylphenyl | |
| 766 | $CH_3$ | 4-Phenylphenyl | |
| 767 | $CH_3$ | 2-Phenoxyphenyl | |
| 768 | $CH_3$ | 3-Phenoxyphenyl | |
| 769 | $CH_3$ | 4-Phenoxyphenyl | m.p.: 91–3° C.; IR (KBr): 1732, 1587, 1491, 1241, 1071, 1014, 995, 769 |
| 770 | $CH_3$ | 2-Benzyloxyphenyl | |
| 771 | $CH_3$ | 3-Benzyloxyphenyl | |
| 772 | $CH_3$ | 4-Benzyloxyphenyl | |
| 773 | $CH_3$ | 4-(Imidazol-1'-yl)phenyl | |
| 774 | $CH_3$ | 4-(Piperazin-1'-yl)phenyl | |
| 775 | $CH_3$ | 4-(Morpholin-1'-yl)phenyl | |
| 776 | $CH_3$ | 4-(Piperidin-1'-yl)phenyl | |
| 777 | $CH_3$ | 4-(Pyridyl-2'-oxy)phenyl | |
| 778 | $CH_3$ | 2-Cyclopropylphenyl | |
| 779 | $CH_3$ | 3-Cyclopropylphenyl | |
| 780 | $CH_3$ | 4-Cyclopropylphenyl | |
| 781 | $CH_3$ | 3-Cyclohexylphenyl | |
| 782 | $CH_3$ | 4-Cyclohexylphenyl | m.p.: 53–5° C. |
| 783 | $CH_3$ | 4-Oxiranylphenyl | |

TABLE II-continued

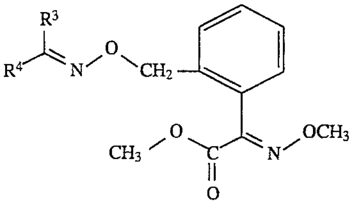

| No. | $R^3$ | $R^4$ | Data |
|---|---|---|---|
| 784 | $CH_3$ | 4-(1',3'-Dioxan-2'-phenyl | |
| 785 | $CH_3$ | 4-(Tetrahydropyran-2-yloxy)phenyl | |
| 786 | $CH_3$ | 1-Naphthyl | |
| 787 | $CH_3$ | 2-Naphthyl | |
| 788 | $CH_3$ | 9-Anthryl | |
| 789 | $CH_3$ | 1-Naphthoxy | |
| 790 | $CH_3$ | 2-Naphthoxy | |
| 791 | $CH_3$ | 9-Anthroxy | |
| 792 | $CH_3$ | Phenoxy | |
| 793 | $CH_3$ | 2-Chlorophenoxy | |
| 794 | $CH_3$ | 3-Chlorophenoxy | |
| 795 | $CH_3$ | 4-Chlorophenoxy | |
| 796 | $CH_3$ | 4-Methylphenoxy | |
| 797 | $CH_3$ | 4-tert.-Butylphenoxy | |
| 798 | $CH_3$ | 4-Methoxyphenoxy | |
| 799 | $CH_3$ | 4-Ethoxyphenoxy | |
| 800 | $CH_3$ | 4-tert.-Butoxyphenoxy | |
| 801 | $CH_3$ | Phenylthio | |
| 802 | $CH_3$ | 2-Chlorophenylthio | |
| 803 | $CH_3$ | 4-Chlorophenylthio | |
| 804 | $CH_3$ | Benzyl | |
| 805 | $CH_3$ | 2-Methylbenzyl | |
| 806 | $CH_3$ | 3-Methylbenzyl | |
| 807 | $CH_3$ | 4-Methylbenzyl | |
| 808 | $CH_3$ | 4-tert.-Butylbenzyl | |
| 809 | $CH_3$ | 2-Chlorobenzyl | |
| 810 | $CH_3$ | 3-Chlorobenzyl | |
| 811 | $CH_3$ | 4-Chlorobenzyl | |
| 812 | $CH_3$ | 2,4-Dichlorobenzyl | |
| 813 | $CH_3$ | 2,6-Dichlorobenzyl | |
| 814 | $CH_3$ | 2,4,6-Trichlorobenzyl | |
| 815 | $CH_3$ | 2-Trifluoromethyl-benzyl | |
| 816 | $CH_3$ | 3-Trifluoromethyl-benzyl | |
| 817 | $CH_3$ | 4-Trifluoromethyl-benzyl | |
| 818 | $CH_3$ | 2-Methoxybenzyl | |
| 819 | $CH_3$ | 4-Methoxybenzyl | |
| 820 | $CH_3$ | 4-tert.-Butoxybenzyl | |
| 821 | $CH_3$ | 4-Phenoxybenzyl | |
| 822 | $CH_3$ | 1-Phenethyl | |
| 823 | $CH_3$ | 2-Phenethyl | |
| 824 | $CH_3$ | 1-Phenylpropyl | |
| 825 | $CH_3$ | 2-Phenylpropyl | |
| 826 | $CH_3$ | 3-Phenylpropyl | |
| 827 | $CH_3$ | 2-Methyl-2-phenyl-propyl | |
| 828 | $CH_3$ | 2-Methyl-3-phenyl-propyl | |
| 829 | $CH_3$ | 4-Phenylbutyl | |
| 830 | $CH_3$ | 2-Phenyl-1-ethenyl | |
| 831 | $CH_3$ | 1-Phenyl-1-ethenyl | |
| 832 | $CH_3$ | 1-Phenyl-1-propenyl | |
| 833 | $CH_3$ | 1-Phenyl-1-propen-2-yl | |
| 834 | $CH_3$ | 2,2-Diphenylethenyl | |
| 835 | $CH_3$ | Phenoxymethyl | |
| 836 | $CH_3$ | 2-Pyridyl | |
| 837 | $CH_3$ | 3-Pyridyl | |
| 838 | $CH_3$ | 4-Pyridyl | |
| 839 | $CH_3$ | 2,6-Pyrimidinyl | |
| 840 | $CH_3$ | 1,5-Pyrimidinyl | |
| 841 | $CH_3$ | 2-Thienyl | |
| 842 | $CH_3$ | 3-Thienyl | |
| 843 | $CH_3$ | 2-Furyl | |

TABLE II-continued

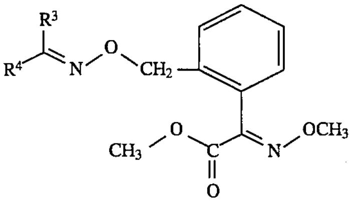

| No. | $R^3$ | $R^4$ | Data |
|---|---|---|---|
| 844 | $CH_3$ | 3-Furyl | |
| 845 | $CH_3$ | 1-Pyrrolyl | |
| 846 | $CH_3$ | 1-Imidazolyl | |
| 847 | $CH_3$ | 1,2,4-Triazolyl | |
| 848 | $CH_3$ | 1,3,4-Triazolyl | |
| 849 | $CH_3$ | 4-Thiazolyl | |
| 850 | $CH_3$ | 2-Benzothiazolyl | |
| 851 | $CH_3$ | 2-Pyridyloxy | |
| 852 | $CH_3$ | 2-Pyrimidinyloxy | |
| 853 | $CH_3$ | 2-Pyridylthio | |
| 854 | $CH_3$ | 2-Pyrimidinylthio | |
| 855 | $CH_3$ | 2-Benzothiazolylthio | |
| 856 | $CH_3$ | Phenylthiomethyl | |
| 857 | $CH_3$ | 2-Pyridylmethyl | |
| 858 | $CH_3$ | 3-Pyridylmethyl | |
| 859 | $CH_3$ | Furfuryloxy | |
| 860 | $CH_3$ | Thienylmethoxy | |
| 861 | $CH_3$ | 3-Isoxazolylmethoxy | |
| 862 | $CH_3$ | 2-Oxazolylmethoxy | |
| 863 | $CH_3$ | 2-Pyridylmethoxy | |
| 864 | $CH_3$ | 2'-Furyl-2-ethenyl | |
| 865 | $CH_3$ | 2'-Thienyl-2-ethenyl | |
| 866 | $CH_3$ | 3'-Pyridyl-2-ethenyl | |
| 867 | $CH_3$ | Oxiranyl | |
| 868 | $CH_3$ | 1-Aziridinyl | |
| 869 | $CH_3$ | 1-Azetidinyl | |
| 870 | $CH_3$ | 1-Pyrrolidinyl | |
| 871 | $CH_3$ | 2-Tetrahydrofuryl | |
| 872 | $CH_3$ | 2-Tetrahydropyranyl | |
| 873 | $CH_3$ | 3-Tetrahydropyranyl | |
| 874 | $CH_3$ | 1-Piperidinyl | |
| 875 | $CH_3$ | 1-Morpholinyl | |
| 876 | $CH_3$ | 1-Piperazinyl | |
| 877 | $CH_3$ | 1,3-Dioxan-2-yl | |
| 878 | $CH_3$ | 3-Tetrahydrothio-pyranyl | |
| 879 | $CH_3$ | 2-Dihydropyranyloxy | |
| 880 | $CH_3$ | 2-Tetrahydro-pyranyloxy | |
| 881 | $CH_3$ | $CF_3$ | |
| 882 | $CH_3$ | 2-Fluoroethyl | |
| 883 | $CH_3$ | 2,2,2-Trifluoroethyl | |
| 884 | $CH_3$ | Pentafluoroethyl | |
| 885 | $CH_3$ | Chloromethyl | |
| 886 | $CH_3$ | Dichloromethyl | |
| 887 | $CH_3$ | Trichloromethyl | |
| 888 | $CH_3$ | 2-Chloroethyl | |
| 889 | $CH_3$ | 2,2,2-Trichloroethyl | |
| 890 | $CH_3$ | Pentachloroethyl | |
| 891 | $CH_3$ | Cyclopropyl | |
| 892 | $CH_3$ | Cyclobutyl | |
| 893 | $CH_3$ | Cyclopentyl | |
| 894 | $CH_3$ | Cyclohexyl | |
| 895 | $CH_3$ | 1-Methylcyclopropyl | |
| 896 | $CH_3$ | 2,2-Dimethylcyclopropyl | |
| 897 | $CH_3$ | 1-Methylcyclohexyl | |
| 898 | $CH_3$ | 2,2-Difluorocyclopropyl- | |
| 899 | $CH_3$ | 2,2-Dichlorocyclopropyl | |
| 900 | $CH_3$ | 2,2-Dibromocyclopropyl | |
| 901 | $CH_3$ | 2,2-Dichloro-3-Methylcyclopropyl | |
| 902 | $CH_3$ | 2,2,3,3-Tetrafluoro-cyclobutyl | |
| 903 | $CH_3$ | Ethenyl | |
| 904 | $CH_3$ | 1-Propenyl | |
| 905 | $CH_3$ | 2-Methyl-1-propenyl | |
| 906 | $CH_3$ | 4-Methylpent-3-en-1-yl | |

TABLE II-continued

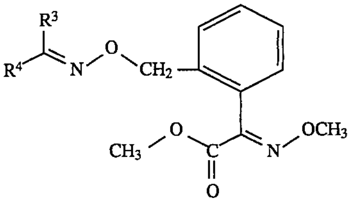

| No. | $R^3$ | $R^4$ | Data |
|---|---|---|---|
| 907 | $CH_3$ | 2-Propenyl | |
| 908 | $CH_3$ | 2-Butenyl | |
| 909 | $CH_3$ | 1-Methyl-2-propenyl | |
| 910 | $CH_3$ | 3-Methyl-2-butenyl | |
| 911 | $CH_3$ | 2,2-Difluoroethenyl | |
| 912 | $CH_3$ | 2,2-Dichloroethenyl | |
| 913 | $CH_3$ | 3,3,3-Trifluoropropenyl | |
| 914 | $CH_3$ | 3,3,3-Trichloropropenyl | |
| 915 | $CH_3$ | 3-Chloro-2-propenyl | |
| 916 | $CH_3$ | Cyclopent-1-enyl | |
| 917 | $CH_3$ | Cyclopentadienyl | |
| 918 | $CH_3$ | Cyclohex-1-enyl | |
| 919 | $CH_3$ | Pentafluorocyclo-pentadienyl | |
| 920 | $CH_3$ | Pentachlorocyclo-pentadienyl | |
| 921 | Phenyl | Phenyl | |
| 922 | Phenyl | 2-Fluorophenyl | |
| 923 | Phenyl | 4-Fluorophenyl | |
| 924 | Phenyl | 2-Chlorophenyl | |
| 925 | Phenyl | 3-Chlorophenyl | |
| 926 | Phenyl | 4-Chlorophenyl | |
| 927 | Phenyl | 3,4-Dichlorophenyl | |
| 928 | Phenyl | 4-Nitrophenyl | |
| 929 | Phenyl | 2-$CF_3$-Phenyl | |
| 930 | Phenyl | 3-$CF_3$-Phenyl | |
| 931 | Phenyl | 4-$CF_3$-Phenyl | |
| 932 | Phenyl | 2-Methylphenyl | |
| 933 | Phenyl | 3-Methylphenyl | |
| 934 | Phenyl | 4-Methylphenyl | |
| 935 | Phenyl | 2,4-Dimethylphenyl | |
| 936 | Phenyl | 4-tert.-Butylphenyl | |
| 937 | Phenyl | 4-Methoxyphenyl | |
| 938 | 4-Fluoro-phenyl | 4-Fluorophenyl | |
| 939 | 2-Fluoro-phenyl | 4-Fluorophenyl | |
| 940 | 2-Chloro-phenyl | 4-Fluorophenyl | |
| 941 | 2-Chloro-phenyl | 2-Chlorophenyl | |
| 942 | 3-Chloro-phenyl | 3-Chlorophenyl | |
| 943 | 4-Chloro-phenyl | 4-Chlorophenyl | |
| 944 | 2-Chloro-phenyl | 4-Chlorophenyl | |
| 945 | 4-Methoxy-phenyl | 4-Methoxyphenyl | |
| 946 | 4-Dimethyl-aminophenyl | 4-Dimethylamino-phenyl | |
| 947 | Phenyl | Naphthyl | |
| 948 | Ethyl | Ethyl | |
| 949 | Ethyl | n-Propyl | |
| 950 | Ethyl | iso-Propyl | |
| 951 | Ethyl | n-Butyl | |
| 952 | Ethyl | iso-Butyl | |
| 953 | Ethyl | 2-Methyl-butyl | |
| 954 | Ethyl | Benzyl | |
| 955 | n-Propyl | n-Propyl | |
| 956 | iso-Propyl | iso-Propyl | |
| 957 | n-Butyl | n-Butyl | |
| 958 | iso-Butyl | iso-Butyl | |
| 959 | tert.-Butyl | tert.-Butyl | |
| 960 | Benzyl | Benzyl | |
| 961 | Penta-chloroethyl | Pentachloroethyl | |

TABLE II-continued
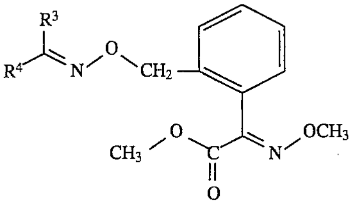
| No. | $R^3$ | $R^4$ | Data |
|---|---|---|---|
| 962 | n-Hexyl | n-Hexyl | |
| 963 | Ethoxy-carbonyl | Ethoxycarbonyl | |
| 964 | Phenyl | Benzoyl | |
| 965 | Ethyl | Phenyl | |
| 966 | n-Butyl | Phenyl | |
| 967 | Styryl | Styryl | |
| 968 | 2-Pyridyl | 2-Pyridyl | |
TABLE II-continued
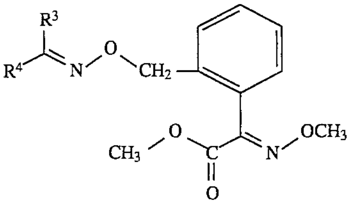
| No. | $R^3$ | $R^4$ | Data |
|---|---|---|---|
| 969 | 3-Pyridyl | 3-Pyridyl | |
| 970 | Ethyl | 2-Pyridyl | m.p.: 84–86° C. |
| 971 | 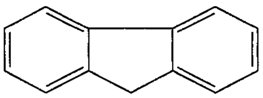 | | m.p.: 103–105° C. |

TABLE III

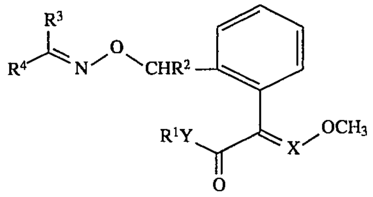

| No. | X | Y | $R^1$ | $R^2 = H$ | $R^3$ | $R^4$ | Data |
|---|---|---|---|---|---|---|---|
| 1 | $CHS-CH_3$ | O | $CH_3$ | | $CF_3$ | Phenyl | |
| 2 | $CHS-CH_3$ | O | $CH_3$ | | Cyclopropyl | Phenyl | |
| 3 | $CHS-CH_3$ | O | $CH_3$ | | Cyclopropyl | 4-Chlorophenyl | |
| 4 | $CHS-CH_3$ | O | $CH_3$ | | Cyclopropyl | 4-Methoxyphenyl | |
| 5 | $CHS-CH_3$ | O | $CH_3$ | | Cyclopropyl | 4-tert.-Butylphenyl | |
| 6 | $CHS-CH_3$ | O | $CH_3$ | | CN | Methylthio | |
| 7 | $CHS-CH_3$ | O | $CH_3$ | | CN | 2-Methoxyprop-2-yl | |
| 8 | $CHS-CH_3$ | O | $CH_3$ | | CN | 2-Methylthloprop-2-yl | |
| 9 | $CHS-CH_3$ | O | $CH_3$ | | CN | Phenylthio | |
| 10 | $CHS-CH_3$ | O | $CH_3$ | | CN | iso-Propyl | |
| 11 | $CHS-CH_3$ | O | $CH_3$ | | CN | CN | |
| 12 | $CHS-CH_3$ | O | $CH_3$ | | CN | Acetyl | |
| 13 | $CHS-CH_3$ | O | $CH_3$ | | CN | Benzoyl | |
| 14 | $CHS-CH_3$ | O | $CH_3$ | | CN | Methoxycarbonyl | |
| 15 | $CHS-CH_3$ | O | $CH_3$ | | CN | Phenyl | |
| 16 | $CHS-CH_3$ | O | $CH_3$ | | CN | 2-Chlorophenyl | |
| 17 | $CNS-CH_3$ | O | $CH_3$ | | CN | 4-Chlorophenyl | |
| 18 | $CHS-CH_3$ | O | $CH_3$ | | CN | 2-Methylphenyl | |
| 19 | $CHS-CH_3$ | O | $CH_3$ | | CN | 4-tert.-Butylphenyl | |
| 20 | $CHS-CH_3$ | O | $CH_3$ | | CN | 4-(n-Butoxylminomethyl)phenyl | |
| 21 | $CHS-CH_3$ | O | $CH_3$ | | CN | 2-Pyridyl | |
| 22 | $CNS-CH_3$ | O | $CH_3$ | | CN | Styryl | |
| 23 | $CHS-CH_3$ | O | $CH_3$ | | CN | 1-Propenyl | |
| 24 | $CHS-CH_3$ | O | $CH_3$ | | $CH_3$ | Phenylthio | |
| 25 | $CHS-CH_3$ | O | $CH_3$ | | $CH_3$ | Benzyl | |
| 26 | $CHS-CH_3$ | O | $CH_3$ | | $CH_3$ | tert.-Butyl | |
| 27 | $CHS-CH_3$ | O | $CH_3$ | | $CH_3$ | iso-Propyl | |
| 28 | $CHS-CH_3$ | O | $CH_3$ | | $CH_3$ | 2-Methylbutyl | |
| 29 | $CHS-CH_3$ | O | $CH_3$ | | $CH_3$ | iso-Butyl | |
| 30 | $CHS-CH_3$ | O | $CH_3$ | | $CH_3$ | Phenyl | |
| 31 | $CHS-CH_3$ | O | $CH_3$ | | $CH_3$ | 2-Chlorophenyl | |
| 32 | $CHS-CH_3$ | O | $CH_3$ | | $CH_3$ | 4-Chlorophenyl | |
| 33 | $CHS-CH_3$ | O | $CH_3$ | | $CH_3$ | 2-Methylphenyl | |
| 34 | $CHS-CH_3$ | O | $CH_3$ | | $CH_3$ | Naphthyl | |
| 35 | $CHS-CH_3$ | O | $CH_3$ | | $CH_3$ | 1-Pyridyl | |
| 36 | $CHS-CH_3$ | O | $CH_3$ | | iso-Butyl | iso-Butyl | |
| 37 | $CHS-CH_3$ | O | $CH_3$ | | Phenyl | Phenyl | |
| 38 | $CHS-CH_3$ | O | $CH_3$ | | $CH_2CH_2CH_2CH_2$ | | |
| 39 | $CHS-CH_3$ | O | $CH_3$ | | $CH_2CH_2CH_2CH_2CH_2$ | | |

TABLE III-continued

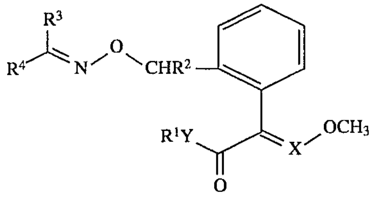

| | | | | | | |
|---|---|---|---|---|---|---|
| 40 | CH−$CH_3$ | O | $CH_3$ | $CF_3$ | Phenyl | |
| 41 | CH−$CH_3$ | O | $CH_3$ | Cyclopropyl | Phenyl | |
| 42 | CH−$CH_3$ | O | $CH_3$ | Cyclopropyl | 4-Chlorophenyl | |
| 43 | CH−$CH_3$ | O | $CH_3$ | Cyclopropyl | 4-Methoxyphenyl | |
| 44 | CH−$CH_3$ | O | $CH_3$ | Cyclopropyl | 4-tert.-Butylphenyl | |
| 45 | CH−$CH_3$ | O | $CH_3$ | CN | Methylthio | |
| 46 | CH−$CH_3$ | O | $CH_3$ | CN | 2-Methoxyprop-2-yl | IR (film): 1717,13 36,1367,1256,1210,1179, 1070,1037,1009,759 |
| 47 | CH−$CH_3$ | O | $CH_3$ | CN | 2-Methylthloprop-2-yl | $^1$H-NMR ($CDCl_3$): δ = 1.45s, 1.6d, 1.8s, 3.7s, 5.1s, 7.1–7.5m |
| 48 | CH−$CH_3$ | O | $CH_3$ | CN | Phenylthio | |
| 49 | CH−$CH_3$ | O | $CH_3$ | CN | iso-Propyl | $^1$H-NMR ($CDCl_3$): δ = 1.2d, 1.6d, 2.7m, 3.67s, 5.1s, 7.0–7.5m |
| 50 | CH−$CH_3$ | O | $CH_3$ | CN | CN | |
| 51 | CH−$CH_3$ | O | $CH_3$ | CN | Acetyl | |
| 52 | CH−$CH_3$ | O | $CH_3$ | CN | Benzoyl | |
| 53 | CH−$CH_3$ | O | $CH_3$ | CN | Methoxycarbonyl | |
| 54 | CH−$CH_3$ | O | $CH_3$ | CN | Phenyl | $^1$H-NMR ($CDCl_3$): δ = 1.6d, 3.7s, 5.2s, 7.0–1.8m |
| 55 | CH−$CH_3$ | O | $CH_3$ | CN | 2-Chlorophenyl | |
| 56 | CH−$CH_3$ | O | $CH_3$ | CN | 4-Chlorophenyl | |
| 57 | CH−$CH_3$ | O | $CH_3$ | CN | 2-Methylphenyl | |
| 58 | CH−$CH_3$ | O | $CH_3$ | CN | 4-tert.-Butylphenyl | |
| 59 | CH−$CH_3$ | O | $CH_3$ | CN | 4-(n-Butoxylmlnomethyl)phenyl | |
| 60 | CH−$CH_3$ | O | $CH_3$ | CN | 2-Pyridyl | |
| 61 | CH−$CH_3$ | O | $CH_3$ | CN | Styryl | |
| 62 | CH−$CH_3$ | O | $CH_3$ | CN | 1-Propenyl | |
| 63 | CH−$CH_3$ | O | $CH_3$ | $CH_3$ | Phenylthio | |
| 64 | CH−$CH_3$ | O | $CH_3$ | $CH_3$ | Benzyl | |
| 65 | CH−$CH_3$ | O | $CH_3$ | $CH_3$ | tert.-Butyl | |
| 66 | CH−$CH_3$ | O | $CH_3$ | $CH_3$ | iso-Propyl | |
| 67 | CH−$CH_3$ | O | $CH_3$ | $CH_3$ | 2-Methylbutyl | |
| 68 | CH−$CH_3$ | O | $CH_3$ | $CH_3$ | iso-Butyl | |
| 69 | CH−$CH_3$ | O | $CH_3$ | $CH_3$ | Phenyl | |
| 70 | CH−$CH_3$ | O | $CH_3$ | $CH_3$ | 2-Chlorophenyl | |
| 71 | CH−$CH_3$ | O | $CH_3$ | $CH_3$ | 4-Chlorophenyl | IR (film): 1716,13 90,13 34,1253,1206,1096, 1036,1012,820,760 |
| 72 | CH−$CH_3$ | O | $CH_3$ | $CH_3$ | 2-Methylphenyl | |
| 73 | CH−$CH_3$ | O | $CH_3$ | $CH_3$ | Naphthyl | |
| 74 | CH−$CH_3$ | O | $CH_3$ | $CH_3$ | 1-Pyridyl | |
| 75 | CH−$CH_3$ | O | $CH_3$ | iso-Butyl | iso-Butyl | |
| 76 | CH−$CH_3$ | O | $CH_3$ | Phenyl | Phenyl | |
| 77 | CH−$CH_3$ | O | $CH_3$ | $CH_2CH_2CH_2CH_2$ | | |

TABLE III-continued

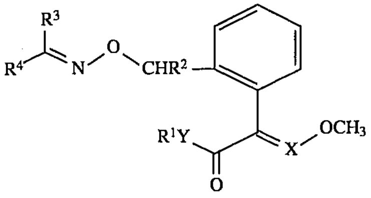

| | | | | | |
|---|---|---|---|---|---|
| 78 | $CH-CH_3$ | O | $CH_3$ | $CH_2CH_2CH_2CH_2CH_2$ | |
| 79 | $CH_2$ | O | $CH_3$ | $CF_3$ | Phenyl |
| 80 | $CH_2$ | O | $CH_3$ | Cyclopropyl | Phenyl |
| 81 | $CH_2$ | O | $CH_3$ | Cyclopropyl | 4-Chlorophenyl |
| 82 | $CH_2$ | O | $CH_3$ | Cyclopropyl | 4-Methoxyphenyl |
| 83 | $CH_2$ | O | $CH_3$ | Cyclopropyl | 4-tert.-Butylphenyl |
| 84 | $CH_2$ | O | $CH_3$ | CN | Methylthio |
| 85 | $CH_2$ | O | $CH_3$ | CN | 2-Methoxyprop-2-yl |
| 86 | $CH_2$ | O | $CH_3$ | CN | 2-Methylthloprop-2-yl |
| 87 | $CH_2$ | O | $CH_3$ | CN | Phenylthio |
| 88 | $CH_2$ | O | $CH_3$ | CN | iso-Propyl |
| 89 | $CH_2$ | O | $CH_3$ | CN | CN |
| 90 | $CH_2$ | O | $CH_3$ | CN | Acetyl |
| 91 | $CH_2$ | O | $CH_3$ | CN | Benzoyl |
| 92 | $CH_2$ | O | $CH_3$ | CN | Methoxycarbonyl |
| 93 | $CH_2$ | O | $CH_3$ | CN | Phenyl |
| 94 | $CH_2$ | O | $CH_3$ | CN | 2-Chlorophenyl |
| 95 | $CH_2$ | O | $CH_3$ | CN | 4-Chlorophenyl |
| 96 | $CH_2$ | O | $CH_3$ | CN | 2-Methylphenyl |
| 97 | $CH_2$ | O | $CH_3$ | CN | 4-tert.-Butylphenyl |
| 98 | $CH_2$ | O | $CH_3$ | CN | 4-(n-Butoxylminomethyl)phenyl |
| 99 | $CH_2$ | O | $CH_3$ | CN | 2-Pyridyl |
| 100 | $CH_2$ | O | $CH_3$ | CN | Styryl |
| 101 | $CH_2$ | O | $CH_3$ | CN | 1-Propenyl |
| 102 | $CH_2$ | O | $CH_3$ | $CH_3$ | Phenylthio |
| 103 | $CH_2$ | O | $CH_3$ | $CH_3$ | Benzyl |
| 104 | $CH_2$ | O | $CH_3$ | $CH_3$ | tert.-Butyl |
| 105 | $CH_2$ | O | $CH_3$ | $CH_3$ | iso-Propyl |
| 106 | $CH_2$ | O | $CH_3$ | $CH_3$ | 2-Methylbutyl |
| 107 | $CH_2$ | O | $CH_3$ | $CH_3$ | iso-Butyl |
| 108 | $CH_2$ | O | $CH_3$ | $CH_3$ | Phenyl |
| 109 | $CH_2$ | O | $CH_3$ | $CH_3$ | 2-Chlorophenyl |
| 110 | $CH_2$ | O | $CH_3$ | $CH_3$ | 4-Chlorophenyl |
| 111 | $CH_2$ | O | $CH_3$ | $CH_3$ | 2-methylphenyl |
| 112 | $CH_2$ | O | $CH_3$ | $CH_3$ | Naphthyl |
| 113 | $CH_2$ | O | $CH_3$ | $CH_3$ | 1-Pyridyl |
| 114 | $CH_2$ | O | $CH_3$ | iso-Butyl | iso-Butyl |
| 115 | $CH_2$ | O | $CH_3$ | Phenyl | Phenyl |
| 116 | $CH_2$ | O | $CH_3$ | $CH_2CH_2CH_2CH_2$ | |
| 117 | $CH_2$ | O | $CH_3$ | $CH_2CH_2CH_2CH_2CH_2$ | |
| 118 | $N-OCH_3$ | S | $CH_3$ | $CF_3$ | Phenyl |
| 119 | $N-OCH_3$ | S | $CH_3$ | Cyclopropyl | Phenyl |

TABLE III-continued

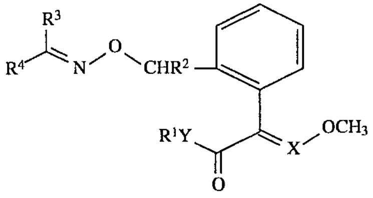

| No. | X | Y | $R^2$ | $R^3$ | $R^4$ | Data |
|---|---|---|---|---|---|---|
| 120 | $N-OCH_3$ | S | $CH_3$ | Cyclopropyl | 4-Chlorophenyl | |
| 121 | $N-OCH_3$ | S | $CH_3$ | Cyclopropyl | 4-Methoxyphenyl | |
| 122 | $N-OCH_3$ | S | $CH_3$ | Cyclopropyl | 4-tert.-Butylphenyl | |
| 123 | $N-OCH_3$ | S | $CH_3$ | CN | Methylthio | |
| 124 | $N-OCH_3$ | S | $CH_3$ | CN | 2-Methoxyprop-2-yl | |
| 125 | $N-OCH_3$ | S | $CH_3$ | CN | 2-Methylthioprop-2-yl | |
| 126 | $N-OCH_3$ | S | $CH_3$ | CN | Phenylthio | |
| 127 | $N-OCH_3$ | S | $CH_3$ | CN | iso-Propyl | |
| 128 | $N-OCH_3$ | S | $CH_3$ | CN | CN | |
| 129 | $N-OCH_3$ | S | $CH_3$ | CN | Acetyl | |
| 130 | $N-OCH_3$ | S | $CH_3$ | CN | Benzoyl | |
| 131 | $N-OCH_3$ | S | $CH_3$ | CN | Methoxycarbonyl | |
| 132 | $N-OCH_3$ | S | $CH_3$ | CN | Phenyl | |
| 133 | $N-OCH_3$ | S | $CH_3$ | CN | 2-Chlorophenyl | |
| 134 | $N-OCH_3$ | S | $CH_3$ | CN | 4-Chlorophenyl | |
| 135 | $N-OCH_3$ | S | $CH_3$ | CN | 2-Methylphenyl | |
| 136 | $N-OCH_3$ | S | $CH_3$ | CN | 4-tert.-Butylphenyl | |
| 137 | $N-OCH_3$ | S | $CH_3$ | CN | 4-(n-Butoxylminomethyl)phenyl | |
| 138 | $N-OCH_3$ | S | $CH_3$ | CN | 2-Pyridyl | |
| 139 | $N-OCH_3$ | S | $CH_3$ | CN | Styryl | |
| 140 | $N-OCH_3$ | S | $CH_3$ | CN | 1-Propenyl | |
| 141 | $N-OCH_3$ | S | $CH_3$ | $CH_3$ | Phenylthio | |
| 142 | $N-OCH_3$ | S | $CH_3$ | $CH_3$ | Benzyl | |
| 143 | $N-OCH_3$ | S | $CH_3$ | $CH_3$ | tert.-Butyl | |
| 144 | $N-OCH_3$ | S | $CH_3$ | $CH_3$ | iso-Propyl | |
| 145 | $N-OCH_3$ | S | $CH_3$ | $CH_3$ | 2-Methylbutyl | |
| 146 | $N-OCH_3$ | S | $CH_3$ | $CH_3$ | iso-Butyl | |
| 147 | $N-OCH_3$ | S | $CH_3$ | $CH_3$ | Phenyl | |
| 148 | $N-OCH_3$ | S | $CH_3$ | $CH_3$ | 2-Chlorophenyl | |
| 149 | $N-OCH_3$ | S | $CH_3$ | $CH_3$ | 4-Chlorophenyl | |
| 150 | $N-OCH_3$ | S | $CH_3$ | $CH_3$ | 2-Methylphenyl | |
| 151 | $N-OCH_3$ | S | $CH_3$ | $CH_3$ | Naphthyl | |
| 152 | $N-OCH_3$ | S | $CH_3$ | $CH_3$ | 1-Pyridyl | |
| 153 | $N-OCH_3$ | S | $CH_3$ | iso-Butyl | iso-Butyl | |
| 154 | $N-OCH_3$ | S | $CH_3$ | Phenyl | Phenyl | |
| 155 | $N-OCH_3$ | S | $CH_3$ | $CH_2CH_2CH_2CH_2$ | | |
| 156 | $N-OCH_3$ | S | $CH_3$ | $CH_2CH_2CH_2CH_2CH_2$ | | |
| 157 | $N-OCH_3$ | NH | $CH_3$ | $CF_3$ | Phenyl | |
| 158 | $N-OCH_3$ | NH | $CH_3$ | Cyclopropyl | Phenyl | |
| 159 | $N-OCH_3$ | NH | $CH_3$ | Cyclopropyl | 4-Chlorophenyl | m.p.: 71–74° C. IR (KBr): 3348,1663,1529,1042,1030,982 |
| 160 | $N-OCH_3$ | NH | $CH_3$ | Cyclopropyl | 4-Methoxyphenyl | |

TABLE III-continued

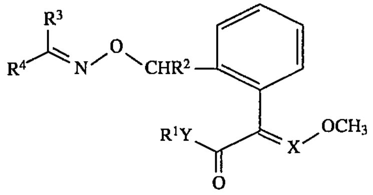

| No. | X | Y | $R^1$ | $R^2$ | $R^3$ | $R^4$ | Data |
|---|---|---|---|---|---|---|---|
| 161 | $N-OCH_3$ | NH | $CH_3$ | | Cyclopropyl | 4-tert.-Butylphenyl | |
| 162 | $N-OCH_3$ | NH | $CH_3$ | | CN | Methylthio | |
| 163 | $N-OCH_3$ | NH | $CH_3$ | | CN | 2-Methoxyprop-2-yl | |
| 164 | $N-OCH_3$ | NH | $CH_3$ | | CN | 2-Methylthioprop-2-yl | |
| 165 | $N-OCH_3$ | NH | $CH_3$ | | CN | Phenylthio | |
| 166 | $N-OCH_3$ | NH | $CH_3$ | | CN | iso-Propyl | |
| 167 | $N-OCH_3$ | NH | $CH_3$ | | CN | CN | |
| 168 | $N-OCH_3$ | NH | $CH_3$ | | CN | Acetyl | |
| 169 | $N-OCH_3$ | NH | $CH_3$ | | CN | Benzoyl | |
| 170 | $N-OCH_3$ | NH | $CH_3$ | | CN | Methoxycarbonyl | |
| 171 | $N-OCH_3$ | NH | $CH_3$ | | CN | Phenyl | |
| 172 | $N-OCH_3$ | NH | $CH_3$ | | CN | 2-Chlorophenyl | |
| 173 | $N-OCH_3$ | NH | $CH_3$ | | CN | 4-Chlorophenyl | |
| 174 | $N-OCH_3$ | NH | $CH_3$ | | CN | 2-Methylphenyl | |
| 175 | $N-OCH_3$ | NH | $CH_3$ | | CN | 4-tert.-Butylphenyl | |
| 176 | $N-OCH_3$ | NH | $CH_3$ | | CN | 4-(n-Butoxyiminomethyl)phenyl | |
| 177 | $N-OCH_3$ | NH | $CH_3$ | | CN | 2-Pyridyl | |
| 178 | $N-OCH_3$ | NH | $CH_3$ | | CN | Styryl | |
| 179 | $N-OCH_3$ | NH | $CH_3$ | | CN | 1-Propenyl | |
| 180 | $N-OCH_3$ | NH | $CH_3$ | | $CH_3$ | Phenylthio | |
| 181 | $N-OCH_3$ | NH | $CH_3$ | | $CH_3$ | Benzyl | |
| 182 | $N-OCH_3$ | NH | $CH_3$ | | $CH_3$ | tert.-Butyl | |
| 183 | $N-OCH_3$ | NH | $CH_3$ | | $CH_3$ | iso-Propyl | |
| 184 | $N-OCH_3$ | NH | $CH_3$ | | $CH_3$ | 2-Methylbutyl | |
| 185 | $N-OCH_3$ | NH | $CH_3$ | | $CH_3$ | iso-Butyl | |
| 186 | $N-OCH_3$ | NH | $CH_3$ | | $CH_3$ | Phenyl | |
| 187 | $N-OCH_3$ | NH | $CH_3$ | | $CH_3$ | 2-Chlorophenyl | |
| 188 | $N-OCH_3$ | NH | $CH_3$ | | $CH_3$ | 4-Chlorophenyl | m.p.: 119–121° C.<br>IR (KOr): 3421,1676,1037,985,933,752 |
| 189 | $N-OCH_3$ | NH | $CH_3$ | | $CH_3$ | 2-Methylphenyl | |
| 190 | $N-OCH_3$ | NH | $CH_3$ | H | $CH_3$ | Naphthyl | |
| 191 | $N-OCH_3$ | NH | $CH_3$ | H | $CH_3$ | 1-Pyridyl | |
| 192 | $N-OCH_3$ | NH | $CH_3$ | H | iso-Butyl | iso-Butyl | |
| 193 | $N-OCH_3$ | NH | $CH_3$ | H | Phenyl | Phenyl | |
| 194 | $N-OCH_3$ | NH | $CH_3$ | H | | $CH_2CH_2CH_2CH_2$ | |
| 195 | $N-OCH_3$ | NH | $CH_3$ | H | | $CH_2CH_2CH_2CH_2CH_2$ | |
| 196 | $N-OCH_3$ | O | $C_2H_5$ | H | $CH_3$ | Phenyl | |
| 197 | $CH-OCH_3$ | O | $C_2H_5$ | H | $CH_3$ | Phenyl | |
| 198 | $N-OCH_3$ | O | $n-C_3H_5$ | H | $CH_3$ | Phenyl | |

TABLE III-continued

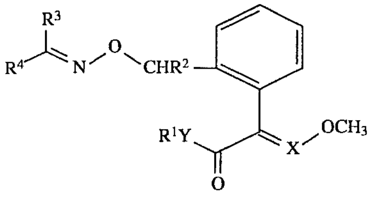

| No. | X | Y | $R^1$ | $R^2$ | $R^3$ | $R^4$ | Data |
|---|---|---|---|---|---|---|---|
| 199 | $CHOCH_3$ | O | n-$C_3H_5$ | H | $CH_3$ | Phenyl | |
| 200 | $CHC_2H_5$ | O | $CH_3$ | H | $CH_3$ | Phenyl | |
| 201 | $N-OCH_3$ | O | $CH_3$ | $CH_3$ | $CH_3$ | Phenyl | |
| 202 | $CHOCH_3$ | O | $CH_3$ | $CH_3$ | $CH_3$ | Phenyl | |
| 203 | $N-OCH_3$ | O | $CH_3$ | $CH_3$ | CN | Phenyl | |
| 204 | $CHOCH_3$ | O | $CH_3$ | $CH_3$ | CN | Phenyl | |
| 205 | $CHS-CH_3$ | O | $CH_3$ | H | H | Phenyl | |
| 206 | $CH-CH_3$ | O | $CH_3$ | H | H | Phenyl | |
| 207 | $CH_2$ | O | $CH_3$ | H | H | Phenyl | |
| 208 | $NOCH_3$ | S | $CH_3$ | H | H | Phenyl | |
| 209 | $CHOCH_3$ | S | $CH_3$ | H | H | Phenyl | |
| 210 | $CHOCH_3$ | NH | $CH_3$ | H | H | Phenyl | |
| 211 | $NOCH_3$ | NH | $CH_3$ | H | H | Phenyl | |
| 212 | $CH-OCH_3$ | S | $CH_3$ | H | CN | Methylthio | |
| No. | X | Y | $R^1$ | $R^2$ = H | $R^3$ | $R^4$ | Data |
| 213 | $CH-OCH_3$ | S | $CH_3$ | | CN | 2-Methoxyprop-2-yl | |
| 214 | $CH-OCH_3$ | S | $CH_3$ | | CN | 2-Methylthloprop-2-yl | |
| 215 | $CH-OCH_3$ | S | $CH_3$ | | CN | Phenylthio | |
| 216 | $CH-OCH_3$ | S | $CH_3$ | | CN | iso-Propyl | |
| 217 | $CH-OCH_3$ | S | $CH_3$ | | CN | CN | |
| 218 | $CH-OCH_3$ | S | $CH_3$ | | CN | Acthyl | |
| 219 | $CH-OCH_3$ | S | $CH_3$ | | CN | Benzoyl | |
| 220 | $CH-OCH_3$ | S | $CH_3$ | | CN | Methoxycarbonyl | |
| 221 | $CH-OCH_3$ | S | $CH_3$ | | CN | Phenyl | |
| 222 | $CH-OCH_3$ | S | $CH_3$ | | CN | 2-Chlorophenyl | |
| 223 | $CH-OCH_3$ | S | $CH_3$ | | CN | 4-Chlorophenyl | |
| 224 | $CH-OCH_3$ | S | $CH_3$ | | CN | 2-methylphenyl | |
| 225 | $CH-OCH_3$ | S | $CH_3$ | | CN | 4-tert.-Butylphenyl | |
| 226 | $CH-OCH_3$ | S | $CH_3$ | | CN | 4-(n-Butoxyiminomethyl)phenyl | |
| 227 | $CH-OCH_3$ | S | $CH_3$ | | CN | 2-Pyridyl | |
| 228 | $CH-OCH_3$ | S | $CH_3$ | | CN | Styryl | |
| 229 | $CH-OCH_3$ | S | $CH_3$ | | CN | 1-Propenyl | |
| 230 | $CH-OCH_3$ | NH | $CH_3$ | | CN | Methylthio | |
| 231 | $CH-OCH_3$ | NH | $CH_3$ | | CN | 2-Methoxyprop-2-yl | |
| 232 | $CH-OCH_3$ | NH | $CH_3$ | | CN | 2-Methylthioprop-2-yl | |
| 233 | $CH-OCH_3$ | NH | $CH_3$ | | CN | Phenylthio | |
| 234 | $CH-OCH_3$ | NH | $CH_3$ | | CN | iso-Propyl | |
| 235 | $CH-OCH_3$ | NH | $CH_3$ | | CN | CN | |
| 236 | $CH-OCH_3$ | NH | $CH_3$ | | CN | Acthyl | |
| 237 | $CH-OCH_3$ | NH | $CH_3$ | | CN | Benzoyl | |

TABLE III-continued

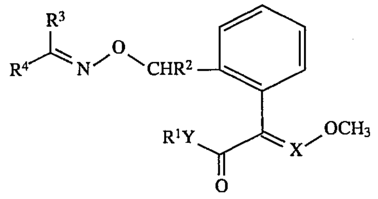

| | | | | | | |
|---|---|---|---|---|---|---|
| 238 | $CH-OCH_3$ | NH | $CH_3$ | CN | Methoxycarbonyl | |
| 239 | $CH-OCH_3$ | NH | $CH_3$ | CN | Phenyl | |
| 240 | $CH-OCH_3$ | NH | $CH_3$ | CN | 2-Chlorophenyl | |
| 241 | $CH-OCH_3$ | NH | $CH_3$ | CN | 4-Chlorophenyl | |
| 242 | $CH-OCH_3$ | NH | $CH_3$ | CN | 2-Methylphenyl | |
| 243 | $CH-OCH_3$ | NH | $CH_3$ | CN | 4-tert.-Butylphenyl | |
| 244 | $CH-OCH_3$ | NH | $CH_3$ | CN | 4-(n-Butoxyliminomethyl)phenyl | |
| 245 | $CH-OCH_3$ | NH | $CH_3$ | CN | 2-Pyridyl | |
| 246 | $CH-OCH_3$ | NH | $CH_3$ | CN | Styryl | |
| 247 | $CH-OCH_3$ | NH | $CH_3$ | CN | 1-Propenyl | |
| 248 | $N-OCH_3$ | NH | $CH_3$ | $CH_3$ | 3-Chlorphenyl | m.p.: 71–74° C.; |
| 249 | $N-OCH_3$ | NH | $CH_3$ | $CH_3$ | 3,5-Dichlorphenyl | m.p.: 94–97° C.; |
| 250 | $N-OCH_3$ | NH | $CH_3$ | $CH_3$ | 2,3,4-Trichlorphenyl | m.p.: 110–112° C.; |
| 251 | $N-OCH_3$ | NH | $CH_3$ | $CH_3$ | 3-Gromphenyl | m.p.: 74–77° C.; |
| 252 | $N-OCH_3$ | NH | $CH_3$ | $CH_3$ | 4-Methylphenyl | m.p.: 69–72° C.; |
| 253 | $N-OCH_3$ | NH | $CH_3$ | $CH_3$ | 4-Nitrophenyl | m.p.: 134–137° C.; |
| 254 | $CH-CH_3$ | O | $CH_3$ | CN | 2-Ethoxy-prop-2-yl | IR (film): 2982,1717,13 36,1255,1210,1192,1067,1037,1010 |
| 255 | $CH-CH_3$ | O | $CH_3$ | CN | 2-i-Propoxy-prop-2-yl | IR (film): 2983,1718,1383,1370,1255,1173,1119,1109,1037,1002 |
| 256 | $CH-CH_3$ | O | $CH_3$ | CN | 2-n-Butoxy-prop-2-yl | IR (film): 2957,1718,13 35,1255,1176,1036,1010,759 |
| 257 | $CH-CH_3$ | O | $CH_3$ | CN | 2-1-Butoxy-prop-2-yl | IR (film): 2956,1717,13 35,1366,1255,1209,1176,1064,1037,1008 |
| 258 | $CH-CH_3$ | O | $CH_3$ | CN | Cyclopropyl | $^1$H-NMR ($CDCl_3$): δ = 0.9m, 1.6d, 2.3m, 3.67s, 5.15s, 7.05–7.4m |
| 259 | $CH-CH_3$ | O | $CH_3$ | CN | 2-Ethylthio-prop-2-yl | $^1$H-NMR ($CDCl_3$): δ = 1.1t, 1.5s, 1.6d, 2.2q, 3.7s, 5.1s, 7.1–7.5m |
| 260 | $CH-CH_3$ | O | $CH_3$ | CN | 2-1-Propylthio-pro-2-yl | $^1$H-NMR ($CDCl_3$): δ = 1.15s, 1.5s, 1.6d, 2.6m, 3.7s, 5.1s, 7.1–7.5m |
| 261 | $CH-CH_3$ | O | $CH_3$ | CN | 2-Tetrahydropyranyl | $^1$H-NMR ($CDCl_3$): δ = 1.4–1.9m, 1.6d, 3.5m, 3.7s, 4.1m, 5.1s, 7.0–7.5m |

TABLE IV

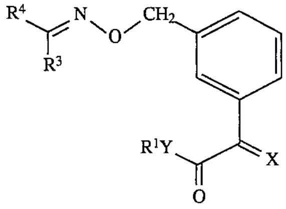

| No. | X | Y | $R^1$ | $R^3$ | $R^4$ | Data |
|---|---|---|---|---|---|---|
| 1 | $CH-OCH_3$ | O | $CH_3$ | $CH_3$ | Phenyl | |
| 2 | $CH-OCH_3$ | O | $CH_3$ | $CH_3$ | 3-Bromophenyl | |
| 3 | $CH-OCH_3$ | O | $CH_3$ | $CH_3$ | 4-Phenoxyphenyl | |
| 4 | $CH-OCH_3$ | O | $CH_3$ | $CH_3$ | 4-Cyclohexylphenyl | |
| 5 | $NOCH_3$ | O | $CH_3$ | $CH_3$ | Phenyl | |
| 6 | $NOCH_3$ | O | $CH_3$ | $CH_3$ | 3-Bromophenyl | oil; IR (film): 1727,1436,1312,1240,1032 |
| 7 | $NOCH_3$ | O | $CH_3$ | $CH_3$ | 4-Phenoxyphenyl | oil; IR (film): 1727,1489,1239,1031,683 |
| 8 | $NOCH_3$ | O | $CH_3$ | $CH_3$ | 4-Cyclohexylphenyl | oil; IR (film): 2925,1728,1447,1239,1164,1077,1032 |
| 9 | $CHOCH_3$ | O | $CH_3$ | CN | Iso-Propyl | oil; IR (film): 2970,2220,1710,1127 |
| 10 | $CHOCH_3$ | O | $CH_3$ | CN | 2-Methoxyprop-2-yl | oil; IR (film): 2980,2220,1710,1127 |
| 11 | $CHOCH_3$ | O | $CH_3$ | CN | 2-Methylthloprop-2-yl | oil; IR (film): 2980,2220,1709,1127 |
| 12 | $CHOCH_3$ | O | $CH_3$ | CN | 2-Tetrahydrofuranyl | oil; IR (film): 2945,2850,2220,1709,1127 |
| 13 | $CHOCH_3$ | O | $CH_3$ | CN | Phenyl | oil; IR (film): 2940,2220,1709,1127,1030 |

TABLE V

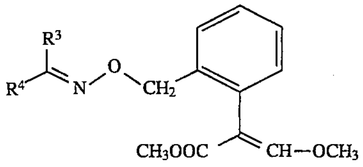

| No. | $R^3$ | $R^4$ | Data |
|---|---|---|---|
| 1 | H | H | |
| 2 | H | Methoxymethyl | |
| 3 | H | Ethoxymethyl | |
| 4 | H | n-Propoxymethyl | |
| 5 | H | iso-Propoxymethyl | |
| 6 | H | tert.-Butoxymethyl | |
| 7 | H | 2-Methoxyprop-2-yl | |
| 8 | H | 2-Ethoxyprop-2-yl | |
| 9 | H | 2-n-Propoxyprop-2-yl | |
| 10 | H | 2-iso-Propoxyprop-2-yl | |
| 11 | H | 2-tert.-Butoxyprop-2-yl | |
| 12 | H | Methylthiomethyl | |
| 13 | H | tert.-Butylthiomethyl | |
| 14 | H | 2-Methylthioprop-2-yl | |
| 15 | H | 2-iso-Propylthioprop-2-yl | |
| 16 | H | 2-tert.-Butylthioprop-2-yl | |
| 17 | H | Methyl | |
| 18 | H | Ethyl | |
| 19 | H | n-Propyl | |
| 20 | H | iso-Propyl | |
| 21 | H | n-Butyl | |
| 22 | H | iso-Butyl | |
| 23 | H | sec.-Butyl | |
| 24 | H | tert.-Butyl | |
| 25 | H | n-Hexyl | |
| 26 | H | n-Decyl | |
| 27 | H | Cyclopropyl | |
| 28 | H | Cyclohexyl | |
| 29 | H | Phenylthiomethyl | |
| 30 | H | 2-Phenylthiomethyl | |
| 31 | H | 2-(2'-Chlorophonylthio)prop-2-yl | |
| 32 | H | Ethynyl | |
| 33 | H | 1-Propynyl | |
| 34 | H | Methoxy | |
| 35 | H | Ethoxy | |
| 36 | H | n-Propoxy | |
| 37 | H | iso-Propoxy | |
| 38 | H | n-Butoxy | |
| 39 | H | iso-Butoxy | |
| 40 | H | sec.-Butoxy | |
| 41 | H | tert.-Butoxy | |
| 42 | H | Methylthio | |
| 43 | H | Ethylthio | |
| 44 | H | n-Propylthio | |
| 45 | H | iso-Propylthio | |
| 46 | H | n-Butylthio | |
| 47 | H | iso-Butylthio | |
| 48 | H | sec.-Butylthio | |
| 49 | H | tert.-Butylthio | |
| 50 | H | Benzylthio | |
| 51 | H | Trifluoromethoxy | |
| 52 | H | Cyano | |
| 53 | H | Amino | |
| 54 | H | Methylamino | |
| 55 | H | Dimethylamino | |
| 56 | H | Ethylamino | |
| 57 | H | Diethylamino | |
| 58 | H | Di-n-Propylamino | |
| 59 | H | Di-iso-Propylamino | |
| 60 | H | Di-n-Butylamino | |
| 61 | H | Di-iso-Butylamino | |
| 62 | H | Acetyl | |
| 63 | H | Propion-1-yl | |
| 64 | H | Butyr-1-yl | |
| 65 | H | iso-Butyr-1-yl | |
| 66 | H | Pivaloyl | |
| 67 | H | Benzoyl | |
| 68 | H | 4-Chlorobenzoyl | |

TABLE V-continued

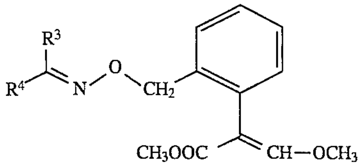

| No. | $R^3$ | $R^4$ | Data |
|---|---|---|---|
| 69 | H | Benzylcarbonyl | |
| 70 | H | Methoxycarbonyl | |
| 71 | H | Ethoxycarbonyl | |
| 72 | H | n-Propoxycarbonyl | |
| 73 | H | iso-Propoxycarbonyl | |
| 74 | H | n-Butoxycarbonyl | |
| 75 | H | iso-Butoxycarbonyl | |
| 76 | H | sec.-Butoxycarbonyl | |
| 77 | H | tert.-Butoxycarbonyl | |
| 78 | H | n-Hexoxycarbonyl | |
| 79 | H | Phenoxycarbonyl | |
| 80 | H | 4-Chlorphenoxycarbonyl | |
| 81 | H | Benzyloxycarbonyl | |
| 82 | H | Aminocarbonyl | |
| 83 | H | Dimethylaminocarbonyl | |
| 84 | H | Diethylaminocarbonyl | |
| 85 | H | Di-iso-Propylaminocarbonyl | |
| 86 | H | Phenylaminocarbonyl | |
| 87 | H | N-Methyl-N-Phenylaminocarbonyl | |
| 88 | H | Phenyl | |
| 89 | H | 2-Fluorophenyl | m.p.: 69–71° C.; |
| 90 | H | 3-Fluorophenyl | m.p.: 74–77° C.; |
| 91 | H | 4-Fluorophenyl | m.p.: 73–76° C.; IR (KBr): 1699, 1278,1271,1256,1225 |
| 92 | H | Pentafluarophenyl | m.p.: 94–96° C.; IR (KBr): 1704, 1527,1494,1133 |
| 93 | H | 2-Chlorophenyl | $^1$H-NMR($CDCl_3$3): δ = 3.70s, 3.82s, 5.15s, 7.15–7.40m, 7.52m, 7.60s, 7.85m, 8.52s |
| 94 | H | 3-Chlorophenyl | m.p.: 48–50° C.; |
| 95 | H | 4-Chlorophenyl | (v. Exaample 6) |
| 96 | H | Pentachlorophenyl | |
| 97 | H | 2,3-Dichlorophenyl | m.p.: 103–105° C.; |
| 98 | H | 2,4-Dtchlorophenyl | m.p.: 94–96° C.; |
| 99 | H | 2,5-Dichlorophenyl | |
| 100 | H | 2,6-Dichlorophenyl | m.p.: 118–120° C.; |
| 101 | H | 3,4-Dichlorophenyl | m.p.: 82–84° C.; |
| 102 | H | 3,5-Dichlorophenyl | m.p.: 94–96° C.; |
| 103 | H | 2,3,4-Trichlorophenyl | |
| 104 | H | 2,3,5-Trichlorophenyl | |
| 105 | H | 2,3,6-Trichlorophenyl | |
| 106 | H | 2,4,5-Trichlorophenyl | |
| 107 | H | 2,4,6-Trichlorophenyl | |
| 108 | H | 3,4,5-Trichlorophenyl | |
| 109 | H | 2,3,4,6-Tetrachlorophenyl | |
| 110 | H | 2,3,5,6-Tetrachlorophenyl | |
| 111 | H | 2-Bromophenyl | m.p.: 85–87° C.; |
| 112 | H | 3-Bromophenyl | $^1$H-NMR ($CDCl_3$): δ = 3.68s, 3.79s, 5.13, 7.15–7.54m, 7.59s 7.74s, 8.00s |
| 113 | H | 4-Bromophenyl | m.p.: 131–134° C.; |
| 114 | H | 2,4-Dibromophenyl | |
| 115 | H | 3-Brom-4-fluorophenyl | |
| 116 | H | 3-Brom-4-methoxyphenyl | |
| 117 | H | 2-Iodophenyl | |
| 118 | H | 3-Iodophenyl | |
| 119 | H | 4-Iodophenyl | |
| 120 | H | 2-Chloro-4-fluorophenyl | m.p.: 112–115° C.; |
| 121 | H | 2-Chloro-5-fluorophenyl | |
| 122 | H | 2-Chloro-6-fluorophenyl | m.p.: 80–82° C.; |
| 123 | H | 2-Chloro-4-bromophenyl | |
| 124 | H | 2-Bromo-4-chlorophenyl | |
| 125 | H | 2-Bromo-4-fluorophenyl | |
| 126 | H | 3-Bromo-4-chlorophenyl | |
| 127 | H | 3-Chloro-4-fluorophenyl | |
| 128 | H | 3-Fluoro-4-chlorophenyl | |
| 129 | H | 2-Cyanophenyl | |
| 130 | H | 3-Cyanophenyl | |

TABLE V-continued

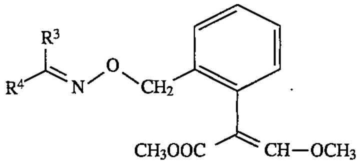

| No. | $R^3$ | $R^4$ | Data |
|---|---|---|---|
| 131 | H | 4-Cyanophenyl | |
| 132 | H | 2-Nitrophenyl | |
| 133 | H | 3-Nitrophenyl | |
| 134 | H | 4-Nitrophenyl | m.p.: 147–155° C.; |
| 135 | H | 2-methylphenyl | m.p.: 57–59° C.; |
| 136 | H | 3-Methylphenyl | m.p.: 54–56° C.; |
| 137 | H | 4-Methylphenyl | m.p.: 86–88° C.; |
| 138 | H | 2,4-Dimethylphenyl | m.p.: 75–77° C.; |
| 139 | H | 2,6-Dimethylphenyl | |
| 140 | H | 3,4-Dimethylphenyl | |
| 141 | H | 3,5-Dimethylphenyl | |
| 142 | H | 2,3,4-Trimethylphenyl | |
| 143 | H | 2,3,5-Trimethylphenyl | |
| 144 | H | 2,3,6-Trimethylphenyl | |
| 145 | H | 2,4,5-Trimethylphenyl | |
| 146 | H | 2,4,6-Trimethylphenyl | |
| 147 | H | 3,4,5-Trimethylphenyl | |
| 148 | H | Pentamethylphenyl | |
| 149 | H | 2-Ethylphenyl | |
| 150 | H | 3-Ethylphenyl | |
| 151 | H | 4-Ethylphenyl | |
| 152 | H | 3,5-Diethylphenyl | |
| 153 | H | 2-n-Propylphenyl | |
| 154 | H | 3-n-Propylphenyl | |
| 155 | H | 4-n-Propylphenyl | |
| 156 | H | 2-iso-propylphenyl | |
| 157 | H | 3-iso-Propylphenyl | |
| 158 | H | 4-iso-Propylphenyl | |
| 159 | H | 2,4-Di-iso-Propylphenyl | |
| 160 | H | 3,5-Di-iso-Propylphenyl | |
| 161 | H | 4-n-Butylphenyl | |
| 162 | H | 4-sec.-Butylphenyl | |
| 163 | H | 4-iso-Butylphenyl | |
| 164 | H | 4-tert.-Butylphenyl | m.p.: 71–73° C. |
| 165 | H | 3-tert.-Butylphenyl | |
| 166 | H | 2-tert.-Butylphenyl | |
| 167 | H | 2,4-Di-tert.-Butylphenyl | |
| 168 | H | 3,5-Di-tert.-Butylphenyl | |
| 169 | H | 4-n-Hexylphenyl | |
| 170 | H | 4-n-Dodecylphenyl | |
| 171 | H | 2-Methyl-4-tert.-Butylphenyl | |
| 172 | H | 2-Methyl-6-tert.-outylphenyl | |
| 173 | H | 2-Methyl-4-iso-Propylphenyl | |
| 174 | H | 2-Methyl-4-cyclohexylphenyl | |
| 175 | H | 2-Methyl-4-phenylphenyl | |
| 176 | H | 2-Methyl-4-benzylphenyl | |
| 177 | H | 2-Methyl-4-phenoxyphenyl | |
| 178 | H | 2-Methyl-4-benzyloxyphenyl | |
| 179 | H | 2-Methyl-3-chlorophenyl | |
| 180 | H | 2-Methyl-4-chlorophenyl | |
| 181 | H | 2-Methyl-5-chlorophenyl | |
| 182 | H | 2-Methyl-6-chlorophenyl | |
| 183 | H | 2-Methyl-4-fluorophenyl | |
| 184 | H | 2-Methyl-3-bromophenyl | |
| 185 | H | 2-Methyl-4-bromophenyl | |
| 186 | H | 2-Methyl-3-methoxyphenyl | |
| 187 | H | 2-Methyl-4-methoxyphenyl | |
| 188 | H | 2-Methyl-5-methoxyphenyl | |
| 189 | H | 2-Methyl-6-methoxyphenyl | |
| 190 | H | 2-Methyl-4-iso-Propoxyphenyl | |
| 191 | H | 2-Methyl-2,5-dimethoxyphenyl | |
| 192 | H | 2-Methoxyphenyl | m.p.: 52–54° C. |
| 193 | H | 3-Methoxyphenyl | $^1$H-NMR ($CDCl_3$): $\delta$ = 3.65s,<br>3.76s, 3.80s, 5.12s,<br>6.88–7.54m, 7.58s, 8.05s |
| 194 | H | 4-Methoxyphenyl | m.p.: 61–63° C. |
| 195 | H | 2,3-Dimethoxyphenyl | |
| 196 | H | 2,4-Dimethoxyphenyl | m.p.: 70–72° C. |

TABLE V-continued

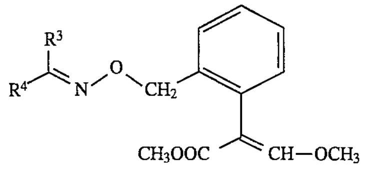

| No. | $R^3$ | $R^4$ | Data |
|---|---|---|---|
| 197 | H | 2,5-Dimethoxyphenyl | |
| 198 | H | 2,6-Dimethoxyphenyl | |
| 199 | H | 3,4-Dimethoxyphenyl | |
| 200 | H | 3,5-Dimethoxyphenyl | m.p.: 79–82° C. |
| 201 | H | 3,6-Dimethoxyphenyl | |
| 202 | H | 2,3,4-Trimethoxyphenyl | |
| 203 | H | 2,3,5-Trimethoxyphenyl | |
| 204 | H | 2,3,6-Trimethoxyphenyl | |
| 205 | H | 2,4,5-Trimethoxyphenyl | |
| 206 | H | 2,4,6-Trimethoxyphenyl | |
| 207 | H | 3,4,5-Trimethoxyphenyl | |
| 208 | H | 2-Ethoxyphenyl | |
| 209 | H | 3-Ethoxyphenyl | $^1$H-NMR ($CDCl_3$): δ = 1.39t, 3.67s, 3.80s, 4.02q, 5.12s, 6.87–7.54m, 7.58s, 8.05s |
| 210 | H | 4-Ethoxyphenyl | m.p.: 93–94° C. |
| 211 | H | 2-iso-Propoxyphenyl | |
| 212 | H | 3-iso-Propoxyphenyl | |
| 213 | H | 4-iso-Propoxyphenyl | |
| 214 | H | 3-tert.-Butoxyphenyl | |
| 215 | H | 4-tert.-Butoxyphenyl | $^1$H-NMR ($CDCl_3$): δ = 1.36s, 3.68s, 3.78s, 5.09s, 6.94–7.53m, 7.58s, 8.07s |
| 216 | H | 2-Trifluoromethoxyphenyl | |
| 217 | H | 3-Trifluoromethoxyphenyl | |
| 218 | H | 4-Trtfluorowthoxyphenyl | |
| 219 | H | 3-(1',1',2',2'-Tetrafluoro)ethoxyphenyl | |
| 220 | H | 4-(1',1',2',2'-Tetrafluoro)ethoxyphenyl | |
| 221 | H | 2-Chloromethylphenyl | |
| 222 | H | 3-Chloromethylphenyl | |
| 223 | H | 4-Chloromethylphenyl | |
| 224 | H | 2-Trifluoromethylphenyl | m.p.: 75–77° C. |
| 225 | H | 3-Trifluoromethylphenyl | |
| 226 | H | 4-Trifluoromethylphenyl | m.p.: 111–114° C. |
| 227 | H | 2-(Methoxyiminomethyl)phenyl | |
| 228 | H | 3-(Methoxyiminomethyl)phenyl | |
| 229 | H | 4-(Methoxyiminomethyl)phenyl | |
| 230 | H | 2-(Ethoxyiminomethyl)phenyl | |
| 231 | H | 3-(Ethoxyininomethyl)phenyl | |
| 232 | H | 4-(Ethoxyiminomthyl)phenyl | |
| 233 | H | 2-(n-Propoxyiminomethyl)phenyl | |
| 234 | H | 3-(n-Propoxyiminomethyl)phenyl | |
| 235 | H | 4-(n-Propoxyiminomethyl)phenyl | |
| 236 | H | 2-(iso-Propoxyiminomethyl)phenyl | |
| 237 | H | 3-(iso-Propoxyiminomethyl)phenyl | |
| 238 | H | 4-(iso-Propoxyiminomethyl)phenyl | |
| 239 | H | 2-(n-Butoxyiminomethyl)phenyl | |
| 240 | H | 3-(n-Butoxyiminomethyl)phenyl | |
| 241 | H | 4-(n-Butoxyiminomethyl)phenyl | |
| 242 | H | 2-(iso-Butoxyiminomethyl)phenyl | |
| 243 | H | 3-(iso-Butoxytminomethyl)phenyl | |
| 244 | H | 4-(iso-Butoxyiminomethyl)phenyl | |
| 245 | H | Z-(tert.-Butoxyiminamethyl)phenyl | |
| 246 | H | 3-(tert.-Butoxyiminomethyl)phenyl | |
| 247 | H | 4-(tert.-Butoxyiminomethyl)phenyl | |
| 248 | H | 2-(n-Pentoxyiminomethyl)phenyl | |
| 249 | H | 3-(n-Pentoxyiminomethyl)phenyl | |
| 250 | H | 4-(n-Pentoxyiminomethyl)phenyl | |
| 251 | H | 2-(n-Hexoxyiminomethyl)phenyl | |
| 252 | H | 3-(n-Hexoxyiminomethyl)phenyl | |
| 253 | H | 4-(n-Hexoxyiminomethyl)phenyl | |
| 254 | H | 2-(Allyloxyiminomethyl)phenyl | |
| 255 | H | 3-(Allyloxyiminomethyl)phenyl | |
| 256 | H | 4-(Allyloxyiminomethyl)phenyl | |
| 257 | H | 2-(Benzyloxyiminomethyl)phenyl | |
| 258 | H | 3-(Benzyloxyiminomethyl)phenyl | |
| 259 | H | 4-(Benzyloxyiminamethyl)phenyl | |
| 260 | H | 2-(Methoxyimino-1'-ethyl)phenyl | |

TABLE V-continued

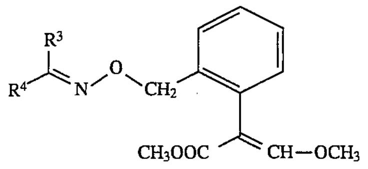

| No. | $R^3$ | $R^4$ | Data |
|---|---|---|---|
| 261 | H | 3-(Methoxyimino-1'-ethyl)phenyl | |
| 262 | H | 4-(Methoxytmino-1'-ethyl)phenyl | |
| 263 | H | 2-(Ethoxyimino-1'-ethyl)phenyl | |
| 264 | H | 3-(Ethoxyimino-1'-ethyl)phenyl | |
| 265 | H | 4-(Ethoxyimino-1'-ethyl)phenyl | |
| 266 | H | 2-(n-Propoxyimino-1'-ethyl)phenyl | |
| 267 | H | 3-(n-Propoxyimino-1'-ethyl)phenyl | |
| 268 | H | 4-(n-Propoxyimino-1'-ethyl)phenyl | |
| 269 | H | 2-(n-Butoxyamino-1'-ethyl)phenyl | |
| 270 | H | 3-(n-Butoxyanino-1'-ethyl)phenyl | |
| 271 | H | 4-(n-Butoxyamino-1'-ethyl)phenyl | |
| 272 | H | 2-(n-Pentoxyimino-1'-ethyl)phenyl | |
| 273 | H | 3-(n-Pentoxyimino-1'-ethyl)phenyl | |
| 274 | H | 4-(n-Pentoxyimino-1'-ethyl)phenyl | |
| 275 | H | 2-(n-Hexoxyimino-1'-ethyl)phenyl | |
| 276 | H | 3-(n-Hexoxyimino-1'-ethyl)phenyl | |
| 277 | H | 4-(n-Hexoxyimino-1'-ethyl)phenyl | |
| 278 | H | 2-(Allyloxyimino-1'-ethyl)phenyl | |
| 279 | H | 3-(Allyloxyimino-1'-ethyl)phenyl | |
| 280 | H | 4-(Allyloxyimino-1'-ethyl)phenyl | |
| 281 | H | 2-(Benzyloxyimino-1'-ethyl)phenyl | |
| 282 | H | 3-(Benzyloxyimino-1'-ethyl)phenyl | |
| 283 | H | 4-(Benzyloxyimino-1'-ethyl)phenyl | |
| 284 | H | 2-Phenylphenyl | |
| 285 | H | 3-Phenylphenyl | |
| 286 | H | 4-Phenylphenyl | m.p.: 94–96° C. |
| 287 | H | 2-Phenoxyphenyl | |
| 288 | H | 3-Phenoxyphenyl | |
| 289 | H | 4-Phenoxyphenyl | |
| 290 | H | 2-Benzyloxyphenyl | |
| 291 | H | 3-Benzyloxyphenyl | |
| 292 | H | 4-Benzyloxyphenyl | m.p.: 94–96° C. |
| 293 | H | 4-(Imidazol-1'-yl)phenyl | |
| 294 | H | 4-(Piperazin-1'-yl)phenyl | |
| 295 | H | 4-(Morpholin-1'-yl)phenyl | |
| 296 | H | 4-(Piperidin-1'-yl)phenyl | |
| 297 | H | 4-(Pyridyl-2'-oxy)phenyl | |
| 298 | H | 2-Cyclopropylphenyl | |
| 299 | H | 3-Cyclopropylphenyl | |
| 300 | H | 4-Cyclopropylphenyl | |
| 301 | H | 3-Cyclohexylphenyl | |
| 302 | H | 4-Cyclohexylphenyl | |
| 303 | H | 4-Oxiranylphenyl | |
| 304 | H | 4-(1',3'-Dioxan-2'-yl)phenyl | |
| 305 | H | 4-(Tetrahydropyran-2-yloxy)phenyl | |
| 306 | H | 1-Naphthyl | |
| 307 | H | 2-Naphthyl | oil; IR (film): 1707, 1633,1257,1129,110 |
| 308 | H | 9-Anthryl | |
| 309 | H | 1-Naphtoxy | |
| 310 | H | 2-Naphtoxy | |
| 311 | H | 9-Anthroxy | |
| 312 | H | Phenoxy | |
| 313 | H | 2-Chlorophenoxy | |
| 314 | H | 3-Chlorophenoxy | |
| 315 | H | 4-Chlorophenoxy | |
| 316 | H | 4-Methylphenoxy | |
| 317 | H | 4-tert.-Butylphenoxy | |
| 318 | H | 4-Methoxyphenoxy | |
| 319 | H | 4-Ethoxyphenoxy | |
| 320 | H | 4-tert.-Butoxyphenoxy | |
| 321 | H | Phenylthio | |
| 322 | H | 2-Chlorophenylthio | |
| 323 | H | 4-Chlorophenylthio | |
| 324 | H | Benzyl | |
| 325 | H | 2-Methylbenzyl | |
| 326 | H | 3-Methylbenzyl | |
| 327 | H | 4-Methylbenyzl | |

TABLE V-continued

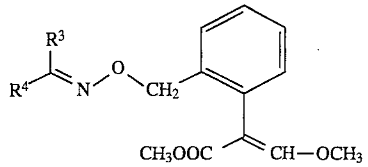

| No. | $R^3$ | $R^4$ | Data |
|---|---|---|---|
| 328 | H | 4-tert.-Butylbenzyl | |
| 329 | H | 2-Chlorobenzyl | |
| 330 | H | 3-Chlorobenzyl | |
| 331 | H | 4-Chlorobenzyl | |
| 332 | H | 2,4-Dichlorobenzyl | |
| 333 | H | 2,6-Dichlorobenzyl | |
| 334 | H | 2,4,6-Trichlorobenzyl | |
| 335 | H | 2-Trifluoromethylbenzyl | |
| 336 | H | 3-Trtfluaromethylbenzyl | |
| 337 | H | 4-Trifluoromethylbenzyl | |
| 338 | H | 2-Methoxybenzyl | |
| 339 | H | 4-Methoxybenzyl | |
| 340 | H | 4-tert.-Butoxybenzyl | |
| 341 | H | 4-Phenoxybenzyl | |
| 342 | H | 1-Phenethyl | |
| 343 | H | 2-Phenethyl | |
| 344 | H | 1-Phenylpropyl | |
| 345 | H | 2-Phenylpropyl | |
| 346 | H | 3-Phenylpropyl | |
| 347 | H | 2-Methyl-2-phenylpropyl | |
| 348 | H | 2-Methyl-3-phenylpropyl | |
| 349 | H | 4-Phenylbutyl | |
| 350 | H | 2-Phenyl-1-ethenyl | |
| 351 | H | 1-Phenyl-1-ethenyl | |
| 352 | H | 1-Phenyl-1-propenyl | |
| 353 | H | 1-Phenyl-1-propen-2-yl | |
| 354 | H | 2,2-Diphenylethenyl | |
| 355 | H | Phenoxymethyl | |
| 356 | H | 2-Pyridyl | |
| 357 | H | 3-Pyridyl | |
| 358 | H | 4-Pyridyl | |
| 359 | H | 2,6-Pyrimidinyl | |
| 360 | H | 1,5-Pyrimidinyl | |
| 361 | H | 2-Thienyl | |
| 362 | H | 3-Thienyl | |
| 363 | H | 2-Furyl | |
| 364 | H | 3-Furyl | |
| 365 | H | 1-Pyrrolyl | |
| 366 | H | 1-Imidazolyl | |
| 367 | H | 1,2,4-Triazolyl | |
| 368 | H | 1,3,4-Triazolyl | |
| 369 | H | 4-Thiazolyl | |
| 370 | H | 2-Senzothiozolyl | |
| 371 | H | 2-Pyridyloxy | |
| 372 | H | 2-Pyrimidinyloxy | |
| 373 | H | 2-Pyridylthio | |
| 374 | H | 2-Pyrimidinylthio | |
| 375 | H | 2-Benzothiozolylthio | |
| 376 | H | Phenylthiomethyl | |
| 377 | H | 2-Pyridylmethyl | |
| 378 | H | 3-Pyridylmethyl | |
| 379 | H | Furfuryloxy | |
| 380 | H | Thienylmthoxy | |
| 381 | H | 3-Isoxazolylmethoxy | |
| 382 | 4 | 2-Oxazolylmethoxy | |
| 383 | 4 | 2-Pyridylmethoxy | |
| 384 | H | 2'-Furyl-2-ethenyl | |
| 385 | H | 2'-Thienyl-2-ethenyl | |
| 386 | H | 3'-Pyridyl-2-ethenyl | |
| 387 | H | Oxiranyl | |
| 388 | H | 1-Aziridinyl | |
| 389 | H | 1-Azetidinyl | |
| 390 | H | 1-Pyrrolidinyl | |
| 391 | H | 2-Tetrahydrofuryl | |
| 392 | H | 2-Tetrahydropyranyl | |
| 393 | H | 3-Tetrahydropyranyl | |
| 394 | H | 1-Piperidinyl | |
| 395 | H | 1-Morpholinyl | |

TABLE V-continued

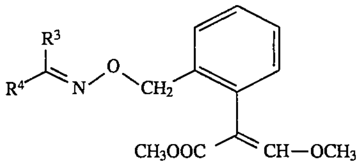

| No. | $R^3$ | $R^4$ | Data |
|---|---|---|---|
| 396 | H | i-Piperazinyl | |
| 397 | H | 1,3-Dioxan-2-yl | |
| 398 | H | 3-Tetrahydrothiopyranyl | |
| 399 | H | 2-Dihydropyranyloxy | |
| 400 | H | 2-Tetrahydropyranyloxy | |
| 401 | H | $CF_3$ | |
| 402 | H | 2-Fluoroethyl | |
| 403 | H | 2,2,2-Trifluoroethyl | |
| 404 | m | Pentafluoroethyl | |
| 405 | H | Chloromethyl | |
| 406 | H | Dichloromethyl | |
| 407 | H | Trichloromethyl | |
| 408 | H | 2-Chloroethyl | |
| 409 | H | 2,2,2-Trichloroethyl | |
| 410 | H | Pentachloroothyl | |
| 411 | H | Cyclopropyl | |
| 412 | H | Cyclobutyl | |
| 413 | H | cyclopentyl | |
| 414 | H | Cyclohexyl | |
| 415 | H | 1-Methylcyclopropyl | |
| 416 | H | 2,2-Dimethylcyclopropyl | |
| 417 | H | 1-Methylcyclohexyl | |
| 418 | H | 2,2-Difluorocyclopropyl | |
| 419 | H | 2,2-Dichloracyclopropyl | |
| 420 | H | 2,2-Dibromocyclopropyl | |
| 421 | H | 2,2-Dichloro-3-Methylcyclopropyl | |
| 422 | H | 2,2,3,3-Tetrafluorocyclobutyl | |
| 423 | H | Ethenyl | |
| 424 | H | 1-Propenyl | |
| 425 | H | 2-Methyl-1-propenyl | |
| 426 | H | 4-Methylpent-3-en-1-yl | |
| 427 | H | 2-Propenyl | |
| 428 | H | 2-Butenyl | |
| 429 | H | 1-Methyl-2-propenyl | |
| 430 | H | 3-Methyl-2-butenyl | |
| 431 | H | 2,2-Difluoroethenyl | |
| 432 | H | 2,2-Dichloroethenyl | |
| 433 | H | 3,3,3-Trifluoropropenyl | |
| 434 | H | 3,3,3-Trichloropropenyl | |
| 435 | H | 3-Chloro-2-propenyl | |
| 436 | H | Cyclopent-1-enyl | |
| 437 | H | Cyclopentadienyl | |
| 438 | H | Cyclohex-1-enyl | |
| 439 | H | Pentafluorocyclopentadienyl | |
| 440 | H | Pentachlorocyclopentadienyl | |
| 441 | H | 4-Dimethylaminaphenyl | m.p.: 90–92° C. |
| 442 | H | 4-n-Butoxyphenyl | m.p.: 79–82° C. |

TABLE VI

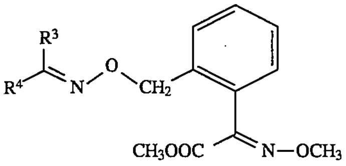

| No. | $R^3$ | $R^4$ | Data |
|---|---|---|---|
| 1 | H | H | m.p.: 94–95° C. |
| 2 | H | Methoxymethyl | |
| 3 | H | Ethoxymethyl | |
| 4 | H | n-Propoxymethyl | |
| 5 | H | iso-Propoxymethyl | |
| 6 | H | tert.-Butoxymethyl | |

TABLE VI-continued

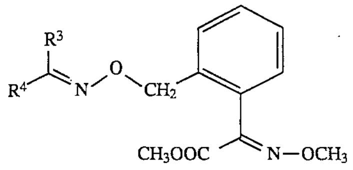

| No. | $R^3$ | $R^4$ | Data |
|---|---|---|---|
| 7 | H | 2-Methoxyprop-2-yl | |
| 8 | H | 2-Ethoxyprop-2-yl | |
| 9 | H | 2-n-Propoxyprop-2-yl | |
| 10 | H | 2-iso-Propoxyprop-2-yl | |
| 11 | H | 2-tert.-Butoxyprop-2-yl | |
| 12 | H | Methylthiomethyl | |
| 13 | H | tert.-Butylthiomethyl | |
| 14 | H | 2-methylthioprop-2-yl | |
| 15 | H | 2-iso-Propylthioprop-2-yl | |
| 16 | H | 2-tert.-Butylthioprop-2-yl | |
| 17 | H | Methyl | |
| 18 | H | Ethyl | |
| 19 | H | n-Propyl | |
| 20 | H | iso-Propyl | |
| 21 | H | n-Butyl | |
| 22 | H | iso-Butyl | |
| 23 | H | sec.-Butyl | |
| 24 | H | tert.-Butyl | |
| 25 | H | n-Hexyl | |
| 26 | H | n-Decyl | |
| 27 | H | Cyclopropyl | |
| 28 | H | Cyclohexyl | |
| 29 | H | Phenylthiomethyl | |
| 30 | H | 2-Phenylthiomethyl | |
| 31 | H | 2-(2'-Chlorophenylthio)prop-2-yl | |
| 32 | H | Ethynyl | |
| 33 | H | 1-Propynyl | |
| 34 | H | Methoxy | |
| 35 | H | Ethoxy | |
| 36 | H | n-Propoxy | |
| 37 | H | iso-Propoxy | |
| 38 | H | n-Butoxy | |
| 39 | H | iso-Butoxy | |
| 40 | H | sec.-Butoxy | |
| 41 | H | tert.-Butoxy | |
| 42 | H | Methylthio | |
| 43 | H | Ethylthio | |
| 44 | H | n-Propylthio | |
| 45 | H | iso-Propylthio | |
| 46 | H | n-Butylthio | |
| 47 | H | iso-Butylthio | |
| 48 | H | sec.-Butylthio | |
| 49 | H | tert.-Butylthio | |
| 50 | H | Benzylthio | |
| 51 | H | Trifluoromethoxy | |
| 52 | H | Cyano | |
| 53 | H | Amino | |
| 54 | H | Methylamino | |
| 55 | H | Dimethylamino | |
| 56 | H | Ethylamino | |
| 57 | H | Diethylamino | |
| 58 | H | Di-n-Propylanino | |
| 59 | H | Di-iso-Propylamino | |
| 60 | H | Di-n-Butylamino | |
| 61 | H | Di-iso-Butylamino | |
| 62 | H | Acetyl | |
| 63 | H | Propion-1-yl | |
| 64 | H | Butyr-1-yl | |
| 65 | H | iso-Butyr-1-yl | |
| 66 | H | Pivaloyl | |
| 67 | H | Benzoyl | |
| 68 | H | 4-Chlorobenzoyl | |
| 69 | H | Benzylcarbonyl | |
| 70 | H | Methoxycarbonyl | |
| 71 | H | Ethoxycarbonyl | |
| 72 | H | n-Propoxycarbonyl | |
| 73 | H | iso-Propoxycarbonyl | |
| 74 | H | n-Butoxycarbonyl | |
| 75 | H | iso-Butoxycarbonyl | |

TABLE VI-continued

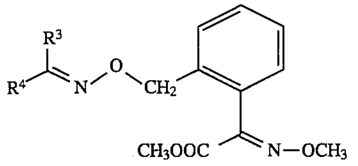

| No. | $R^3$ | $R^4$ | Data |
|---|---|---|---|
| 76 | H | sec.-Butoxycarbonyl | |
| 77 | H | tert.-Butoxycarbonyl | |
| 78 | H | n-Hexoxycarbonyl | |
| 79 | H | Phenoxycarbonyl | |
| 80 | H | 4-Chlorophenoxycarbonyl | |
| 81 | H | Benzyloxycarbonyl | |
| 82 | H | Aminocarbonyl | |
| 83 | H | Dimethylaminocarbonyl | |
| 84 | H | Diethylaminocarbonyl | |
| 85 | H | Di-iso-Propylaminocarbonyl | |
| 86 | H | Phenylaminocarbonyl | |
| 87 | H | N-Methyl-N-Phenylaminocarbonyl | |
| 88 | H | Phenyl | m.p.: 92–95° C. |
| 89 | H | 2-Fluorophenyl | m.p.: 92–95° C. |
| 90 | H | 3-Fluorophenyl | m.p.: 58–60° C. |
| 91 | H | 4-Fluorophenyl | m.p.: 110–111° C. |
| 92 | H | Pentafluorophenyl | m.p.: 118–120° C. |
| 93 | H | 2-Chlorophenyl | $^1$H-NMR($CDCl_3$): $\delta$ = 3.70s, 3.82s, 5.15s, 7.15–7.40m, 7.52m, 7.60s, 7.85m, 8.52s |
| 94 | H | 3-Chlorophenyl | m.p.: 58–60° C. |
| 95 | H | 4-Chlorophenyl | m.p.: 146–148° C. |
| 96 | H | Pentachlorophenyl | |
| 97 | H | 2,3-Dichlorophenyl | m.p.: 95–97° C. |
| 98 | H | 2,4-Dichlorophenyl | m.p.: 58–62° C. |
| 99 | H | 2,5-Dichlorophenyl | |
| 100 | H | 2,6-Dichlorophenyl | m.p.: 136–140° C. |
| 101 | H | 3,4-Dichlorophenyl | m.p.: 94–97° C. |
| 102 | N | 3,5-Dichlorophenyl | m.p.: 88–91° C. |
| 103 | H | 2,3,4-Trichlorophenyl | |
| 104 | N | 2,3,5-Trichlorophenyl | |
| 105 | H | 2,3,6-Trichlorophenyl | |
| 106 | H | 2,4,5-Trichlorophenyl | |
| 107 | H | 2,4,6-Trichlorophenyl | |
| 108 | H | 3,4,5-Trichlorophenyl | |
| 109 | H | 2,3,4,6-Tetrachlorophenyl | |
| 110 | H | 2,3,5,6-Tetrachlorophenyl | |
| 111 | H | 2-Bromophenyl | m.p.: 91–94° C. |
| 112 | H | 3-Bromophenyl | m.p.: 63–64° C. |
| 113 | H | 4-Bromophenyl | m.p.: 145–147° C. |
| 114 | H | 2,4-Dibromophenyl | |
| 115 | H | 3-Bromo-4-Fluorophenyl | |
| 116 | H | 3-Bromo-4-Methoxyphenyl | |
| 117 | H | 2-Iodophenyl | |
| 118 | H | 3-Iodophenyl | |
| 119 | H | 4-Iodophenyl | |
| 120 | H | 2-Chloro-4-Fluorophenyl | m.p.: 90–93° C. |
| 121 | H | 2-Chloro-5-Fluorophenyl | |
| 122 | H | 2-Chloro-6-Fluorophenyl | m.p.: 111–113° C. |
| 123 | H | 2-Chloro-4-Bromophenyl | |
| 124 | H | 2-Bromo-4-Chlorophenyl | |
| 125 | H | 2-Bromo-4-Fluorophenyl | |
| 126 | H | 3-Bromo-4-Chlorophenyl | |
| 127 | H | 3-Chloro-4-Fluorophenyl | |
| 128 | H | 3-Fluoro-4-Chlorophenyl | |
| 129 | H | 2-Cyanophenyl | |
| 130 | H | 3-Cyanophenyl | |
| 131 | H | 4-Cyanophenyl | |
| 132 | H | 2-Nitrophenyl | |
| 133 | H | 3-Nitrophenyl | |
| 134 | H | 4-Nitrophenyl | m.p.: 142–146° C. |
| 135 | H | 2-Methylphenyl | m.p.: 58–60° C. |
| 136 | H | 3-Methylphonyl | m.p.: 70–72° C. |
| 137 | H | 4-Methylphenyl | m.p.: 99–102° C. |
| 138 | H | 2,4-Dimethylphenyl | m.p.: 54–56° C. |
| 139 | H | 2,6-Dimethylphenyl | |
| 140 | H | 3,4-Dimethylphenyl | |
| 141 | H | 3,5-Dimethylphenyl | |
| 142 | H | 2,3,4-Trimethylphenyl | |

TABLE VI-continued

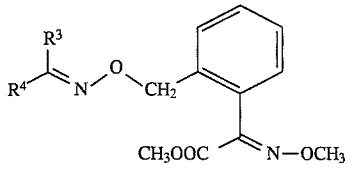

| No. | $R^3$ | $R^4$ | Data |
|---|---|---|---|
| 143 | H | 2,3,5-Trimethylphenyl | |
| 144 | H | 2,3,6-Trimethylphenyl | |
| 145 | H | 2,4,5-Trimethylphenyl | |
| 146 | H | 2,4,6-Trimethylphenyl | |
| 147 | H | 3,4,5-Trimethylphenyl | |
| 148 | H | Pentamethylphenyl | |
| 149 | H | 2-Ethylphenyl | |
| 150 | H | 3-Ethylphenyl | |
| 151 | H | 4-Ethylphenyl | |
| 152 | H | 3,5-Diethylphonyl | |
| 153 | H | 2-n-Propylphenyl | |
| 154 | H | 3-n-Propylphenyl | |
| 155 | H | 4-n-Propylphenyl | |
| 156 | H | 2-iso-Propylphenyl | |
| 157 | H | 3-iso-Propylphenyl | |
| 158 | H | 4-iso-Propylphenyl | |
| 159 | H | 2,4-Di-iso-Propylphenyl | |
| 160 | H | 3,5-Di-iso-Propylphenyl | |
| 161 | H | 4-n-Butylphenyl | |
| 162 | H | 4-sec.-Butylphenyl | |
| 163 | H | 4-iso-Butylphenyl | |
| 164 | H | 4-tert.-Butylphenyl | m.p.: 82–84° C. |
| 165 | H | 3-tert.-Butylphenyl | |
| 166 | H | 2-tert.-Butylphenyl | |
| 167 | H | 2,4-Di-tert.-Butylphenyl | |
| 168 | H | 3,5-Di-tert.-Butylphenyl | |
| 169 | H | 4-n-Hexylphenyl | |
| 170 | H | 4-n-Dodecylphenyl | |
| 171 | H | 2-Methyl-4-tert.-Butylphenyl | |
| 172 | H | 2-Methyl-6-tert.-Butylphenyl | |
| 173 | H | 2-Methyl-4-iso-Propylphenyl | |
| 174 | H | 2-Methyl-4-Cyclohexylphenyl | |
| 175 | H | 2-Methyl-4-Phenylphenyl | |
| 176 | H | 2-Methyl-4-Benzylphenyl | |
| 177 | H | 2-Methyl-4-Phenoxyphenyl | |
| 178 | H | 2-Methyl-4-Benzyloxyphenyl | |
| 179 | H | 2-Methyl-3-Chlorophenyl | |
| 180 | H | 2-Methyl-4-Chlorophenyl | |
| 181 | H | 2-Methyl-5-Chlorophenyl | |
| 182 | H | 2-Methyl-6-Chlorophenyl | |
| 183 | H | 2-Methyl-4-Fluorophenyl | |
| 184 | H | 2-Methyl-3-Bromophenyl | |
| 185 | H | 2-Methyl-4-Bromophenyl | |
| 186 | H | 2-Methyl-3-Methoxyphenyl | |
| 187 | H | 2-Methyl-4-Methoxyphenyl | |
| 188 | H | 2-Methyl-5-Methoxyphenyl | |
| 189 | H | 2-Methyl-6-Methoxyphenyl | |
| 190 | H | 2-Methyl-4-iso-Propoxyphenyl | |
| 191 | H | 2-Methyl-2,5-Dimethoxyphenyl | |
| 192 | H | 2-Methoxyphenyl | m.p.: 65–68° C. |
| 193 | H | 3-Methoxyphenyl | m.p.: 83–84° C. |
| 194 | H | 4-Methoxyphenyl | m.p.: 88–90° C. |
| 195 | H | 2,3-Dimethoxyphenyl | |
| 196 | H | 2,4-Dimethoxyphenyl | m.p.: 90–93° C. |
| 197 | H | 2,5-Dimethoxyphenyl | |
| 198 | H | 2,6-Dimethoxyphenyl | |
| 199 | H | 3,4-Dimethoxyphenyl | m.p.: 70–72° C. |
| 200 | H | 3,5-Dimethoxyphenyl | m.p.: 97–99° C. |
| 201 | H | 3,6-Dimethoxyphenyl | |
| 202 | H | 2,3,4-Trimethoxyphenyl | |
| 203 | H | 2,3,5-Trimethoxyphemyl | |
| 204 | H | 2,3,6-Trimethoxyphenyl | |
| 205 | H | 2,4,5-Trimethoxyphenyl | |
| 206 | H | 2,4,6-Trimethoxyphenyl | |
| 207 | H | 3,4,5-Trimethoxyphenyl | m.p.: 105–109° C. |
| 208 | H | 2-Ethoxyphenyl | |
| 209 | H | 3-Ethoxyphenyl | m.p.: 90–92° C. |
| 210 | H | 4-Ethoxyphenyl | m.p.: 97–98° C. |
| 211 | H | 2-iso-Propoxyphenyl | |

TABLE VI-continued

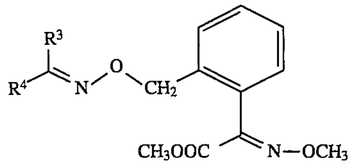

| No. | $R^3$ | $R^4$ | Data |
|---|---|---|---|
| 212 | H | 3-iso-Propoxyphenyl | |
| 213 | H | 4-iso-Propoxyphenyl | |
| 214 | H | 3-tert.-Butoxyphenyl | |
| 215 | H | 4-tert.-Butoxyphenyl | m.p.: 78–83° C. |
| 216 | H | 2-Trifluoromethoxyphenyl | |
| 217 | H | 3-Trifluoromethoxyphenyl | |
| 218 | H | 4-Trifluoromethoxyphenyl | |
| 219 | H | 3-(1',1',2',2'-Tetrafluoro)ethoxyphenyl | |
| 220 | H | 4-(1',1',2',2'-Tetrafluoro)ethoxyphenyl | |
| 221 | H | 2-Chloromethylphenyl | |
| 222 | H | 3-Chloromethylphenyl | |
| 223 | H | 4-Chloromethylphenyl | |
| 224 | H | 2-Trifluoromethylphenyl | m.p.: 58–60° C. |
| 225 | H | 3-Trifluoromethylphenyl | m.p.: 74–77° C. |
| 226 | H | 4-Trifluoromethylphenyl | m.p.: 120–122° C. |
| 227 | H | 2-(Methoxyiminomethyl)phenyl | |
| 228 | H | 3-(Methoxyiminomethyl)phenyl | |
| 229 | H | 4-(Methoxyiminomethyl)phenyl | |
| 230 | H | 2-(Ethoxyiminomethyl)phenyl | |
| 231 | H | 3-(Ethoxyiminomethyl)phenyl | |
| 232 | H | 4-(Ethoxyiminomethyl)phenyl | |
| 233 | H | 2-(n-Propoxyiminomethyl)phenyl | |
| 234 | H | 3-(n-Propoxyiminomethyl)phenyl | |
| 235 | H | 4-(n-Propoxyiminomethyl)phenyl | |
| 236 | H | 2-(iso-Propoxyiminomethyl)phenyl | |
| 237 | H | 3-(iso-Propoxyiminomethyl)phenyl | |
| 238 | H | 4-(iso-Propoxyiminomethyl)phenyl | |
| 239 | H | 2-(n-Butoxyiminomethyl)phenyl | |
| 240 | H | 3-(n-Butoxyiminomethyl)phenyl | |
| 241 | H | 4-(n-Butoxyiminomethyl)phenyl | |
| 242 | H | 2-(iso-Butoxyiminomethyl)phenyl | |
| 243 | H | 3-(iso-Butoxyiminomethyl)phenyl | |
| 244 | H | 4-(iso-Butoxyiminomethyl)phenyl | |
| 245 | H | 2-(tert.-Butoxyiminomethyl)phenyl | |
| 246 | H | 3-(tert.-Butoxyiminomethyl)phenyl | |
| 247 | H | 4-(tert.-Butoxyiminomethyl)phonyl | |
| 248 | H | 2-(n-Pentoxyiminomethyl)phenyl | |
| 249 | H | 3-(n-Pentoxyininomethyl)phenyl | |
| 250 | H | 4-(n-PentoxyiminoMethyl)phenyl | |
| 251 | H | 2-(n-Hexoxyiminomethyl)phenyl | |
| 252 | H | 3-(n-Hexoxyiminomethyl)phenyl | |
| 253 | H | 4-(n-Hexoxyiminomethyl)phenyl | |
| 254 | H | 2-(Allyloxyiminomethyl)phenyl | |
| 255 | H | 3-(Allyloxyiminomethyl)phenyl | |
| 256 | H | 4-(Allyloxyiminomethyl)phenyl | |
| 257 | H | 2-(Benzyloxytainomethyl)phenyl | |
| 258 | H | 3-(Benzyloxyininomethyl)phenyl | |
| 259 | H | 4-(Benzyloxyiminomethyl)phenyl | |
| 260 | H | 2-(Methoxyimino-1'-ethyl)phenyl | |
| 261 | H | 3-(Methoxyimino-1'-ethyl)phenyl | |
| 262 | H | 4-(Methoxyimino-1'-ethyl)phenyl | |
| 263 | H | 2-(Ethoxyimino-1'-ethyl)phenyl | |
| 264 | H | 3-(Ethoxyimino-1'-ethyl)phenyl | |
| 265 | H | 4-(Ethoxyimino-1'-ethyl)phenyl | |
| 266 | H | 2-(n-Propoxyimino-1'-ethyl)phenyl | |
| 267 | H | 3-(n-Propoxyimino-1'-ethyl)phenyl | |
| 268 | H | 4-(n-Propoxyimino-1'-ethyl)phenyl | |
| 269 | H | 2-(n-Butoxyamino-1'-ethyl)phenyl | |
| 270 | H | 3-(n-Butoxyanino-1'-ethyl)phenyl | |
| 271 | H | 4-(n-Butoxyamino-1'-ethyl)phenyl | |
| 272 | H | 2-(n-Pentoxyimino-1'-ethyl)phenyl | |
| 273 | H | 3-(n-Pentoxyimino-1'-ethyl)phenyl | |
| 274 | H | 4-(n-Pentoxyimino-1'-ethyl)phenyl | |
| 275 | H | 2-(n-Hexoxyimino-1'-ethyl)phenyl | |
| 276 | H | 3-(n-Hexoxyimino-1'-ethyl)phenyl | |
| 277 | H | 4-(n-Hexoxyimino-1'-ethyl)phenyl | |
| 278 | H | 2-(Allyloxyimino-1'-ethyl)phenyl | |
| 279 | H | 3-(Allyloxyimino-1'-ethyl)phenyl | |
| 280 | H | 4-(Allyloxyimino-1'-ethyl)phenyl | |

TABLE VI-continued

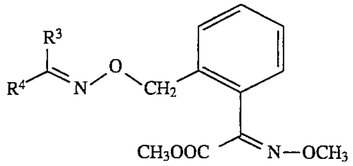

| No. | $R^3$ | $R^4$ | Data |
|---|---|---|---|
| 281 | H | 2-(Benzyloxyimino-1'-ethyl)phenyl | |
| 282 | H | 3-(Benzyloxyimino-1'-ethyl)phenyl | |
| 283 | H | 4-(Benzyloxyimino-1'-ethyl)phenyl | |
| 284 | H | 2-Phenylphenyl | |
| 285 | H | 3-Phenylphenyl | |
| 286 | H | 4-Phenylphenyl | m.p.: 100–102° C. |
| 287 | H | 2-Phenoxyphenyl | |
| 288 | H | 3-Phenoxyphenyl | IR (film): 1728,1489, 1247,1214,1070,1020 |
| 289 | H | 4-Phenoxyphenyl | m.p.: 85–87° C. |
| 290 | H | 2-Benzyloxyphenyl | m.p.: 83–85° C. |
| 291 | H | 3-Benzyloxyphenyl | m.p.: 66–68° C. |
| 292 | H | 4-Benzyloxyphenyl | m.p.: 104–106° C. |
| 293 | H | 4-(Imidazol-1'-yl)phenyl | |
| 294 | H | 4-(Piperazin-1'-yl)phenyl | |
| 295 | H | 4-(Morpholin-1'-yl)phenyl | |
| 296 | H | 4-(Piperidin-1'-yl)phenyl | |
| 297 | H | 4-(Pyridyl-2'-oxy)phenyl | |
| 298 | H | 2-Cyclopropylphenyl | |
| 299 | H | 3-Cyclopropylphenyl | |
| 300 | H | 4-Cyclopropylphenyl | |
| 301 | H | 3-Cyclohexylphenyl | |
| 302 | H | 4-Cyclohexylphenyl | |
| 303 | H | 4-Oxiranylphenyl | |
| 304 | H | 4-(1',3'-Dioxan-2'-yl)phenyl | |
| 305 | H | 4-(Tetrahydropyran-2-yloxy)phenyl | |
| 306 | H | 1-Naphthyl | m.p.: 70–73° C. |
| 307 | H | 2-Naphthyl | m.p.: 125–126° C. |
| 308 | H | 9-Anthryl | |
| 309 | H | 1-Naphthoxy | |
| 310 | H | 2-Naphthoxy | |
| 311 | H | 9-Anthroxy | |
| 312 | H | Phenoxy | |
| 313 | H | 2-Chlorophenoxy | |
| 314 | H | 3-Chlorophenoxy | |
| 315 | H | 4-Chlorophenoxy | |
| 316 | H | 4-Methylphenoxy | |
| 317 | H | 4-tert.-Butylphenoxy | |
| 318 | H | 4-Methoxyphenoxy | |
| 319 | H | 4-Ethoxyphenoxy | |
| 320 | H | 4-tert.-Butoxyphenoxy | |
| 321 | H | Phenylthio | |
| 322 | H | 2-Chlorophenylthio | |
| 323 | H | 4-Chlorophenylthio | |
| 324 | H | Benzyl | |
| 325 | H | 2-Methylbenzyl | |
| 326 | H | 3-Methylbenzyl | |
| 327 | H | 4-Methylbenyzl | |
| 328 | H | 4-tert.-Butylbenzyl | |
| 329 | H | 2-Chlorobenzyl | |
| 330 | H | 3-Chlorobenzyl | |
| 331 | H | 4-Chlorobenzyl | |
| 332 | H | 2,4-Dichlorobenzyl | |
| 333 | H | 2,6-Dichlorobenzyl | |
| 334 | H | 2,4,6-Trichlorobenzyl | |
| 335 | H | 2-Trifluoromethylbenzyl | |
| 336 | H | 3-Trifluoromethylbenzyl | |
| 337 | H | 4-Trifluoromethylbenzyl | |
| 338 | H | 2-Methoxybenzyl | |
| 339 | H | 4-Methoxybenzyl | |
| 340 | H | 4-tert.-Butoxybenzyl | |
| 341 | H | 4-Phenoxybenzyl | |
| 342 | H | 1-Phenethyl | |
| 343 | H | 2-Phenethyl | |
| 344 | H | 1-Phenylpropyl | |
| 345 | H | 2-Phenylpropyl | |
| 346 | H | 3-Phenylpropyl | |
| 347 | H | 2-Methyl-2-phenylpropyl | |
| 348 | H | 2-Methyl-3-phenylpropyl | |

TABLE VI-continued

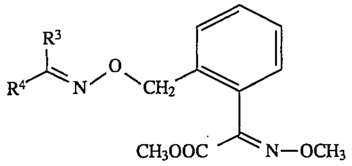

| No. | R³ | R⁴ | Data |
|---|---|---|---|
| 349 | H | 4-Phenylbutyl | |
| 350 | H | 2-Phenyl-1-ethenyl | |
| 351 | H | 1-Phenyl-1-ethenyl | |
| 352 | H | 1-Phenyl-1-propenyl | |
| 353 | H | 1-Phenyl-1-propen-2-yl | |
| 354 | H | 2,2-Diphenylethenyl | |
| 355 | H | Phenoxymethyl | |
| 356 | H | 2-Pyridyl | |
| 357 | H | 3-Pyridyl | |
| 358 | H | 4-Pyridyl | |
| 359 | H | 2,6-Pyrimidinyl | |
| 360 | H | 1,5-Pyrimidinyl | |
| 361 | H | 2-Thienyl | |
| 362 | H | 3-Thienyl | |
| 363 | H | 2-Furyl | |
| 364 | H | 3-Furyl | |
| 365 | H | 1-Pyrrolyl | |
| 366 | H | 1-Imidazolyl | |
| 367 | H | 1,2,4-Triazolyl | |
| 368 | H | 1,3,4-Triazolyl | |
| 369 | H | 4-Thiazolyl | |
| 370 | H | 2-Benzothiazolyl | |
| 371 | H | 2-Pyridyloxy | |
| 372 | H | 2-Pyrimidinyloxy | |
| 373 | H | 2-Pyridylthio | |
| 374 | H | 2-Pyrimidinylthio | |
| 375 | H | 2-Benzothiazolylthio | |
| 376 | H | Phenylthiomethyl | |
| 377 | H | 2-Pyridylmethyl | |
| 378 | H | 3-Pyridylmethyl | |
| 379 | H | Furfuryloxy | |
| 380 | H | Thienylmethoxy | |
| 381 | H | 3-Isoxazolylmethoxy | |
| 382 | H | 2-Oxazolylmethoxy | |
| 383 | H | 2-Pyridylmethoxy | |
| 384 | H | 2'-Furyl-2-ethenyl | |
| 385 | H | 2'-Thienyl-2-ethenyl | |
| 386 | H | 3'-Pyridyl-2-ethenyl | |
| 387 | H | Oxiranyl | |
| 388 | H | 1-Aziridinyl | |
| 389 | H | 1-Azetidinyl | |
| 390 | H | I-Pyrrolidinyl | |
| 391 | H | 2-Tetrahydrofuryl | |
| 392 | H | 2-Tetrahydropyranyl | |
| 393 | H | 3-Tetrahydropyranyl | |
| 394 | H | 1-Piperidinyl | |
| 395 | H | 1-Morpholinyl | |
| 396 | H | 1-Piperazinyl | |
| 397 | H | 1,3-Dioxan-2-yl | |
| 398 | H | 3-Tetrahydrothiopyranyl | |
| 399 | H | 2-Dihydropyranyloxy | |
| 400 | H | 2-Tetrahydropyranyloxy | |
| 401 | H | $CF_3$ | |
| 402 | H | 2-Fluoroethyl | |
| 403 | H | 2,2,2-Trifluoroethyl | |
| 404 | H | Pentafluoroethyl | |
| 405 | H | Chloromethyl | |
| 406 | H | Dichloromethyl | |
| 407 | H | Trichloromethyl | |
| 408 | H | 2-Chloroethyl | |
| 409 | H | 2,2,2-Trichloroethyl | |
| 410 | H | Pentachloroethyl | |
| 411 | H | Cyclopropyl | |
| 412 | H | Cyclobutyl | |
| 413 | H | Cyclopentyl | |
| 414 | H | Cyclohexyl | |
| 415 | H | 1-Methylcyclopropyl | |
| 416 | H | 2,2-Dimethylcyclopropyl | |
| 417 | H | 1-Methylcyclohexyl | |

TABLE VI-continued

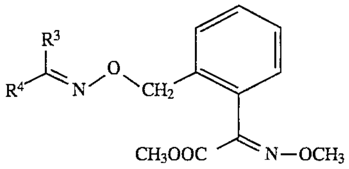

| No. | R³ | R⁴ | Data |
|---|---|---|---|
| 418 | H | 2,2-Difluorocyclopropyl | |
| 419 | H | 2,2-Dichlorocyclopropyl | |
| 420 | H | 2,2-Dibromocyclopropyl | |
| 421 | H | 2,2-Dichloro-3-methylcyclopropyl | |
| 422 | H | 2,2,3,3-Tetrafluorocyclobutyl | |
| 423 | H | Ethenyl | |
| 424 | H | 1-Propenyl | |
| 425 | H | 2-Methyl-1-propenyl | |
| 426 | H | 4-Methylpent-3-en-1-yl | |
| 427 | H | 2-Propenyl | |
| 428 | H | 2-Butenyl | |
| 429 | H | 1-Methyl-2-propenyl | |
| 430 | H | 3-Methyl-2-butenyl | |
| 431 | H | 2,2-Difluoroethenyl | |
| 432 | H | 2,2-Dichloroethenyl | |
| 433 | H | 3,3,3-Trifluoropropenyl | |
| 434 | H | 3,3,3-Trichloropropenyl | |
| 435 | H | 3-Chloro-2-propenyl | |
| 436 | H | Cyclopent-1-enyl | |
| 437 | H | Cyclopentadienyl | |
| 438 | H | Cyclohex-1-enyl | |
| 439 | H | Pentafluorocyclopentadienyl | |
| 440 | H | Pentachlorocyclopentadienyl | |
| 441 | H | 4-Dimethylaminophenyl | m.p.: 70–71° C. |
| 442 | H | 4-Allyloxyphenyl | m.p.: 81–83° C. |
| 443 | H | Diphenylmethyl | m.p.: 66–68° C. |
| 444 | H | Dimethylbenzyl | $^1$H-NMR ($CDCl_3$): δ = 1.45s 3.78s, 4.03s, 5.00s 7.17–7.41m |

TABLE VII

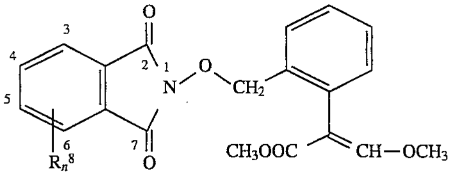

| No. | $R_n^8$ | Data |
|---|---|---|
| 1 | H | m.p. 156–158° C. |
| 2 | 3-Fluoro | |
| 3 | 4-Fluoro | |
| 4 | 3-Chloro | |
| 5 | 4-Chloro | |
| 6 | 3-Bromo | |
| 7 | 4-Bromo | |
| 8 | 3-Iodo | |
| 9 | 4-Iodo | |
| 10 | 3,4-Dichloro | |
| 11 | 3,5-Dichloro | |
| 12 | 3,6-Dichloro | |
| 13 | 4,5-Dichloro | |
| 14 | 3,4,5-Trichloro | |
| 15 | 3,4,6-Trichloro | |
| 16 | 3,4,5,6-Tetrachloro | |
| 17 | 3,4,5,6-Tetrafluoro | |
| 18 | 3,4,5,6-Tetrabromo | |
| 19 | 3,5-Difluoro | |
| 20 | 3,5-Dibromo | |
| 21 | 3-Methyl | |
| 22 | 4-Methyl | |
| 23 | 3-Ethyl | |

TABLE VII-continued

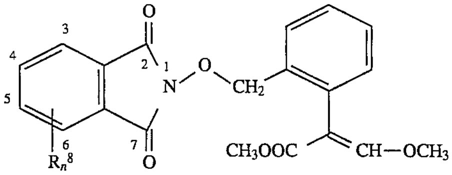

| No. | $R_n^8$ | Data |
|---|---|---|
| 24 | 4-Ethyl | |
| 25 | 3-iso-Propyl | |
| 26 | 4-iso-Propyl | |
| 27 | 3-tert-Butyl | |
| 28 | 4-tert-Butyl | |
| 29 | 3,4-Dimethyl | |
| 30 | 3,5-Dimethyl | |
| 31 | 3,6-Dimethyl | |
| 32 | 4,5-Dimethyl | |
| 33 | 3,4,5-Trimthyl | |
| 34 | 3,4,6-Trimethyl | |
| 35 | 3,4,5,6-Tetramethyl | |
| 36 | 3-Nitro | |
| 37 | 4-Nitro | |
| 38 | 3,5-Dinitro | |
| 39 | 3-Cyano | |
| 40 | 4-Cyano | |
| 41 | 3-Methoxy | |
| 42 | 4-Methoxy | |
| 43 | 3-tert.Butoxy | |
| 44 | 4-tert.Butoxy | |
| 45 | 3-Trifluoromethyl | |
| 46 | 4-Trifluoromethyl | |

TABLE VII-continued

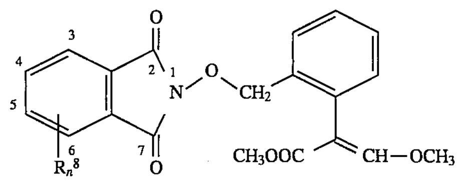

| No. | $R_n^8$ | Data |
|---|---|---|
| 47 | 3-Chloromethyl | |
| 48 | 4-Chloromethyl | |
| 49 | 3-Trifluoromethoxy | |
| 50 | 4-Trifluoromethoxy | |
| 51 | 3-Benzyloxy | |
| 52 | 4-Benzyloxy | |
| 53 | 4,5-Dibenzyloxy | |
| 54 | 3-Phenoxy | |
| 55 | 4-Phenoxy | |
| 56 | 3-Phenyl | |
| 57 | 4-Phenyl | |
| 58 | 3-Pyrid-2'-yl | |
| 59 | 4-Pyrid-2'-yl | |
| 60 | 3-Pyrid-2'-yloxy | |
| 61 | 4-Pyrid-2'-yloxy | |

TABLE VIII

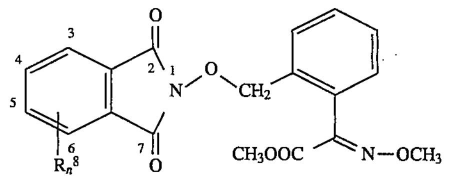

| No. | $R^8n$ | Data |
|---|---|---|
| 1 | H | m.p. 152–155° C. |
| 2 | 3-Fluoro | |
| 3 | 4-Fluoro | |
| 4 | 3-Chloro | |
| 5 | 4-Chloro | |
| 6 | 3-Bromo | |
| 7 | 4-Bromo | |
| 8 | 3-Iodo | |
| 9 | 4-Iodo | |
| 10 | 3,4-Dichloro | |
| 11 | 3,5-Dichloro | |
| 12 | 3,6-Dichloro | |
| 13 | 4,5-Dichloro | |
| 14 | 3,4,5-Trichloro | |
| 15 | 3,4,6-Trichloro | |
| 16 | 3,4,5,6-Tetrachloro | |
| 17 | 3,4,5,6-Tetrafluoro | |
| 18 | 3,4,5,6-Tetrabromo | |
| 19 | 3,5-Difluoro | |
| 20 | 3,5-Dibromo | |
| 21 | 3-Methyl | |
| 22 | 4-Methyl | |
| 23 | 3-Ethyl | |
| 24 | 4-Ethyl | |
| 25 | 3-iso-Propyl | |
| 26 | 4-iso-Propyl | |
| 27 | 3-tert-Butyl | |
| 28 | 4-tert-Butyl | |
| 29 | 3,4-Dimethyl | |
| 30 | 3,5-Dimethyl | |
| 31 | 3,6-Dimethyl | |
| 32 | 4,5-Dimethyl | |
| 33 | 3,4,5-Trimethyl | |
| 34 | 3,4,6-Trimethyl | |
| 35 | 3,4,5,6-Tetramethyl | |
| 36 | 3-Nitro | |
| 37 | 4-Nitro | |
| 38 | 3,5-Dinitro | |

TABLE VIII-continued

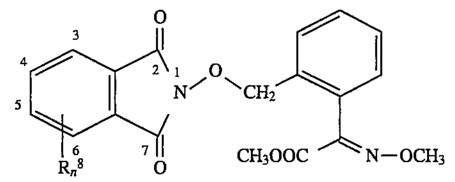

| No. | $R^8n$ | Data |
|---|---|---|
| 39 | 3-Cyano | |
| 40 | 4-Cyano | |
| 41 | 3-Methoxy | |
| 42 | 4-Methoxy | |
| 43 | 3-tert.Butoxy | |
| 44 | 4-tert.Butoxy | |
| 45 | 3-Trifluoromethyl | |
| 46 | 4-Trifluoromethyl | |
| 47 | 3-Chloromethyl | |
| 48 | 4-Chloromethyl | |
| 49 | 3-Trifluoromethoxy | |
| 50 | 4-Trifluoromethoxy | |
| 51 | 3-Benzyloxy | |
| 52 | 4-Benzyloxy | |
| 53 | 4,5-Dibenzyloxy | |
| 54 | 3-Phenoxy | |
| 55 | 4-Phenoxy | |
| 56 | 3-Phenyl | |
| 57 | 4-Phenyl | |
| 58 | 3-Pyrid-2'-yl | |
| 59 | 4-Pyrid-2'-yl | |
| 60 | 3-Pyrid-2'-yloxy | |
| 61 | 4-Pyrid-2'-yloxy | |

TABLE IX

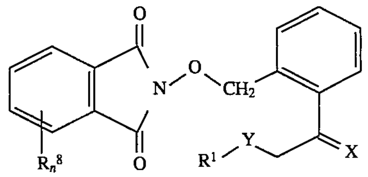

| No. | X | Y | $R^1$ | $R^8$ | Data |
|---|---|---|---|---|---|
| 1 | $CH-SCH_3$ | O | $CH_3$ | H | |
| 2 | $CH-SCH_3$ | NH | $CH_3$ | H | |
| 3 | $CH-SCH_3$ | S | $CH_3$ | H | |
| 4 | $CH_2$ | O | $CH_3$ | N | |
| 5 | $CH_2$ | NH | $CH_3$ | H | |
| 6 | $CH_2$ | S | $CH_3$ | H | |
| 7 | $CH-CH_3$ | O | $CH_3$ | H | |
| 8 | $CH-CH_3$ | NH | $CH_3$ | H | |
| 9 | $CH-CH_3$ | S | $CH_3$ | H | |
| 10 | $CH-CH_3$ | O | $CH_3$ | Perchloro | |
| 11 | $CH-CH_3$ | NH | $CH_3$ | Perchloro | |
| 12 | $CH-CH_3$ | S | $CH_3$ | Perchloro | |
| 13 | $CH-OCH_3$ | NH | $CH_3$ | H | |
| 14 | $CH-OCH_3$ | S | $CH_3$ | H | |
| 15 | $CH-OCH_3$ | NH | $CH_3$ | Perchloro | |
| 16 | $CH-OCH_3$ | S | $CH_3$ | Perchloro | |
| 17 | $N-OCH_3$ | NH | $CH_3$ | H | |
| 18 | $N-OCH_3$ | S | $CH_3$ | H | |
| 19 | $N-OCH_3$ | NH | $CH_3$ | Perchloro | |
| 20 | $N-OCH_3$ | S | $CH_3$ | Perchloro | |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,

*Erysiphe cichoracearum* and *Sphaerotheca fuliginea* in curcurbits,

*Podosphaera leucotricha* in apples,

*Uncinula necator* in vines,

Puccinia species in cereals,

*Rhizoctonia solani* in cotton,

Ustilago species in cereals and sugar cane,

*Venturia inaequalis* (scab) in apples,

Helminthosporium species in cereals,

*Septoria nodorum* in wheat,

*Botrytis cinerea* (gray mold) in strawberries and grapes,

*Cercospora arachidicola* in groundnuts,

*Pseudocercosporella herpotrichoides* in wheat and barley,

*Pyricularia oryzae* in rice,

*Phytophthora infestans* in potatoes and tomatoes,

Fusarium and Verticillium species in various plants,

*Plasmopara viticola* in grapes,

Alternaria species in fruit and vegetables.

The compounds are applied by spraying or dusting the plants with the active ingredients, or treating the seeds of the plants with the active ingredients. They may be applied before or after infection of the plants or seeds by the fungi. Either the fungi themselves, or the plants, seed or materials to be protected against fungus attack, or the soil are treated with a fungicidally effective amount of the active ingredient.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as ligninsulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on *Paecilomyces variotii*. When the active ingredients are used for treating seed, amounts of from 0.001 to 50, and preferably from 0.01 to 10, g per kg of seed are generally required.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. A solution of 90 parts by weight of compound no. 429 (Table I) and 10 parts by weight of N-methyl-α-pyrrolidone, which is suitable for application in the form of very fine drops.

II. A mixture of 20 parts by weight of compound no. 14 (Table II), 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 49 (Table I), 40 parts by weight of cyclohexanone, 30 parts by weight of isobutanol, 20 parts by weight of the adduct of 40 moles of ethylene oxide and 1 mole of castor oil. By finally dispersing the solution in water, an aqueous dispersion is obtained.

IV. An aqueous dispersion of 20 parts by weight of compound no. 56 (Table I), 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By finely distributing the solution in water, an aqueous dispersion is obtained.

V. A hammer-milled mixture of 80 parts by weight of compound no. 14 (Table I), 3 parts by weight of the sodium salt of diisobutylnaphthalene α-sulfonic acid, 10 parts by weight of the sodium salt of a lignin-sulfonic acid obtained from a sulfite waste liquor, and 7 parts by weight of powered silica gel. By finely dispersing the mixture in water, a spray liquor is obtained.

VI. An intimate mixture of 3 parts by weight of compound no. 17 (Table II) and 97 parts by weight of particulate kaolin. The dust contains 3 wt % of the active ingredient.

VII. An intimate mixture of 30 parts by weight of compound no. 17 (Table I), 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 571 (Table I), 10 parts of the sodium salt of a phenolsulfonic acid-urea-formaldehyde condensate, 2 parts of silica gel and 48 parts by weight of water, which dispersion can be further diluted.

IX. A stable oily dispersion of 20 parts by weight of compound no. 616 (Table I), 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

USE EXAMPLES

The active ingredient used for comparison purposes was 2-(phenoxymethyl) phenylglyoxylic acid-methyl ester-O-methyloxime (A) disclosed in EP 253,213.

Use Example 1

Action on wheat brown rust

Leaves of pot-grown wheat seedlings of the "Kanzler" variety were dusted with spores of brown rust (*Puccinia recondita*). The pots were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients nos. 49, 429, 56, 14, 15, 16, 17, 582, 578, 573, 592, 571, 704, 705 and 616 from Table I and nos. 17 and 644 from Table II, applied as 0.025 wt% spray liquors, have a better fungicidal action (95%) than prior art comparative compound A (50%).

Use Example 2

Action on *Pyricularia oryzae* (protective)

Leaves of pot-grown rice seedlings of the "Bahia" variety were sprayed to runoff with aqueous emulsions containing (dry basis) 80% of active ingredient and 20% of emulsifier, and inoculated 24 hours later with an aqueous spore suspension of *Pyricularia oryzae*. The plants were then set up in climatic cabinets at 22° to 24° C. and 95 to 99% relative humidity. The extent of fungus attack was assessed after 6 days.

The results show that active ingredients nos. 429, 583, 593, 592, 571, 706 and 616 from Table I and nos. 14, 15, 16, 17, 582, 592, 571, 769, 782, 672, 644 and 583 from Table II, applied as 0.05 wt % spray liquors, have a very good fungicidal action (100%).

The novel compounds are also suitable for effectively combating pests such as insects, arachnids and nematodes. They may be used as pesticides in crop protection and in the hygiene, stores protection and veterinary sector.

Examples of injurious insects belonging to the Lepidoptera order are *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Platypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis.*

Examples from the Coleoptera order are *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica* 12-*punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Ortiorrhynchus ovatus, Phaedon cochleariae, Phyllotreta chrysocephala,* Phyllophaga sp., *Phyllopertha horticola, Phyllotretra nemorum, Phyllotreta striolata, Popillia japonica, Sitona lineatus* and *Sitophilus granaria.*

Examples from the Diptera order are *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa. Examples from the Thysanoptera order are Franklinella fusca, Franklinielle occidentalis, Frankliniella tritici, Scirtothrips citri, Thrips oryzae, Thrips palmi* and *Thrips tabaci.*

Examples from the Hymenoptera order are *Athalia rosae, Atta cephalotes, Atta sexdens, Atta texana, Hoplocampa minuta, Hoplocampa testudinea, Monomorium pharaonis, Solenopsis geminata* and *Solenopsis invicta.*

Examples from the Heteroptera order are *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor.*

Examples from the nematodes class are root-knot nematodes, e.g., *Meloidogyne hapla, Meloidogyne incognita* and *Meloidogyne javanica*, cyst-forming nematodes, e.g., *Globodera rostochiensis, Heterodera avenae, Hetrodera glycinae, Heterodera schachtii* and *Heterodera trifolii*, and stem and leaf eelworms, e.g., *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

When the active ingredients are used for combating pests, the concentrations in the finished formulations may vary over a wide range. Generally, the concentration is from 0.0001 to 10, and preferably from 0.001 to 0.1, %.

The active ingredients may also be successfully used in the ultra-low-volume method (ULV), where it is possible to apply formulations containing more than 95 wt % of active ingredient, or even the active ingredient without any additives.

When the active ingredients are used for combating pests in the open, the application rates are from 0.01 to 10, and preferably from 0.1 to 1.0, kg/ha.

Use Example 3

*Tetranychus telarius* (spider mite); contact action—spray test

Potted bush beans which had developed the first pair of true leaves and were heavily infested with all stages of the spider mite *Tetranychus telarius* were sprayed to runoff in a spray cabinet with aqueous formulations of the active ingredients. The plants were placed on a rotating disc and sprayed from all sides with 50 ml of spray liquor. The plants were heavily infested with mites and numerous eggs had been laid on them. The action was assessed after 5 days by means of a binocular microscope. During this period, the plants were kept under normal greenhouse conditions.

| | Application rate in ppm | Mortality In % |
|---|---|---|
| Compound no. from Table I | | |
| 49 | 100 | 80 |
| 36 | 100 | 80 |
| 43 | 1000 | 100 |
| 429 | 1000 | 100 |
| 38 | 40 | 100 |
| 39 | 100 | 100 |
| 45 | 1000 | 100 |
| 582 | about 20 | 100 |
| 579 | 20 | 80 |
| 583 | 40 | 100 |
| 573 | 20 | 100 |
| 593 | 1000 | 80 |
| 592 | 40 | 100 |
| 704 | about 20 | 100 |
| 705 | 40 | 100 |
| Compound no. from Table II | | |
| 37 | 1000 | 100 |
| 39 | 1000 | 100 |
| 45 | 1000 | 100 |

Use Example 4

*Musca domestica* (housefly); continuous contact action

Both the tops and bottoms of Petri dishes 10 cm in diameter were lined with a total of 1 ml of acetonic solutions of the active ingredients. After the solvent had evaporated (about 30 mins.) , 10 flies and absorbent cotton steeped in water were introduced into each dish and the dishes closed. The flies in supine position were counted after 24 hours.

If a kill rate of 80 to 100% occurs at a concentration of 0.01 mg/dish, the test is continued with falling concentrations.

| Compound no. from Table I | Application rate in mg | Mortality in % |
|---|---|---|
| 49 | 0.1 | 80 |
| 36 | 1.0 | 80 |
| 37 | 0.1 | 100 |
| 582 | 0.1 | 80 |
| 593 | 0.1 | 60 |
| 705 | 0.1 | 100 |
| 706 | 0.1 | 100 |

Use Example 5

*Plutella maculipennis* (diamondback moth); ingestion-inhibiting action

Young kohlrabi leaves are dipped for 3 seconds into aqueous solutions of the candidate compounds, and then placed on a round filter paper 9 cm in diameter which has been moistened with 0.5 ml of water. The filter paper is then placed in a Petri dish 10 cm in diameter. 10 caterpillars in the 4th larval stage are then placed on each leaf, and the Petri dish is closed. Ingestion inhibition is determined in % after 48 hours.

| Compound no. from Table I | Application rate in ppm | Mortality in % |
|---|---|---|
| 49 | 200 | 80 |
| 36 | 200 | 80 |
| 429 | 1000 | 80 |
| 16 | 400 | 80 |
| 582 | 400 | 100 |
| 593 | 1000 | 80 |
| 592 | 400 | 80 |
| 705 | 400 | 80 |
| 706 | 400 | 80 |

Use Example 6

Action on Peronospora in grapes

Leaves of potted vines of the "Müller Thurgau" variety were sprayed with aqueous liquors containing (dry basis) 80% of active ingredient and 20% of emulsifier. To assess the duration of action of the active ingredients, the plants were, after the sprayed-on layer had dried, set up in the greenhouse for 8 days. Only then were the leaves infected with a zoospore suspension of *Plasmopara viticola*. The vines were then placed for 48 hours in a water-vapor-saturated chamber at 24° C. and then for 5 days in a greenhouse at from 20° to 30° C. To accelerate the sporangiophore discharge, the plants were then again set up in the moist chamber for 16 hours. The extent to which the leaves had been attacked was then assessed.

The results show that active ingredients nos. 49, 429, 56, 14, 15, 16, 17, 582, 578, 573, 592, 571, 704, 705, 616, 117, 156, 579, 583, 593 and 706 from Table I, Nos. 17, 644, 117, 429, 56, 43, 36, 49, 14, 15, 16, 582, 614 and 672 from Table II, and compound no. 1 from Table VII have, when applied as 0.025 wt % spray liquors, a better fungicidal action (95%) than the prior art comparative agent A (50%).

We claim:

1. An O-benzyloxime ether of the formula I

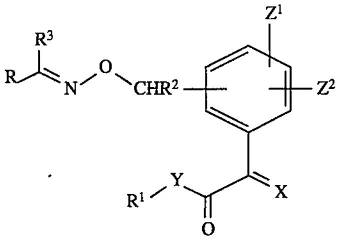

(I)

wherein

X is CH—$C_{1-4}$ alkyl

Y is O, S or $NR^5$;

$R^1$, $R^2$ and $R^5$ are H or $C_1$–$C_4$-alkyl;

$Z^1$ and $Z^2$ are identical or different and each is H, halogen, methyl, methoxy or cyano;

$R^3$ is hydrogen, cyano, straight-chain or branched $C_1$–$C_{10}$-alkyl, $C_1$–$C_4$-haloalkyl, $C_3$–$C_6$-cycloalkyl, $C_3$–$C_6$-halocycloalkyl, $C_3$–$C_6$-cycloalkyl-$C_1$–$C_4$-alkyl, $C_1$–$C_4$-alkoxy-$C_1$–$C_4$-alkyl, $C_1$–$C_4$-alkylthio-$C_1$–$C_4$-alkyl, arylthio-$C_1$–$C_4$-alkyl, $C_2$–$C_6$-alkenyl, $C_2$–$C_5$-haloalkenyl, $C_3$–$C_6$-cycloalkenyl, $C_3$–$C_6$-halocycloakenyl, $C_2$–$C_6$-alkynyl, $C_1$–$C_6$-alkoxy, $C_1$–$C_6$-haloalkoxy, $C_1$–$C_4$-alkylthio, benzylthio, $C_1$–$C_4$-alkylcarbonyl, substituted or unsubstituted phenylcarbonyl, substituted or unsubstituted benzylcarbonyl, $C_1$–$C_4$-alkoxycarbonyl, substituted or unsubstituted phenoxycarbonyl, substituted or unsubstituted benzyloxycarbonyl, substituted or unsubstituted aryl, substituted or unsubstituted aryloxy, substituted or unsubstituted arylthio, substituted or unsubstituted aryl-$C_1$–$C_4$-alkyl, substituted or unsubstituted aryl-$C_2$–$C_4$-alkenyl, substituted or unsubstituted aryloxy-$C_1$–$C_4$-alkyl, substituted or unsubstituted arylthio-$C_1$–$C_4$-alkyl, substituted or unsubstituted hetaryl, substituted or unsubstituted hetaryloxy, substituted or unsubstituted hetarylthio, substituted or unsubstituted heteroaryl-$C_1$–$C_4$-alkyl, substituted or unsubstituted hetaryl-$C_2$–$C_4$-alkenyl, substituted or unsubstituted hetaryloxy-$C_1$–$C_4$-alkyl, substituted or unsubstituted heterocyclyl or substituted or unsubstituted heterocyclyloxy, halogen, $N(R^6)_2$, where the radical $R^6$ are identical or different and each is H, $C_1$–$C_6$-alkyl or substituted or unsubstituted phenyl, —CO—$N(R^7)_2$, where the radicals $R^7$ are identical or different and each is H or $C_1$–$C_4$-alkyl, substituted or unsubstituted meaning, in addition to hydrogen, the radicals halogen, cyano, nitro, $C_1$–$C_4$-alkyl, $C_1$–$C_4$-alkoxy, $C_1$–$C_4$-haloalkyl, $C_1$–$C_4$-haloalkoxy, $C_1$–$C_{10}$-alkoximino-$C_1$–$C_2$-alkyl, aryl, aryloxy, benzyloxy, hetaryl, hetaryloxy, -$C_3$–$C_6$-cycloalkyl, heterocyclyl, heterocyclyloxy; and $R^4$ is substituted or unsubstituted hetaryl, substituted or unsubstituted hetaryloxy, substituted or unsubstituted hetarylthio, substituted or unsubstituted heteroaryl-$C_1$–$C_4$-alkyl, substituted or unsubstituted hetaryl-$C_1$–$C_4$-alkenyl, substituted or unsubstituted hetaryloxy-$C_1$–$C_4$-alkyl, substituted or unsubstituted heterocyclyl or substituted or unsubstituted heterocyclyloxy.

2. The O-benzyloxime ether of claim 1, of the formula (II)

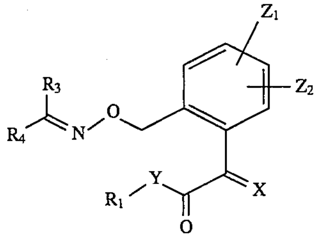

(II)

3. The O-benzyloxime ether of claim 1, of the formula (II)

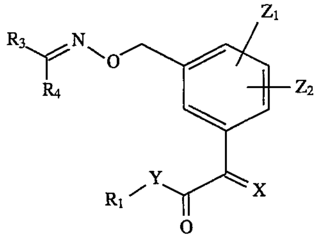

(III)

4. The O-benzyloxime ether of claim 1, wherein X is $CHCH_3$ or $CHCH_2CH_3$.

5. The O-benzyloxime ether of claim 1, wherein $Z^1$ and $Z^2$ are hydrogen.

6. The O-benzyloxime ether of claim 1, wherein $R^1$ is methyl.

7. The O-benzyloxime ether of claim 1, wherein $R^2$ is hydrogen.

8. The O-benzyloxime ether of claim 1, wherein $R^3$ is selected from the group consisting of cyano, methyl and ethyl.

9. The O-benzyloxime ether of claim 1, wherein $R^4$ is substituted hetaryl.

10. The O-benzyloxime ether of claim 1, wherein $R^4$ is substituted by a radical selected from the group consisting of halogen, phenyl, methyl, ethyl, iso-propyl, tert-butyl, methoxy, ethoxy, trifluoromethyl and 2,2,2-trifluoroethoxy.

11. The O-benzyloxime ether of claim 1, wherein $R^4$ is substituted pyridyl or pyrimidyl.

12. The O-benzyloxime ether of claim 1, wherein $R^4$ is substituted pyrimidyl, wherein the substitution is adjacent to a pyrimidyl-nitrogen.

13. The O-benzyloxime ether of claim 1, wherein $R^4$ is substituted by a radical selected from the group consisting of $C_{1-4}$ alkyl, $C_{1-4}$ alkoxy, $C_{1-2}$ haloalkyl, $C_{1-2}$ haloalkoxy, phenyl and substituted phenyl.

14. A fungicide containing an inert carrier and a fungicidally effective amount of an O-benzyloxime ether of the formula I

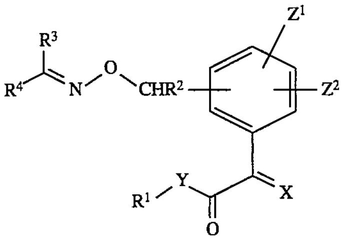

(I)

wherein

X is CH—$CH_{1-4}$;

Y is O, S or $NR^5$;

$R^1$, $R^2$ and $R^5$ are H or $C_1$–$C_4$-alkyl;

$Z^1$ and $Z^2$ are indentical or different and each is H, halogen, methyl, methoxy or cyano;

$R^3$ is hydrogen, cyano, straight-chain or branched $C_1$–$C_{10}$-alkyl, $C_1$–$C_4$-haloalkyl, $C_3$–$C_6$-cycloalkyl, $C_3$–$C_6$-halocycloalkyl, $C_3$–$C_6$-cycloalkyl-$C_1$–$C_4$-alkyl, $C_1$–$C_4$-alkoxy-$C_1$–$C_4$-alkyl, $C_1$–$C_4$-alkylthio-$C_1$–$C_4$-alkyl, arylthio-$C_1$–$C_4$-alkyl, $C_2$–$C_6$-alkenyl, $C_2$–$C_5$-haloalkenyl, $C_3$–$C_6$-cycloalkenyl, $C_3$–$C_6$-halocycloalkenyl, $C_2$–$C_6$-alkynyl, $C_1$–$C_6$-alkoxy, $C_1$–$C_6$-haloalkoxy, $C_1$–$C_4$-alkylthio, benzylthio, $C_1$–$C_4$-alkylcarbonyl, substituted or unsubstituted phenylcarbonyl, substituted or unsubstituted benzylcarbonyl, $C_1$–$C_4$-alkoxycarbonyl, substituted or unsubstituted phenoxycarbonyl, substituted or unsubstituted benzyloxycarbonyl, substituted or unsubstituted aryl, substituted or unsubstituted aryloxy, substituted or unsubstituted arylthio, substituted or unsubstituted aryl-$C_1$–$C_4$-alkyl, substituted or unsubstituted aryl-$C_2$–$C_4$-alkenyl, substituted or unsubstituted aryloxy-$C_1$–$C_4$-alkyl, substituted or unsubstituted arylthio-$C_1$–$C_4$-alkyl, substituted or unsubstituted hetaryl, substituted or unsubstituted hetaryloxy, substituted or unsubstituted hetarylthio, substituted or unsubstituted heteroaryl-$C_1$–$C_4$-alkyl, substituted or unsubstituted hetaryl-$C_2$–$C_4$-alkenyl, substituted or unsubstituted hetaryloxy-$C_1$–$C_4$-alkyl, substituted or unsubstituted heterocyclyl or substituted or unsubstituted heterocyclyloxy, halogen, $N(R^6)_2$, where the radicals $R^6$ are identical or different and each is H, $C_1$–$C_6$-alkyl or substituted or unsubstituted phenyl, —CO—$N(R^7)_2$, where the radicals $R^7$ are identical or different and each is H or $C_1$–$C_4$-alkyl, substituted or unsubstituted meaning, in addition to hydrogen, the radicals halogen, cyano, nitro, $C_1$–$C_4$-alkyl, $C_1$–$C_4$-alkoxy, $C_1$–$C_4$-haloalkyl, $C_1$–$C_4$-haloalkoxy, $C_1$–$C_{10}$-alkoximino-$C_1$–$C_2$-alkyl, aryl, aryloxy, benzyloxy, hetaryl, hetaryloxy, —$C_3$–$C_6$-cycloalkyl, heterocyclyl, heterocyclyloxy; and $R^4$ is substituted or unsubstituted hetaryl, substituted or unsubstituted hetaryloxy, substituted or unsubstituted hetarylthio, substituted or unsubstituted heteroaryl-$C_1$–$C_4$-alkyl, substituted or unsubstituted hetaryl-$C_2$–$C_4$-alkenyl, substituted or unsubstituted hetaryloxy-$C_1$–$C_4$-alkyl, substituted or unsubstituted heterocyclyl or substituted or unsubstituted heterocyclyloxy.

15. A process for combating fungi, wherein the fungi, or the materials, plants or seed threatened by fungus attack, or the soil, are treated with a fungicidally effective amount of a compound of the formula I

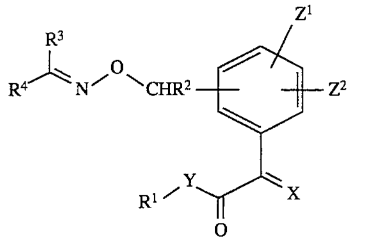

(I)

wherein

X is CH—$CH_{1-4}$;

Y is 0, S or $NR^5$;

$R^1$, $R^2$ and $R^5$ are H or $C_1$–$C_4$alkyl;

$Z^1$ and $Z^2$ are identical or different and each is H, halogen, methyl, methoxy or cyano;

$R^3$ is hydrogen, cyano, straight-chain or branched $C_1$–$C_{10}$-alkyl, $C_1$–$C_4$-haloalkyl, $C_3$–$C_6$-cycloalkyl, $C_3$–$C_6$-halocycloalkyl, $C_3$–$C_6$-cycloalkyl-$C_1$–$C_4$-alkyl, $C_1$–$C_4$-alkyl, $C_1$–$C_4$-alkylthio-$C_1$–$C_4$-alkyl, arylthio-$C_1$–$C_4$-alkyl, $C_2$–$C_6$-alkenyl, $C_2$–$C_5$-haloalkenyl, $C_3$–$C_6$-cycloalkenyl, $C_3$–$C_6$-halocycloalkenyl, $C_2$–$C_6$-alkynyl, $C_1$–$C_6$-alkoxy, $C_1$–$C_6$-haloalkoxy, $C_1$–$C_4$-alkylthio, benzylthio, $C_1$–$C_4$-alkylcarbonyl, substituted or unsubstituted phenylcarbonyl, substituted or unsubstituted benzylcarbonyl, $C_1$–$C_4$-alkoxycarbonyl, substituted or unsubstituted phenoxycarbonyl, substituted or unsubstituted benzyloxycarbonyl, substituted or unsubstituted aryl, substituted or unsubstituted aryloxy, substituted or unsubstituted arylthio, substituted or unsubstituted aryl-$C_1$–$C_4$-alkyl, substituted or unsubstituted aryl-$C_2$–$C_4$-alkenyl, substituted or unsubstituted aryloxy-$C_1$–$C_4$-alkyl, substituted or unsubstituted arylthio-$C_1$–$C_4$-alkyl, substituted or unsubstituted hetaryl, substituted or unsubstituted hetaryloxy, substituted or unsubstituted hetarylthio, substituted or unsubstituted heteroaryl-$C_1$–$C_4$-alkyl, substituted or unsubstituted hetaryl-$C_2$–$C_4$-alkenyl, substituted or unsubstituted hetaryloxy-$C_1$–$C_4$-alkyl, substituted or unsubstituted heterocyclyl or substituted or unsubstituted heterocyclyloxy, halogen, $N(R^6)_2$, where the radicals $R^6$ are identical or different and each is H, $C_1$–$C_6$-alkyl or substituted or unsubstituted phenyl, —CO—$N(R^7)_2$, where the radicals $R^7$ are identical or different and each is H or $C_1$–$C_4$-alkyl, substituted or unsubstituted meaning, in addition to hydrogen, the radicals halogen, cyano, nitro, $C_1$–$C_4$-alkyl, $C_1$–$C_4$-alkoxy, $C_1$–$C_4$-haloalkyl, $C_1$–$C_4$-haloalkoxy, $C_1$–$C_{10}$-alkoximino-$C_1$–$C_2$-alkyl, aryl, aryloxy, benzyloxy, hetaryl, hetaryloxy, -$C_3$–$C_6$-cycloalky, heterocyclyl, heterocyclyloxy; and $R^4$ is substituted or unsubstituted hetaryl, substituted or unsubstituted hetaryloxy, substituted or unsubstituted hetarylthio, substituted or unsubstituted heteroaryl-$C_1$–$C_4$-alkyl, substituted or unsubstituted hetaryl-$C_2$–$C_4$-alkenyl, substituted or unsubstituted hetaryloxy-$C_1$–$C_4$-alkyl, substituted or unsubstituted heterocyclyl or substituted or unsubstituted heterocyclyloxy.

* * * * *